(12) United States Patent
Weinkam et al.

(10) Patent No.: US 11,911,091 B2
(45) Date of Patent: Feb. 27, 2024

(54) MEDICAL DEVICE SYSTEMS AND METHODS FOR ACTIVATING TRANSDUCERS BASED ON DELIVERY SHAFT MEMBER TEMPERATURE

(71) Applicant: KARDIUM INC., Burnaby (CA)

(72) Inventors: Daniel Robert Weinkam, Coquitlam (CA); Shane Fredrick Miller-Tait, North Vancouver (CA); Lok Tin Lam, Vancouver (CA)

(73) Assignee: KARDIUM INC., Burnaby (CA)

( * ) Notice: Subject to any disclaimer, the term of this patent is extended or adjusted under 35 U.S.C. 154(b) by 996 days.

(21) Appl. No.: 16/661,171

(22) Filed: Oct. 23, 2019

(65) Prior Publication Data
US 2020/0054385 A1 Feb. 20, 2020

Related U.S. Application Data

(63) Continuation of application No. PCT/CA2018/000089, filed on May 9, 2018.
(Continued)

(51) Int. Cl.
*A61B 18/14* (2006.01)
*A61B 18/16* (2006.01)
*A61B 18/00* (2006.01)

(52) U.S. Cl.
CPC ........ *A61B 18/148* (2013.01); *A61B 18/1492* (2013.01); *A61B 18/16* (2013.01);
(Continued)

(58) Field of Classification Search
CPC .............. A61B 18/148; A61B 18/1492; A61B 2018/00714; A61B 2018/00791;
(Continued)

(56) References Cited

U.S. PATENT DOCUMENTS 5,755,715 A * 5/1998 Stern ...................... A61B 18/00
606/42
5,906,614 A * 5/1999 Stern .................. A61B 18/1492
606/41

(Continued)

FOREIGN PATENT DOCUMENTS

WO 2011119957 A2 9/2011

OTHER PUBLICATIONS

International Search Report issued in Intl. Appln. No. PCT/CA2018/000089 dated Aug. 9, 2018.
(Continued)

*Primary Examiner* — Daniel W Fowler
*Assistant Examiner* — Lindsay Regan Lancaster
(74) *Attorney, Agent, or Firm* — ROSSI, KIMMS & McDOWELL LLP

(57) ABSTRACT

In at least a medical system including a structure, a plurality of transducers located on the structure, a shaft member configured to percutaneously deliver the structure to a location within a patient, a plurality of conductors at least partially within the shaft member and coupled to the transducers, and a controller operatively coupled to the transducers via the conductors, the controller may cause first electrical power to be delivered to one or more of the transducers for a first period of time, where second electrical power less than the first electrical power, if delivered for a second period of time longer than the first period time would result in a steady-state temperature of a portion of the shaft member that would be just below a safe temperature limit for at least the portion of the shaft member.

31 Claims, 16 Drawing Sheets

Related U.S. Application Data

(60) Provisional application No. 62/518,039, filed on Jun. 12, 2017.

(52) U.S. Cl.
CPC ............ *A61B 2018/00077* (2013.01); *A61B 2018/00214* (2013.01); *A61B 2018/00351* (2013.01); *A61B 2018/00577* (2013.01); *A61B 2018/00702* (2013.01); *A61B 2018/00714* (2013.01); *A61B 2018/00791* (2013.01); *A61B 2018/00839* (2013.01); *A61B 2018/00875* (2013.01); *A61B 2018/00988* (2013.01)

(58) Field of Classification Search
CPC .......... A61B 2018/00797; A61B 18/16; A61B 2018/00077; A61B 2018/1417; A61B 2018/00666; A61B 2018/142; A61B 2018/00577; A61B 2018/00214; A61B 2018/00702; A61B 2018/00267; A61B 5/053; A61B 5/01; A61B 18/04; A61B 2018/1467; A61B 5/6858; A61B 5/6853; A61B 2018/1475; A61B 2018/00351; A61B 2018/00839; A61B 2018/00875; A61B 2018/00988; A61B 2018/00642
See application file for complete search history.

(56) References Cited

U.S. PATENT DOCUMENTS

| | | | | |
|---|---|---|---|---|
| 5,957,920 A * | 9/1999 | Baker | ................. | A61B 18/1485 607/101 |
| 6,123,702 A * | 9/2000 | Swanson | ............ | A61B 18/1206 606/49 |
| 8,273,079 B2 | 9/2012 | Hoey | | |
| 8,486,063 B2 | 7/2013 | Werneth | | |
| 9,011,423 B2 | 4/2015 | Brewster | | |
| 9,452,016 B2 | 9/2016 | Moisa | | |
| 9,492,227 B2 | 11/2016 | Lopes | | |
| 9,566,115 B2 | 2/2017 | Van Der Weide | | |
| 2004/0122420 A1* | 6/2004 | Amoah | .............. | A61B 18/1477 606/41 |
| 2005/0065511 A1* | 3/2005 | Geistert | ............. | A61B 18/1492 606/41 |
| 2008/0188913 A1* | 8/2008 | Stone | ................. | A61B 18/1492 607/99 |
| 2010/0152724 A1* | 6/2010 | Marion | .............. | A61B 18/1233 606/41 |
| 2011/0077641 A1* | 3/2011 | Dunning | ........... | A61B 18/1233 606/34 |
| 2013/0310828 A1* | 11/2013 | Reinders | ................ | A61B 5/743 606/34 |
| 2015/0005758 A1* | 1/2015 | Berger | ............... | A61B 18/1233 606/34 |
| 2017/0119461 A1* | 5/2017 | Godara | ................ | A61B 18/148 |

OTHER PUBLICATIONS

Written Opinion issued in Intl. Appln. No. PCT/CA2018/000089 dated Aug. 9, 2018.

Kottkamp et al. "Global multielectrode contact mapping plus ablation with a single catheter: Preclinical and preliminary experience in humans with atrial fibrillation." Journal of Cardiovascular Electrophysiology. 2017:1-10.

Mounsey. "A novel multielectrode combined mapping and ablation basket catheter: A future player in the atrial fibrillation ablation space?" Journal of Cardiovascular Electrophysiology. 2017:1-2.

* cited by examiner

MEDICAL DEVICE SYSTEMS AND METHODS FOR ACTIVATING TRANSDUCERS BASED ON DELIVERY SHAFT MEMBER TEMPERATURE

CROSS-REFERENCE TO RELATED APPLICATIONS

This application is a continuation of prior International Application No. PCT/CA2018/000089, filed May 9, 2018, which claims the benefit of U.S. Provisional Application No. 62/518,039, filed Jun. 12, 2017, the entire disclosure of both of these applications is hereby incorporated herein by reference.

TECHNICAL FIELD

Aspects of this disclosure generally are related at least to medical systems including carrier members that facilitate delivery of transducers to a bodily cavity. Delivery of the transducers may include percutaneous or intravascular delivery thereof.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left and right atria to block various paths taken by the spurious electrical signals. Such lesions were originally created using incisions, but are now typically created by ablating the tissue with various techniques including radio-frequency (RF) energy, microwave energy, laser energy, electroporation and cryogenic techniques. The procedure is performed with a high success rate under the direct vision that is provided in open procedures, but is relatively complex to perform intravascularly or percutaneously because of the difficulty in creating the lesions in the correct locations using catheter-based systems.

Difficulties in creating lesions in the correct locations within a bodily cavity using intravascular or percutaneous techniques are often associated with the delivery of various ablative elements to the bodily cavity and the manipulation of the various ablative elements within the bodily cavity. In this regard, a carrier member (e.g., an elongated shaft member) is employed to deliver and position various transducers at the desired locations in a bodily cavity. In many cases, various electrical conductors with portions thereof located within the carrier member, are employed to provide data communication paths, power delivery paths or both data communication and power delivery paths with various ones the transducers. As the need to activate ever-increasing numbers of transducers rises, increased energy levels will be required to be delivered via the various electrical conductors located in the carrier member. In some cases, these increased energy levels may cause a temperature of the carrier member to increase to undesired levels. These undesired temperature levels may render the carrier member uncomfortable to handle, or in some extreme cases, cause the carrier member to reach temperatures that may be determined to burn or otherwise thermally harm a heath care practitioner or patient.

In this regard, the present inventors recognized that there exists a need in the art for improvement in the activation of transducers or other sensing or ablative elements in one or more preferred locations within a bodily cavity, such as a heart, in order to successfully perform various diagnostic or treatment procedures.

SUMMARY

At least the above-discussed need is addressed and technical solutions are achieved by various embodiments of the present invention. In some embodiments, device systems and methods executed by such systems exhibit enhanced capabilities for the delivery and placement of one or more transducers provided by one or more elongate members at various preferred locations with respect to various regions of a tissue wall of a bodily cavity, and, in some embodiments, formation of one or more lesions in at least one of the various regions.

In some embodiments, various systems may include combinations and subsets of the systems summarized above.

According to some embodiments, a medical device system may be summarized as including a structure, a plurality of transducers located on the structure, a shaft member configured to percutaneously deliver the structure to a location within a patient, a plurality of conductors coupled to the plurality of transducers, at least a portion of each conductor of the plurality of conductors located within the shaft member, and a controller operatively coupled to the plurality of transducers and configured to cause delivery of electrical power to the plurality of transducers via the plurality of conductors. According to various embodiments, the shaft member includes a distal end portion and a proximal end portion, and at least part of the shaft member may be sized to be percutaneously deliverable toward the location within the patient distal end portion ahead of the proximal end portion. According to some embodiments, a first output power limit is defined as a level of power that, if delivered via a first set of conductors of the plurality of conductors to a first transducer set of the plurality of transducers for a first time period, causes a portion of the shaft member to transition from a first temperature to a first steady-state temperature immediately upon conclusion of the first time period, the first steady-state temperature determined insufficient to cause thermally-induced tissue cellular damage. According to some embodiments, the controller may be configured to cause delivery, via a second set of conductors of the plurality of conductors, of second electrical power to a second transducer set of the plurality of transducers for a second time period, an average of the second electrical power over the second time period being greater than the first output power limit, the second time period being shorter than the first time period, and the delivery of the second electrical power to the second transducer set for the second time period being (a) sufficient to cause tissue ablation via the second transducer set, and (b) sufficient to cause the portion of the shaft member to transition from the first temperature to a second temperature immediately upon conclusion of the second time period, the second temperature being less than or equal to the first steady-state temperature.

According to some embodiments, the second electrical power, if delivered to the second transducer set for a third time period longer than the second time period, may be sufficient to cause the portion of the shaft member to transition from the first temperature to a third temperature, the third temperature determined sufficient to cause thermally-induced tissue cellular damage. In some embodiments the third temperature may be a steady-state temperature. In some embodiments, the third temperature may be greater than the first steady-state temperature. In some embodiments, the third time period may be shorter than the first time period. In some embodiments, the third temperature may be sufficient to cause thermally-induced tissue cellular necrosis.

In some embodiments, the second temperature may be a temperature within a range of 43 to 60 degrees Celsius, inclusive. In some embodiments, the second temperature may be a temperature less than or equal to 48 degrees Celsius, and the second time period may be shorter than or equal to 10 minutes. In some embodiments, the second temperature may be a temperature less than or equal to 60 degrees Celsius, and the second time period may be shorter than or equal to 1 minute. In some embodiments, the first temperature may be an ambient temperature of the portion of the shaft member. In some embodiments, the first temperature may be a temperature that is less than or equal to a temperature of a portion of the patient that the at least part of the shaft member is percutaneously deliverable through.

According to some embodiments, the controller may be configured to cause third electrical power to be delivered to at least a third transducer set of the plurality of transducers, the third electrical power delivered to at least the third transducer set prior to the delivery of the second electrical power to the second transducer set. In some embodiments, the first temperature may be a temperature of the portion of the shaft member after the third electrical power is delivered to at least the third transducer set. In some embodiments, the third electrical power delivered to at least the third transducer set may be sufficient to cause tissue ablation via the third transducer set.

In some embodiments, the first temperature may be a temperature of the portion of the shaft member prior to the controller causing electrical power to be delivered to any transducer of the plurality of transducers. In some embodiments, the first temperature may be a temperature of the portion of the shaft member prior to the controller causing electrical power to be delivered to any particular transducer of the plurality of transducers to cause the particular transducer to emit energy sufficient for tissue ablation.

According to some embodiments, the second electrical power may include a second output power limit that is greater than the first output power limit. In some embodiments, the controller may be configured to cause third electrical power to be delivered to at least a third transducer set of the plurality of transducers, the third electrical power delivered to at least the third transducer set delivered after the delivery of the second electrical power to the second transducer set has completed. In some embodiments, the third electrical power may include a third output power limit that is determined based at least on a temperature of the portion of the shaft member at a point in time after completion of delivery of the second electrical power and before the delivery of the third electrical power is started. In some embodiments, the third output power limit may be less than the second output power limit. In some embodiments, the third output power limit may be less than the first output power limit.

In some embodiments, the medical device system may include at least a first temperature sensor configured to sense the first temperature, the second temperature, or both the first temperature and the second temperature. In some embodiments, the first temperature sensor is located on or in the shaft member. In some embodiments, the distal end portion of the shaft member includes a distal end, and the proximal end portion of the shaft member include a proximal end, and the first temperature sensor may be located on or in the shaft member at a location closer to the distal end of the shaft member than to the proximal end of the shaft member. In some embodiments, the distal end portion of the shaft member includes a distal end, and the proximal end portion of the shaft member includes a proximal end, and the first temperature sensor may be located on or in the shaft member at a location closer to the proximal end of the shaft member than to the distal end of the shaft member. In some embodiments, the first temperature sensor may be provided at least in part by a first conductor, at least a portion thereof included in the shaft member, and the controller may be configured to determine the first temperature, the second temperature, or both the first temperature and the second temperature based at least on a resistance of at least part of the first conductor.

In some embodiments, the shaft member may include at least a first lumen extending between the proximal end portion of the shaft member and the distal end portion of the shaft member. In some embodiments, the plurality of conductors may be located in the first lumen. In some embodiments, the shaft member may include at least a first lumen extending between the proximal end portion of the shaft member and the distal end portion of the shaft member, and the structure may be configured to be delivered through the first lumen as the structure is percutaneously delivered toward the location within the patient.

In some embodiments, at least part of each conductor of the plurality of conductors may be located within the portion of the shaft member. In some embodiments, the structure may be physically coupled to the distal end portion of the shaft member. In some embodiments, the shaft member includes a length along the shaft member extending between the proximal end portion of the shaft member and the distal end portion of the shaft member, the length sufficient to position the proximal end portion of the shaft member at a location outside the patient during a state in which the structure is located at the location within the patient. In some embodiments, the structure may be selectively moveable between a delivery configuration in which the structure is suitably sized to be percutaneously deliverable to the location within the patient, and a deployed configuration in which the structure is sized too large to be percutaneously deliverable to the location within the patient.

In some embodiments, the controller may be configured to determine the second temperature based at least on a predictive model and (a) information related to the first temperature, (b) information related to the second electrical power, (c) information related to the second time period, or a combination of two or all of (a), (b), and (c).

In some embodiments, the first set of conductors of the plurality of conductors may be the second set of conductors of the plurality of conductors. In some embodiments, the first transducer set may be the second transducer set. In some embodiments, each transducer of the plurality of transducers may include a respective one of a plurality of electrodes.

In some embodiments, the first temperature may be a temperature of the portion of the shaft member at the start of the first time period.

In some embodiments, the portion of the shaft member does not include any of the plurality of transducers. In some embodiments, the portion of the shaft member does not include any ablation transducer. In some embodiments, the portion of the shaft member does not include any therapeutic transducer.

Various medical device systems may include combinations and subsets of those summarized above.

According to some embodiments, a medical device system may be summarized as including a structure, a plurality of transducers located on the structure, a shaft member configured to percutaneously deliver the structure to a location within a patient, a plurality of conductors coupled to the plurality of transducers, at least a portion of each conductor of the plurality of conductors located within the shaft member, and a controller operatively coupled to the plurality of transducers and configured to cause delivery of electrical current to the plurality of transducers via the plurality of conductors. According to some embodiments, the shaft member includes a distal end portion and a proximal end portion, and at least part of the shaft member may be sized to be percutaneously deliverable toward the location within the patient distal end portion ahead of the proximal end portion. According to some embodiments, the controller may be configured to cause delivery, via a first set of the plurality of conductors, of a first electrical current signal set to a transducer set of the plurality of transducers, the first electrical current signal set sufficient to cause, if delivered for a first time period, a portion of the shaft member to transition from a first temperature to a steady-state temperature immediately upon conclusion of the first time period, the steady-state temperature determined sufficient to cause thermally-induced tissue cellular damage. In some embodiments, the controller may be configured to cause delivery of the first electrical current signal set to the transducer set for a second time period, the second time period shorter than the first time period, and the delivery of the first electrical current signal set to the transducer set for the second time period being (a) sufficient to cause tissue ablation via the transducer set, and (b) sufficient to cause the portion of the shaft member to transition from the first temperature to a second temperature immediately upon conclusion of the second time period, the second temperature less than the steady-state temperature and determined insufficient to cause thermally-induced tissue cellular damage.

In some embodiments, delivery of the first electrical current signal set to the transducer set, if delivered for a third time period longer than the second time period, may be sufficient to cause the portion of the shaft member to transition from the first temperature to a third temperature, the third temperature determined sufficient to cause thermally-induced tissue cellular damage. In some embodiments, the third time period may be shorter than the first time period. In some embodiments, the third temperature may be sufficient to cause thermally-induced tissue cellular necrosis.

According to some embodiments, the second temperature may be a temperature within a range of 43 to 60 degrees Celsius, inclusive. In some embodiments, the second temperature may be a temperature less than or equal to 48 degrees Celsius, and the second time period may be shorter than or equal to 10 minutes. In some embodiments, the second temperature may be a temperature less than or equal to 60 degrees Celsius, and the second time period may be shorter than or equal to 1 minute. In some embodiments, the first temperature may be an ambient temperature of the portion of the shaft member. In some embodiments, the first temperature may be less than or equal to a temperature of a portion of the patient that the at least part of the shaft member is percutaneously deliverable through.

According to some embodiments, the transducer set is a first transducer set and the controller may be configured to cause particular electrical power to be delivered to at least a second transducer set of the plurality of transducers, the particular electrical power delivered to at least the second transducer set prior to the delivery of the first electrical current signal set to the first transducer set, and wherein the first temperature is a temperature of the portion of the shaft member after the particular electrical power is delivered to at least the second transducer set. In some embodiments, the particular electrical power delivered to at least the second transducer set may be sufficient to cause tissue ablation via the second transducer set.

In some embodiments, the first temperature may be a temperature of the portion of the shaft member prior to the controller causing electrical power to be delivered to any transducer of the plurality of transducers. In some embodiments, the first temperature may be a temperature of the portion of the shaft member prior to the controller causing electrical power to be delivered to any particular transducer of the plurality of transducers to cause the particular transducer to emit energy sufficient for tissue ablation.

In some embodiments, the medical device system may include at least a first temperature sensor configured to sense the first temperature, the second temperature, or both the first temperature and the second temperature. In some embodiments, the first temperature sensor may be located on or in the shaft member. In some embodiments, the distal end portion of the shaft member includes a distal end, and the proximal end portion of the shaft member includes a proximal end, and the first temperature sensor may be located on or in the shaft member at a location closer to the distal end of the shaft member than to the proximal end of the shaft member. In some embodiments, the distal end portion of the shaft member includes a distal end, and the proximal end portion of the shaft member includes a proximal end, and the first temperature sensor may be located on or in the shaft member at a location closer to the proximal end of the shaft member than to the distal end of the shaft member. In some embodiments, the first temperature sensor may be provided at least in part by a first conductor, at least a portion thereof located in the shaft member. In some embodiments, the controller may be configured to determine the first temperature, the second temperature, or both the first temperature and the second temperature based at least on a resistance of at least part of the first conductor.

The shaft member may include at least a first lumen extending between the proximal end portion of the shaft member and the distal end portion of the shaft member, and in some embodiments, the plurality of conductors are located in the first lumen. The shaft member may include at least a first lumen extending between the proximal end portion of the shaft member and the distal end portion of the shaft member, and in some embodiments, the structure may be configured to be delivered through the first lumen as the structure is percutaneously delivered toward the location within the patient. In some embodiments, at least part of each conductor of the plurality of conductors may be located within the portion of the shaft member. In some embodiments, the structure may be physically coupled to the distal end portion of the shaft member. In some embodiments, the shaft member may include a length along the shaft member extending between the proximal end portion of the shaft member and the distal end portion of the shaft member, the length sufficient to position the proximal end portion of the shaft member at a location outside the patient during a state in which the structure is located at the location within the patient. In some embodiments, the structure may be selectively moveable between a delivery configuration in which the structure is suitably sized to be percutaneously deliverable to the location within the patient, and a deployed configuration in which the structure is sized too large to be percutaneously deliverable to the location within the patient.

In some embodiments, the controller may be configured to determine the second temperature based at least on a predictive model and (a) information related to the first temperature, (b) information related to the first electrical current signal set, (c) information related to the second time period, or a combination of two or all of (a), (b), and (c).

In some embodiments, the steady-state temperature may be sufficient to cause thermally-induced tissue cellular necrosis.

In some embodiments, each transducer of the plurality of transducers may include a respective one of a plurality of electrodes.

In some embodiments, the first temperature may be a temperature of the portion of the shaft member at the start of the first time period.

In some embodiments, the portion of the shaft member does not include any of the plurality of transducers. In some embodiments, the portion of the shaft member does not include any ablation transducer. In some embodiments, portion of the shaft member does not include any therapeutic transducer.

Various medical device systems may include combinations and subsets of those summarized above.

According to some embodiments, a medical device system may be summarized as including a structure, a plurality of transducers located on the structure, a shaft member configured to percutaneously deliver the structure to a location within a patient, a plurality of conductors coupled to the plurality of transducers, at least a portion of each conductor of the plurality of conductors located within the shaft member, and a controller operatively coupled to the plurality of transducers and configured to cause delivery of electrical power to the plurality of transducers via the plurality of conductors. The shaft member may include a distal end portion and a proximal end portion, and at least part of the shaft member may be sized to be percutaneous deliverable toward the location within the patient distal end portion ahead of the proximal end portion in some embodiments. In some embodiments, the controller may be configured to cause delivery, via a first set of the plurality of conductors, of first electrical power to a transducer set of the plurality of transducers, the first electrical power sufficient to cause, if delivered for a first time period, a portion of the shaft member to transition from a first temperature to a steady-state temperature immediately upon conclusion of the first time period, the steady-state temperature determined sufficient to cause thermally-induced tissue cellular damage. In some embodiments, the controller may be configured to cause delivery of the first electrical power to the transducer set for a second time period, the second time period shorter than the first time period, and the delivery of the first electrical power to the transducer set for the second time period (a) sufficient to cause tissue ablation via the transducer set, and (b) sufficient to cause the portion of the shaft member to transition from the first temperature to a second temperature immediately upon conclusion of the second time period, the second temperature less than the steady-state temperature and determined insufficient to cause thermally-induced tissue cellular damage.

In some embodiments, delivery of the first electrical power to the transducer set, if delivered for a third time period longer than the second time period, may be sufficient to cause the portion of the shaft member to transition from the first temperature to a third temperature, the third temperature determined sufficient to cause thermally-induced tissue cellular damage. In some embodiments, the third time period may be shorter than the first time period. In some embodiments, the third temperature may be sufficient to cause thermally-induced tissue cellular necrosis.

In some embodiments, the second temperature may be a temperature within a range of 43 to 60 degrees Celsius, inclusive. In some embodiments, the second temperature may be a temperature less than or equal to 48 degrees Celsius, and the second time period may be shorter than or equal to 10 minutes. In some embodiments, the second temperature may be a temperature less than or equal to 60 degrees Celsius, and the second time period may be shorter than or equal to 1 minute. In some embodiments, the first temperature may be an ambient temperature of the portion of the shaft member. In some embodiments, the first temperature may be less than or equal to a temperature of a portion of the patient that the at least part of the shaft member is percutaneously deliverable through.

According to some embodiments, the transducer set is a first transducer set and the controller may be configured to cause particular electrical power to be delivered to at least a second transducer set of the plurality of transducers, the particular electrical power delivered to at least the second transducer set prior to the delivery of the first electrical power to the first transducer set. In some embodiments, the first temperature may be a temperature of the portion of the shaft member after the particular electrical power is delivered to at least the second transducer set. In some embodiments, the particular electrical power delivered to at least the second transducer set may be sufficient to cause tissue ablation via the second transducer set.

According to some embodiments, the first temperature may be a temperature of the portion of the shaft member prior to the controller causing electrical power to be delivered to any transducer of the plurality of transducers. In some embodiments, the first temperature may be a temperature of the portion of the shaft member prior to the controller causing electrical power to be delivered to any particular transducer of the plurality of transducers to cause the particular transducer to emit energy sufficient for tissue ablation.

In some embodiments, the medical device system may include at least a first temperature sensor configured to sense the first temperature, the second temperature, or both the first temperature and the second temperature. In some embodiments, the first temperature sensor may be located on or in the shaft member. In some embodiments, the distal end portion of the shaft member includes a distal end, and the proximal end portion of the shaft member includes a proximal end, and the first temperature sensor may be located on or in the shaft member at a location closer to the distal end of the shaft member than to the proximal end of the shaft member. In some embodiments, the distal end portion of the shaft member includes a distal end, and the proximal end portion of the shaft member includes a proximal end, and the first temperature sensor may be located on or in the shaft member at a location closer to the proximal end of the shaft member than to the distal end of the shaft member. In some embodiments, the first temperature sensor is provided at least in part by a first conductor, at least a portion thereof located in the shaft member, and the controller may be configured to determine the first temperature, the second temperature, or both the first temperature and the second temperature based at least on a resistance of at least part of the first conductor.

The shaft member may include at least a first lumen extending between the proximal end portion of the shaft member and the distal end portion of the shaft member, and wherein the plurality of conductors may be located in the first lumen according to some embodiments. The shaft member may include at least a first lumen extending between the proximal end portion of the shaft member and the distal end portion of the shaft member, and the structure may be configured to be delivered through the first lumen as the structure is percutaneously delivered toward the location within the patient according to some embodiments. In some embodiments, at least part of each conductor of the plurality of conductors may be located within the portion of the shaft member. In some embodiments, the structure may be physically coupled to the distal end portion of the shaft member. In some embodiments, the shaft member may include a length along the shaft member extending between the proximal end portion of the shaft member and the distal end portion of the shaft member, the length sufficient to position the proximal end portion of the shaft member at a location outside the patient during a state in which the structure is located at the location within the patient. In some embodiments, the structure may be selectively moveable between a delivery configuration in which the structure is suitably sized to be percutaneously deliverable to the location within the patient, and a deployed configuration in which the structure is sized too large to be percutaneously deliverable to the location within the patient.

According to some embodiments, the controller may be configured to determine the second temperature based at least on a predictive model and (a) information related to the first temperature, (b) information related to the first electrical power, (c) information related to the second time period, or a combination of two or all of (a), (b), and (c).

In some embodiments, the steady-state temperature may be sufficient to cause thermally-induced tissue cellular necrosis.

In some embodiments, each transducer of the plurality of transducers may include a respective one of a plurality of electrodes.

In some embodiments, the first temperature may be a temperature of the portion of the shaft member at the start of the first time period.

In some embodiments, the portion of the shaft member does not include any of the plurality of transducers. In some embodiments, the portion of the shaft member does not include any ablation transducer. In some embodiments, the portion of the shaft member does not include any therapeutic transducer.

Various medical device systems may include combinations and subsets of those summarized above.

According to some embodiments, a medical device system may be summarized as including a structure, one or more transducers located on the structure, a shaft member configured to percutaneously deliver the structure to a location within a patient, one or more conductors coupled to the one or more transducers, at least a portion of each conductor of the one or more conductors located within the shaft member, and a controller operatively coupled to the one or more transducers via the one or more conductors and configured to cause delivery of electrical current to the one or more transducers via the one or more conductors. The shaft member may include a distal end portion and a proximal end portion, and at least part of the shaft member may be sized to be percutaneously deliverable toward the location within the patient distal end portion ahead of the proximal end portion according to some embodiments. According to some embodiments, an electrical current-based limit may be defined as a first value derivable, according to a particular relationship, from each electrical current signal of a first electrical current signal set that, if delivered via a first set of the one or more conductors to a first transducer set of the one or more transducers for a first time period, is sufficient to cause a portion of the shaft member to transition from a first temperature to a first steady-state temperature immediately upon conclusion of the first time period, the first steady-state temperature determined insufficient to cause thermally-induced tissue cellular damage. In some embodiments, the controller may be configured to cause delivery, via a second set of the one or more conductors, of a second electrical current signal set to a second transducer set of the one or more transducers for a second time period. In some embodiments, a second value derivable, according to the particular relationship, from each electrical current signal of the second electrical current signal set may be greater than the electrical current-based limit. In some embodiments, the second time period may be shorter than the first time period, and the delivery of the second electrical current signal set to the second transducer set for the second time period may be (a) sufficient to cause tissue ablation via the second transducer set, and (b) sufficient to cause the portion of the shaft member to transition from the first temperature to a second temperature immediately upon conclusion of the second time period, the second temperature less than or equal to the first steady-state temperature.

According to some embodiments, the particular relationship may include a summation of a square of a root mean square (RMS) value of each electrical current signal in an electrical current signal set.

In some embodiments, the controller may be configured to cause delivery of each electrical current signal of the second electrical current signal set to each transducer in the second transducer set via a respective conductor of the one or more conductors. In some embodiments, the one or more conductors may include a plurality of conductors. In some embodiments, the one or more transducers may include a plurality of transducers. In some embodiments, the second transducer set may at least two transducers of the plurality of transducers. In some embodiments, the first set of the one or more conductors may be the second set of the one or more conductors. In some embodiments, the first transducer set may be the second transducer set.

According to some embodiments, the second electrical current signal set, if delivered to the second transducer set for a third time period longer than the second time period, may be sufficient to cause the portion of the shaft member to transition from the first temperature to a third temperature, the third temperature determined sufficient to cause thermally-induced tissue cellular damage. In some embodiments, the third temperature may be a steady-state temperature. In some embodiments, the third temperature may be greater than the first steady-state temperature. In some embodiments, the third time period may be shorter than the first time period.

In some embodiments, the second temperature may be a temperature within a range of 43 to 60 degrees Celsius, inclusive. In some embodiments, the second temperature may be a temperature less than or equal to 48 degrees Celsius, and the second time period may be shorter than or equal to 10 minutes. In some embodiments, the second temperature may be a temperature less than or equal to 60 degrees Celsius, and the second time period may be shorter than or equal to 1 minute. In some embodiments, the first temperature may be an ambient temperature of the portion of the shaft member. In some embodiments, the first temperature may be a temperature that is less than or equal to a temperature of a portion of the patient that the at least part of the shaft member is percutaneously deliverable through.

In some embodiments, the controller may be configured to cause electrical power to be delivered to at least a third transducer set of the one or more transducers, the electrical power delivered to at least the third transducer set prior to the delivery of the second electrical current signal set to the second transducer set. In some embodiments, the first temperature may be a temperature of the portion of the shaft member after the electrical power is delivered to at least the third transducer set. In some embodiments, the electrical power delivered to at least the third transducer set may be sufficient to cause tissue ablation via the third transducer set.

In some embodiments, the first temperature may be a temperature of the portion of the shaft member prior to the controller causing electrical power to be delivered to any transducer of the one or more transducers. In some embodiments, the first temperature may be a temperature of the portion of the shaft member prior to the controller causing electrical power to be delivered to any particular transducer of the one or more transducers to cause the particular transducer to emit energy sufficient for tissue ablation.

In some embodiments, the medical device system may include at least a first temperature sensor configured to sense the first temperature, the second temperature, or both the first temperature and the second temperature. In some embodiments, the first temperature sensor may be located on or in the shaft member. In some embodiments, the distal end portion of the shaft member includes a distal end, and the proximal end portion of the shaft member includes a proximal end, and the first temperature sensor may be located on or in the shaft member at a location closer to the distal end of the shaft member than to the proximal end of the shaft member. In some embodiments, the distal end portion of the shaft member includes a distal end, and the proximal end portion of the shaft member includes a proximal end, and the first temperature sensor may be located on or in the shaft member at a location closer to the proximal end of the shaft member than to the distal end of the shaft member. In some embodiments, the first temperature sensor may be provided at least in part by a first conductor, at least a portion thereof included in the shaft member, and the controller may be configured to determine the first temperature, the second temperature, or both the first temperature and the second temperature based at least on a resistance of at least part of the first conductor.

In some embodiments, the shaft member may include at least a first lumen extending between the proximal end portion of the shaft member and the distal end portion of the shaft member, and the one or more conductors may be located in the first lumen. In some embodiments, the shaft member may include at least a first lumen extending between the proximal end portion of the shaft member and the distal end portion of the shaft member, and the structure may be configured to be delivered through the first lumen as the structure is percutaneously delivered toward the location within the patient. In some embodiments, at least part of each conductor of the one or more conductors may be located within the portion of the shaft member. In some embodiments, the structure may be physically coupled to the distal end portion of the shaft member. In some embodiments, the shaft member may include a length along the shaft member extending between the proximal end portion of the shaft member and the distal end portion of the shaft member, the length sufficient to position the proximal end portion of the shaft member at a location outside the patient during a state in which the structure is located at the location within the patient. In some embodiments, the structure may be selectively moveable between a delivery configuration in which the structure is suitably sized to be percutaneously deliverable to the location within the patient, and a deployed configuration in which the structure is sized too large to be percutaneously deliverable to the location within the patient.

In some embodiments, the controller may be configured to determine the second temperature based at least on a predictive model and (a) information related to the first temperature, (b) information related to the second electrical current signal set, (c) information related to the second time period, or a combination of two or all of (a), (b), and (c).

In some embodiments, each transducer of the one or more transducers may include a respective electrode. In some embodiments, the first temperature may be a temperature of the portion of the shaft member at the start of the first time period. In some embodiments, the portion of the shaft member does not include any of the one or more transducers. In some embodiments, the portion of the shaft member does not include any ablation transducer. In some embodiments, the portion of the shaft member does not include any therapeutic transducer.

Various medical device systems may include combinations and subsets of those summarized above.

According to some embodiments, a medical device system may be summarized as including a structure, a shaft member configured to percutaneously deliver the structure to a location within a patient, the shaft member including a distal end portion and a proximal end portion, at least part of the shaft member sized to be percutaneously deliverable toward the location within the patient distal end portion ahead of the proximal end portion. In some embodiments, the medical device system may include an input-output device system including a plurality of transducers located on the structure and a plurality of conductors, each conductor of the plurality of conductors coupled to a respective transducer of the plurality of transducers, and at least a portion of each conductor of the plurality of conductors located within the shaft member. In some embodiments, the medical device system may include a data processing device system communicatively connected to the input-output device system including being communicatively connected to the plurality of transducers via the plurality of conductors, and a memory device system communicatively connected to the data processing device system and storing a program executable by the data processing device system. In some embodiments, the program may include temperature determination instructions configured to determine a temperature of at least a portion of the shaft member. In some embodiments, the program may include transducer determination instructions configured to determine a particular number X of transducers permitted to cause concurrent tissue ablation based at least on the determined temperature. In some embodiments, the program may include transducer activation instructions configured to cause a first electrical current signal set to be delivered via a first set of conductors of the plurality of conductors to a group of X corresponding transducers of the plurality of transducers based on the determination of the number X of transducers permitted to cause concurrent tissue ablation. In some embodiments, the delivered first electrical current signal set may be sufficient to cause tissue ablation via the group of X corresponding transducers of the plurality of transducers.

In some embodiments, the transducer activation instructions may be configured to cause the first electrical current signal set to be delivered via the first set of conductors of the plurality of conductors to the group of X corresponding transducers of the plurality of transducers to cause concurrent tissue ablation.

In some embodiments, the program may include transducer selection instructions configured to identify Y transducers of the plurality of transducers to be activated to cause tissue ablation, wherein Y is greater than X. In some embodiments, the transducer activation instructions may be configured to cause the first electrical current signal set to be concurrently delivered to a smaller number of transducers than the number of transducers identified according to the transducer selection instructions. In some embodiments, the transducer activation instructions may be configured to cause a second electrical current signal set to be delivered via a second set of conductors of the plurality of the conductors to at least some of the Y transducers after completion of the delivery of the first set electrical current signal set via the first set of conductors of the plurality of conductors to the group of X corresponding transducers of the plurality of transducers. In some embodiments, the delivered second electrical current signal set may be sufficient to cause tissue ablation via the at least some of the Y transducers, and the at least some of the Y transducers may include at least one transducer not included in the group of X corresponding transducers of the plurality of transducers. In some embodiments, the at least some of the Y transducers may not include any transducer included in the group of X corresponding transducers of the plurality of transducers. In some embodiments, the transducer activation instructions may be configured to cause the second electrical current signal set to be delivered via the second set of conductors of the plurality of conductors to the at least some of the Y transducers to cause concurrent tissue ablation. In some embodiments, the particular number X of transducers may be less than a total number of the plurality of transducers.

In some embodiments, the temperature may be determined to be an ambient temperature of the portion of the shaft member. In some embodiments, the temperature may be determined to be less than or equal to a temperature of a portion of the patient that the at least part of the shaft member is percutaneously deliverable through.

In some embodiments, the group of X corresponding transducers of the plurality of transducers is a first transducer set, and the transducer activation instructions may be configured to cause electrical power to be delivered to at least a second transducer set of the plurality of transducers, the electrical power delivered to at least the second transducer set prior to the delivery of the first electrical current signal set to the first transducer set. In some embodiments, the temperature determination instructions may be configured to determine the temperature of the portion of the shaft member at least after the electrical power has been delivered to at least the second transducer set. In some embodiments, the electrical power delivered to at least the second transducer set may be sufficient to cause tissue ablation via the second transducer set.

In some embodiments, the temperature determination instructions may be configured to determine the temperature of the portion of the shaft member at least prior to the data processing device system causing electrical power to be delivered to any transducer of the plurality of transducers. In some embodiments, the temperature determination instructions may be configured to determine the temperature of the portion of the shaft member at least prior to the data processing device system causing electrical power to be delivered to any particular transducer of the plurality of transducers to cause the particular transducer to emit energy sufficient for tissue ablation.

In some embodiments, the transducer determination instructions may be configured to determine the particular number X of transducers permitted to cause concurrent ablation to cause a temperature of a particular portion of the shaft member to remain at or below the determined temperature. In some embodiments, the transducer determination instructions may be configured to determine the particular number X of transducers permitted to cause concurrent ablation to cause a temperature of a particular portion of the shaft member to remain below a particular temperature determined sufficient to cause thermally induced tissue cellular damage via the particular portion of the shaft member.

In some embodiments, the medical device system may include at least a first temperature sensor included in the input-output device system and configured to sense a particular characteristic. In some embodiments, the temperature determination instructions may be configured to determine the temperature based at least on the sensed particular characteristic. In some embodiments, the first sensor may be located on or in the shaft member. In some embodiments, the distal end portion of the shaft member includes a distal end, and the proximal end portion of the shaft member includes a proximal end, and the first sensor may be located on or in the shaft member at a location closer to the distal end of the shaft member than to the proximal end of the shaft member. In some embodiments, the distal end portion of the shaft member includes a distal end, and the proximal end portion of the shaft member includes a proximal end, and the first sensor may be located on or in the shaft member at a location closer to the proximal end of the shaft member than to the distal end of the shaft member. In some embodiments, the first temperature sensor may be provided at least in part by a first conductor, at least a portion thereof included in the shaft member. In some embodiments, the temperature determination instructions may be configured to determine the temperature of the portion of the shaft member based at least on a resistance of at least part of the first conductor.

In some embodiments, the shaft member may include at least a first lumen extending between the proximal end portion of the shaft member and the distal end portion of the shaft member and the plurality of conductors may be located in the first lumen. In some embodiments, at least part of each conductor of the plurality of conductors may be located within the portion of the shaft member. In some embodiments, the shaft member may include at least a first lumen extending between the proximal end portion of the shaft member and the distal end portion of the shaft member, and the structure may be configured to be delivered through the first lumen as the structure is percutaneously delivered toward the location within the patient. In some embodiments, the structure may be physically coupled to the distal end portion of the shaft member. In some embodiments, the shaft member may include a length along the shaft member extending between the proximal end portion of the shaft member and the distal end portion of the shaft member, the length sufficient to position the proximal end portion of the shaft member at a location outside the patient during a state in which the structure is located at the location within the patient. In some embodiments, the structure may be selectively moveable between a delivery configuration in which the structure is suitably sized to be percutaneously deliverable to the location within the patient, and a deployed configuration in which the structure is sized too large to be percutaneously deliverable to the location within the patient.

In some embodiments, the temperature determination instructions may be configured to determine the temperature of the portion of the shaft member based at least on a predictive model.

In some embodiments, each transducer of the plurality of transducers may include a respective one of a plurality of electrodes. In some embodiments, the portion of the shaft member does not include any of the plurality of transducers. In some embodiments, the portion of the shaft member does not include any ablation transducer. In some embodiments, the portion of the shaft member does not include any therapeutic transducer.

Various medical device systems may include combinations and subsets of those summarized above.

According to some embodiments, a medical device system may be summarized as including a structure, and a shaft member configured to percutaneously deliver the structure to a location within a patient, the shaft member including a distal end portion and a proximal end portion, at least part of the shaft member sized to be percutaneously deliverable toward the location within the patient distal end portion ahead of the proximal end portion. In some embodiments, the medical device system may include an input-output device system including a transducer set located on the structure and a conductor set, each conductor in the conductor set coupled to a respective transducer in the transducer set, and at least a portion of each conductor in the conductor set located within the shaft member. In some embodiments, the medical device system may include a data processing device system communicatively connected to the input-output device system including being communicatively connected to the transducer set via the conductor set, and a memory device system communicatively connected to the data processing device system and storing a program executable by the data processing device system. In some embodiments, the program may include temperature determination instructions configured to cause the data processing device system to determine a temperature of at least a portion of the shaft member. In some embodiments, the program may include temperature comparison instructions configured to cause the data processing device system to compare the determined temperature of the portion of the shaft member with a provided temperature threshold. In some embodiments, the program may include transducer activations instructions configured to cause at least a first electrical current signal set to be delivered, via at least one conductor in the conductor set, to at least one transducer in the transducer set for at least a first time period. In some embodiments, the delivered at least the first electrical current signal set may be sufficient to cause tissue ablation via the transducer set. In some embodiments, the transducer activation instructions may include instructions configured to delay the delivery of the at least the first electrical current signal set in a case where the comparison of the determined temperature of the portion of the shaft member with the provided temperature threshold indicates that the determined temperature of the portion of the shaft member exceeds the provided temperature threshold.

In some embodiments, the provided temperature threshold may indicate a particular temperature of the portion of the shaft member, the particular temperature insufficient to cause thermally-induced tissue cellular damage, but if exceeded, is determined to cause thermally-induced tissue cellular damage. In some embodiments, the determined temperature may be a predicted future temperature of the portion of the shaft member at some particular time during the first period if the first electrical current signal set was to be delivered, absent the delay, via the at least one conductor in the conductor set to the at least one transducer in the transducer set for the first time period.

In some embodiments, the program may include temperature threshold determination instructions configured to cause the data processing device system to determine the temperature threshold as a particular temperature of the portion of the shaft member at some particular time during the first period if the first electrical current signal set was to be delivered, absent the delay, via the at least one conductor in the conductor set to the at least one transducer in the transducer set for the first time period, the particular temperature insufficient to cause thermally-induced tissue cellular damage, but if exceeded, is determined to cause thermally-induced tissue cellular damage.

In some embodiments, the program may include temperature threshold determination instructions configured to cause the data processing device system to determine the temperature threshold as a particular temperature of the portion of the shaft member at the start of the first period if the first electrical current signal set was to be delivered, absent the delay, via the at least one conductor in the conductor set to the at least one transducer in the transducer set for the first time period, the particular temperature insufficient to cause the portion of the shaft to heat sufficiently to cause thermally-induced tissue cellular damage throughout the first time period, but, if exceeded, is determined to cause the portion of the shaft member to heat sufficiently at some point within first time period to cause thermally-induced tissue cellular damage.

In some embodiments, the determined temperature may be a present temperature of the portion of the shaft member at the start of the first time period, if the first electrical current signal set was to be delivered, absent the delay, via the at least one conductor in the conductor set to the at least one transducer in the transducer set for the first time period. In some embodiments, the provided temperature threshold may be a particular temperature of the portion of the shaft member that is at least $\Delta T_{TP1}$ degrees Celsius below a predetermined temperature threshold that, if exceeded, is predetermined to cause thermally-induced tissue cellular damage. In some embodiments $\Delta T_{TP1}$ is a temperature increase that would occur if the first electrical current signal set was to be delivered, absent the delay, via the at least one conductor in the conductor set to the at least one transducer in the transducer set for the first time period.

In some embodiments, the temperature threshold may be provided as a predetermined value stored in the memory device system.

In some embodiments, the program may include temperature threshold determination instructions configured to determine the temperature threshold based at least on the determined temperature. In some embodiments, the determined temperature may indicate a particular temperature of the portion of the shaft member at the start of the first time period, absent the delay. In some embodiments, the medical device system may further include at least a first sensor (e.g., included in the input-output device system) configured to provide, to the data processing device system, data responsive to the temperature of the portion of the shaft member. In various embodiments, the temperature determination instructions may be configured to determine the temperature of the portion of the shaft member based on the data. In some embodiments, the first sensor may be located on or in the shaft member. In some embodiments, the distal end portion of the shaft member includes a distal end, and the proximal end portion of the shaft member includes a proximal end, and the first sensor may be located on or in the shaft member at a location closer to the distal end of the shaft member than to the proximal end of the shaft member. In some embodiments, the distal end portion of the shaft member includes a distal end, and the proximal end portion of the shaft member includes a proximal end, and the first sensor may be located on or in the shaft member at a location closer to the proximal end of the shaft member than to the distal end of the shaft member. In some embodiments, the first sensor may be provided at least in part by a first conductor, at least a portion thereof included in the shaft member, and the temperature determination instructions may be configured to determine the temperature of the portion of the shaft member based at least on a resistance of at least part of the first conductor. In some embodiments, the temperature determination instructions may be configured to determine the temperature of the portion of the shaft member based at least on a predictive model.

In some embodiments, the program may include temperature threshold determination instructions configured to determine the temperature threshold based at least on a particular temperature of the portion of the shaft member at the start of the first time period, absent the delay. In some embodiments, the program may include temperature threshold determination instructions configured to determine the temperature threshold based at least on a provided temperature limit, the provided temperature limit indicating a particular temperature of the portion of the shaft member, the particular temperature insufficient to cause thermally-induced tissue cellular damage, but, if exceeded, is predetermined to cause thermally-induced tissue cellular damage. In some embodiments, the program may include temperature threshold determination instructions configured to determine the temperature threshold based at least on a duration of the first time period.

In some embodiments, the program may include power determination instructions configured to determine particular data responsive to power dissipation associated with at least the delivery of the at least the first electrical current signal set via the at least one conductor in the conductor set during the first time period. In some embodiments, the program may include temperature threshold determination instructions configured to determine the temperature threshold based at least on the particular data.

In some embodiments, the portion of the shaft member does not include any transducer of the transducer set. In some embodiments, the portion of the shaft member does not include any ablation transducer. In some embodiments, the portion of the shaft member does not include any therapeutic transducer.

In some embodiments, the delay may have a duration $T_D$, and during the duration $T_D$, no electrical current or electrical power may be delivered by any conductor in the conductor set. In some embodiments, the delay may have a duration $T_D$, and during the duration $T_D$, no electrical current or electrical power may be delivered by any conductor located in the shaft member. In some embodiments, the delay may have a duration $T_D$, and during the duration $T_D$, no electrical current or electrical power may be delivered by any conductor in the conductor set to any particular transducer in the transducer set to cause the particular transducer to transmit energy sufficient to cause tissue ablation.

In some embodiments, the shaft member includes at least a first lumen extending between the proximal end portion of the shaft member and the distal end portion of the shaft member, and the plurality of conductors may be located in the first lumen. In some embodiments, at least part of each conductor of the plurality of conductors may be located within the portion of the shaft member.

In some embodiments, the shaft member includes at least a first lumen extending between the proximal end portion of the shaft member and the distal end portion of the shaft member, and the structure may be configured to be delivered through the first lumen as the structure is percutaneously delivered toward the location within the patient.

In some embodiments, the structure may be physically coupled to the distal end portion of the shaft member. In some embodiments, the shaft member may include a length along the shaft member extending between the proximal end portion of the shaft member and the distal end portion of the shaft member, the length sufficient to position the proximal end portion of the shaft member at a location outside the patient during a state in which the structure is located at the location within the patient. In some embodiments, the structure may be selectively moveable between a delivery configuration in which the structure is suitably sized to be percutaneously deliverable to the location within the patient, and a deployed configuration in which the structure is sized too large to be percutaneously deliverable to the location within the patient.

Various medical device systems may include combinations and subsets of those summarized above. Various embodiments of the present invention may include systems, devices, or machines that are or include combinations or subsets of any one or more of the systems, devices, or machines and associated features thereof described herein.

Further, all or part of any one or more of the systems, devices, or machines discussed herein or combinations or sub-combinations thereof may implement or execute all or part of any one or more of the processes or methods discussed herein or combinations or sub-combinations thereof.

Any of the features of all or part of any one or more of the methods or processes discussed herein may be combined with any of the other features of all or part of any one or more of the methods and processes discussed herein. In addition, a computer program product may be provided that comprises program code portions for performing some or all of any one or more of the methods or processes and associated features thereof described herein, when the computer program product is executed by a computer or other computing device or device system. Such a computer program product may be stored on one or more computer-readable storage mediums, also referred to as one or more computer-readable data storage mediums.

In some embodiments, each of any of one or more of the computer-readable data storage medium systems (also referred to as processor-accessible memory device systems) described herein is a non-transitory computer-readable (or processor-accessible) data storage medium system (or memory device system) including or consisting of one or more non-transitory computer-readable (or processor-accessible) storage mediums (or memory devices) storing the respective program(s) which may configure a data processing device system to execute some or all of any of one or more of the methods or processes described herein.

Further, any of one or more of the methods or processes and associated features thereof discussed herein may be implemented or executed by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
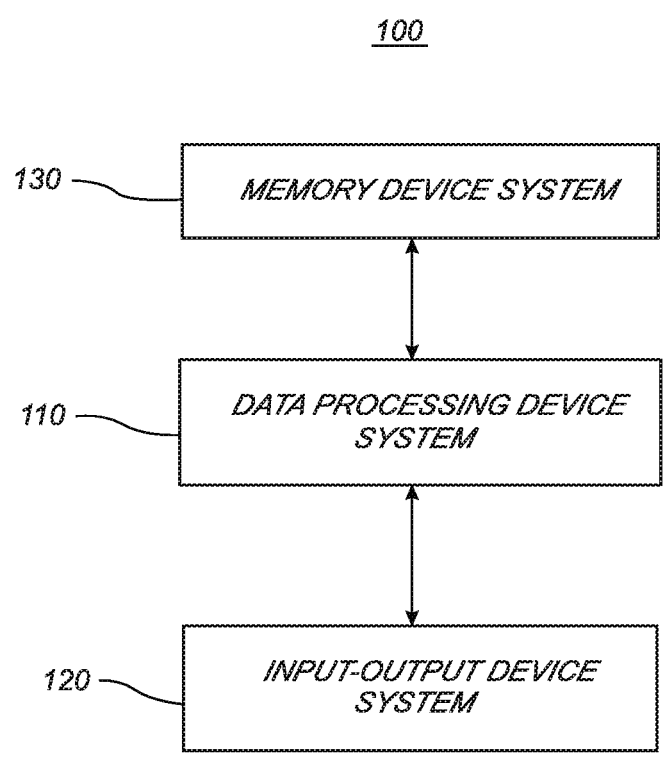
FIG. 1 is a schematic representation of a medical device system according to various example embodiments, where the medical device system may include a data processing device system, an input-output device system, and a memory device system, according to some embodiments.

Some embodiments of the present invention pertain at least to medical systems or medical device systems that include at least an elongate shaft member (also referred to a carrier member) employable to deliver a structure and one or more transducers located on the structure to a desired location within the body of a patient. In some embodiments, such a structure may include a plurality of elongate members. In some embodiments, such a structure is manipulable to change size, shape, or both size and shape thereof. In various embodiments, such a structure is selectively moveable between a delivery configuration, in which the structure is suitably sized to be percutaneously or intravascularly deliverable to a bodily cavity, and a deployed or expanded configuration, in which the structure is sized too large to be percutaneously or intravascularly deliverable to the bodily cavity. In some embodiments, medical device systems may include various elongate members, some particular portions (e.g., first particular portions) of each of the elongate members forming a structure that is selectively moveable between a first configuration (e.g. a delivery configuration), in which the structure or the some particular portions are suitably sized to be percutaneously or intravascularly deliverable to a bodily cavity, and a second configuration, in which the structure or the some particular portions are sized too large to be percutaneously or intravascularly deliverable to the bodily cavity. In some embodiments, transducer sets (e.g., electrode sets) are located on the first particular portions of at least some of the elongate members. According to some embodiments, at least some of the transducers may be selectively operable to transmit energy (e.g., energy sufficient to ablate tissue). In some embodiments, each of the first particular portions may be provided by respective of one of a plurality of flexible circuit strip portions.

In some embodiments, the various elongate members include portions (e.g., second particular portions) other than the first particular portions described above. In some embodiments, each of the second particular portions of the various elongate members may be arranged within the shaft member. As discussed in more detail below, the second particular portions of the various elongate members may provide various electrical conductors (herein referred to as "conductors") that are in electrical communication with various ones of the transducers that are deliverable via the shaft member to a desired location within the body of a patient. In some embodiments, various conductors, a portion of each located with the shaft member, and which are distinct from the first particular portions of the elongate members are arranged in electrical communication with various ones of the transducers that are deliverable via the shaft member to a desired location within the body of a patient. In some embodiments, each of the second particular portions may be provided by respective of one of a plurality of flexible circuit strip portions.

In the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects. In addition, unless otherwise explicitly noted or required by context, the word "subset" is intended to mean a set having the same elements as or fewer elements than the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least on A' includes A as well as the possibility of one or more other additional elements besides A. In the same manner, the phrase 'based on A' includes A, as well as the possibility of one or more other additional elements besides A. However, the phrase 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, or device system resides across different housings. The word "device" may equivalently be referred to as a "device system" in some embodiments.

Further, the phrase "in response to" may be used in this disclosure. For example, this phrase may be used where an event A occurs in response to the occurrence of an event B. In this regard, such phrase includes, for example, that at least the occurrence of the event B causes or triggers the event A.

In some embodiments, the term "adjacent", the term "proximate", and the like refer at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refer to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", and the like additionally or alternatively refer to at least a sufficient closeness between the objects defined as adjacent, proximate, and the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments.

The phrase "physically coupled" is intended to include, in some embodiments, a coupling between two objects that may restrict some form of movement (e.g., translation or rotation or both translation and rotation) therebetween. In some embodiments, the two objects physically contact each other at least in one state of the physical coupling between the two objects. In some embodiments, the two objects do not directly physically contact each other at least in one state of the physical coupling between the two objects (e.g., a coupler or other coupling member positioned between the two objects to couple them together). The phrase "rotationally coupled" is intended to include, in some embodiments, a coupling between two objects that allows for at least some rotational movement between the two objects. The phrase "translationally coupled" is intended to include, in some embodiments, a coupling between two objects that allows for some form of translational movement between the two objects. The phrases "fixedly coupled", "permanently coupled", and the like, are intended to include, in some embodiments, a secure coupling between two objects that, in some embodiments, does not involve or include a mechanism configured to release the coupling of the two objects. The phrases "removably coupled", "detachably coupled", and the like, are intended to include, in some embodiments, a coupling between two objects that, in some embodiments, allows such coupling to be repeatedly disengaged and re-engaged without damaging the coupling (if a distinct coupling mechanism exists, e.g., in contrast to an interference fit that relies on friction), without damaging either or both of the objects, or without damaging the coupling (if a distinct coupling mechanism exists) and without damaging either or both of the objects. The phrase "operatively coupled" is intended to include, for example, a coupling between two objects that transmits force, energy, information, or other influence at least from one of the two objects to the other of the two objects. An operative coupling does not exclude the possibility of a physical or fixed coupling in addition to the operative coupling. Unless otherwise explicitly noted or required by context, for any connection or coupling, direct or indirect, between components, devices, or other physical objects described herein, different embodiments include different ones of the above-described coupling types for such components, devices, or other physical objects. For example, unless otherwise explicitly noted or required by context, if a first physical object is shown in the figures or described in this text as being connected or coupled, directly or indirectly, to a second physical object, some embodiments will have the first physical object fixedly coupled to the second physical object; other embodiments will have the first physical object rotationally coupled to the second physical object; other embodiments will have the first physical object translationally coupled to the second physical object; other embodiments will have the first physical object permanently coupled to the second physical object; other embodiments will have the first physical object removably or detachably coupled to the second physical object; other embodiments will have the first physical object not fixedly or permanently coupled to the second physical object while having the first physical object physically coupled to the second physical object; other embodiments will have the first physical object not physically coupled or fixedly coupled to the second physical object, but will have the first physical object operatively coupled to the second physical object; etc. The phrase "electrically coupled" or "electrically connected" as used in this disclosure refer to a transfer of electrical energy from one circuit segment to another. For example, a conductor may be electrically coupled or electrically connected to a transducer to transfer electrical energy to or from the transducer.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In some embodiments, the word "fluid" may include fluid that is not inherent to the bodily cavity, such as saline or other fluid that might be artificially introduced into the bodily cavity. In some embodiments, the word "fluid" may include a fluid that may be artificially introduced into the bodily cavity without the fluid coming into direct contact with tissue or a naturally occurring bodily fluid (e.g., a fluid employed in various cryogenic or other balloon-based ablation procedures). In the case of cardiac applications, fluid such as blood will flow into and out of various intra-cardiac cavities (e.g., a left atrium or right atrium).

The phrase "bodily opening" as used in this disclosure should be understood to include a naturally occurring bodily opening or channel or lumen within a patient; a bodily opening or channel or lumen within a patient formed by an instrument or tool using techniques that may include, but are not limited to, mechanical, thermal, electrical, chemical, and exposure or illumination techniques; a bodily opening or channel or lumen within a patient formed by trauma to a body; or various combinations of one or more of the above or other bodily openings. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body of a patient. The bodily cavity may be a cavity provided in a bodily organ (e.g., an intra-cardiac cavity or chamber of a heart). A bodily opening may be provided as a passageway to a bodily cavity in some embodiments. A bodily cavity may be provided by a bodily opening in some embodiments. The word "patient" as used in this disclosure should be understood to be one who is to receive medical attention, care, or treatment. In various embodiments, the patient may be a mammalian entity. In various embodiments, the patient may be a human entity.

The word "tissue" may be used in this disclosure, and tissue may include non-fluidic tissue and fluidic tissue. Non-fluidic tissue generally (or predominantly) has solid-like properties, such as tissue that forms a surface of a body or a surface within a bodily cavity, a surface of an anatomical feature or a surface of a feature associated with a bodily opening positioned in fluid communication with the bodily cavity. Non-fluidic tissue may include part or all of a tissue wall or membrane that defines a surface of the bodily cavity. In this regard, the tissue may form an interior surface of the cavity that at least partially surrounds a fluid within the cavity. In the case of cardiac applications, non-fluidic tissue may include tissue used to form an interior surface of an intra-cardiac cavity such as a left atrium or right atrium. Fluidic tissue, on the other hand, generally (or predominantly) has fluid-like properties (as compared to solid-like properties). An example of fluidic tissue is blood. In this regard, it should be noted that fluidic tissue may have some solid-like component(s) (e.g., fluidic tissue may include solid-like components), and non-fluidic tissue may have some fluid-like component(s) (e.g., non-fluidic tissue may include fluidic tissue within it). Unless otherwise explicitly noted or required by context, the word "tissue" should include non-fluidic tissue and fluidic tissue. However, some contexts where the word "tissue" would not include fluidic tissue are when tissue ablation is discussed, and ablation of fluidic tissue could be undesired, for example, as it may cause undesired coagulum. In various embodiments, non-fluidic tissue does not include excised tissue.

The word "ablation" as used in this disclosure should be understood to include any disruption to certain properties of tissue. Most commonly, the disruption is to the electrical conductivity of tissue and may be achieved by heating, which may be generated with resistive or radio-frequency (RF) techniques for example. Other properties of tissue, such as mechanical or chemical, and other means of disruption, such as optical or the use of cryogenic fluids are included when the term "ablation" is used. In some embodiments, electroporation techniques are included when the term "ablation" is used. In some embodiments, ablative power levels may be within the range of 3 W to 5 W (as compared, e.g., to a non-tissue-ablative power level range of 50 mW to 200 mW that may be used for typical impedance determinations). In some embodiments, ratios of employed ablative power levels to employed non-tissue-ablative power levels (e.g., used for typical impedance determinations) may be at least equal to or greater than 50:1 in various embodiments; at least greater than 60:1 in some embodiments; at least greater than 80:1 in other various embodiments; and at least greater than 100:1 in yet other embodiments. In some embodiments, systems are configured to perform ablation of non-fluidic tissue while avoiding the delivery of excessive energy to fluidic tissue because energy that is sufficient to ablate non-fluidic tissue may also impact fluidic tissue in some circumstances. For example, energy that is sufficient to ablate non-fluidic tissue, in some circumstances, may cause blood (an example of fluidic tissue) to coagulate. In these and other embodiments where ablative energy transferred to fluidic tissue is not desired, it should be understood that any statement or reference to the 'ablation of tissue' or the like in these contexts is intended to refer to ablation of non-fluidic tissue, as opposed to ablation of fluidic tissue.

The term "transducer" as used in this disclosure should be interpreted broadly as any device capable, for example, of distinguishing between fluid and non-fluidic tissue, sensing temperature, creating heat, ablating tissue and measuring electrical activity of a tissue surface, stimulating tissue or any combination thereof. A transducer that at least interacts or is configured to interact with tissue (fluidic or non-fluidic) may be referred to as a therapeutic transducer in some embodiments. A transducer that at least ablates or is configured to ablate tissue may be referred to as an ablation transducer in some embodiments. A transducer may convert input energy of one form into output energy of another form. Without limitation, a transducer may include an electrode, and references to a "transducer" herein may be replaced with "electrode" according to some embodiments. Without limitation, a transducer may include an electrode or a sensing device, or both an electrode and a sensing device. An electrode, in some embodiments, may be configured at least as a sensing device. An electrode, in some embodiments, may be configured at least as a therapy delivering device (e.g., an ablative energy delivering device). In some embodiments, an electrode may be configured at least as a sensing device and a therapy delivering device. Because a transducer may include an electrode according to various embodiments, any reference herein to a transducer may also imply a reference to an electrode, or vice versa. A transducer may be constructed from several parts, which may be discrete components or may be integrally formed. In some embodiments, an ablative element configured to apply energy sufficient for tissue ablation may be provided at least in part by a transducer, and a transducer including such an ablative element may be referred to as an ablation transducer.

The term "activation" and related terms, at least when used in the context of activating a particular function of one or more transducers or electrodes, such as those disclosed herein, should be interpreted broadly as making active the particular function. Particular functions may include, but are not limited to, tissue ablation, sensing electrophysiological activity, sensing temperature, and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. In some embodiments, activation of a tissue ablation function of a particular electrode is initiated by causing energy from an energy source device system to be delivered to the particular electrode, the energy sufficient for tissue ablation. In some embodiments, activation of a tissue ablation function of a particular electrode is initiated by causing energy sufficient for tissue ablation to be transmitted by the particular electrode. Alternatively, in some embodiments, the activation may be deemed to be initiated when the particular transducer or particular electrode causes tissue that is to be ablated to reach or acquire a temperature sufficient for ablation of the tissue, which may be due to the energy provided by the energy source device system or due to the energy transmitted by the particular transducer or electrode. In some embodiments, the activation may last for a duration concluding when the ablation function is no longer active, such as when energy sufficient for the tissue ablation is no longer provided to, or transmitted by, the particular transducer or particular electrode. Alternatively, in some embodiments, the activation period may be deemed to be concluded when the tissue that is being ablated has a temperature below that sufficient for ablation of the tissue, which may be due to a reduction or cessation of the energy provided by the energy source device system or transmitted by the particular transducer or electrode. In some contexts, however, the word "activation" may merely refer to the initiation of the activating of a particular function, as opposed to referring to both the initiation of the activating of the particular function and the subsequent duration in which the particular function is active. In these contexts, the phrase or a phrase similar to "activation initiation" may be used. For example, in some embodiments activation initiation may cause initiation of a transmission of energy (e.g., energy sufficient for tissue ablation) from a particular transducer or electrode.

The phrases "concurrent activation", "concurrent tissue ablation", "concurrent delivery of electrical signals", "concurrent delivery of electrical power", and related phrases are intended to include, in some embodiments, the existence of multiple transducers or electrodes (e.g., as discussed below) in an "on" state or an active state (as opposed to, e.g., an "off" state or a "sleep" state) to perform one or more determined functions at a same time or during a same time period. For example, multiple transducers performing concurrent tissue ablation may include the multiple transducers actively receiving tissue-ablative energy from an energy source device system at a same time or during a same time period. In such example, there may be a case where the tissue-ablative energy includes alternating current or electrical energy provided via a duty cycle to perform the tissue ablation, where, e.g., one transducer of the multiple transducers is instantaneously receiving electrical energy out of phase (e.g., +/− in the case of alternating current or energy/no energy in the case of a duty cycle) with another transducer of the multiple transducers. In such a case, the multiple transducers are still deemed to be performing concurrent tissue ablation (e.g., even if one transducer in the multiple transducers is instantaneously receiving electrical energy and another transducer in the multiple transducers is not, due to a duty cycle being applied to the tissue ablative energy), since, e.g., the application of the tissue ablative energy is in an "on" state (the "on" state in this example case being via the application of an alternating current or the application of duty cycled energy). In some, but not all embodiments, the phrases "concurrent activation", "concurrent tissue ablation", "concurrent delivery of electrical signals", "concurrent delivery of electrical power", and related phrases include the concurrent placing or changing of multiple transducers or electrodes (e.g., as discussed below) into an "on" state or an active state (as opposed to, e.g., an "off" state or a "sleep" state) to perform one or more determined functions at a same time or during a same time period. For example, multiple transducers being concurrently activated may include the multiple transducers being activated at a same time, as opposed, e.g., to one transducer of the multiple transducer having its activation initiated first, and then another of the multiple transducers having its activation initiated at a later time.

The phrase "derivative thereof" and the like is or may be used herein at times in the context of a derivative of data or information merely to emphasize the possibility that such data or information may be modified or subject to one or more operations. For example, if a device generates first data for display, the process of converting the generated first data into a format capable of being displayed may alter the first data. This altered form of the first data may be considered a derivative of the first data. For instance, the first data may be a one-dimensional array of numbers, but the display of the first data may be a color-coded bar chart representing the numbers in the array. For another example, if the above-mentioned first data is transmitted over a network, the process of converting the first data into a format acceptable for network transmission or understanding by a receiving device may alter the first data. As before, this altered form of the first data may be considered a derivative of the first data. For yet another example, generated first data may undergo a mathematical operation, a scaling, or a combining with other data to generate other data that may be considered derived from the first data. In this regard, it can be seen that data is commonly changing in form or being combined with other data throughout its movement through one or more data processing device systems, and any reference to information or data herein is intended to include these and like changes, regardless of whether or not the phrase "derivative thereof" or the like is used in reference to the information or data, unless otherwise required by context. As indicated above, usage of the phrase "or a derivative thereof" or the like merely emphasizes the possibility of such changes. Accordingly, the addition of or deletion of the phrase "or a derivative thereof" or the like should have no impact on the interpretation of the respective data or information. For example, the above-discussed color-coded bar chart may be considered a derivative of the respective first data or may be considered the respective first data itself.

The term "program" in this disclosure should be interpreted as a set of instructions or modules that may be executed by one or more components in a system, such as a controller system or data processing device system, in order to cause the system to perform one or more operations. The set of instructions or modules may be stored by any kind of memory device, such as those described subsequently with respect to the memory device system 130, 330, or both, shown in FIGS. 1, 3A, and 3B, respectively. In addition, this disclosure may describe or similarly describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into a particular form executable by the one or more data processing devices to cause performance of the action (e.g., in the case where the instructions or modules are encrypted in a non-executable manner, but through performance of a decryption process, would be translated into a form ready for execution). Such descriptions should be deemed to be equivalent to describing that the instructions or modules are configured to cause the performance of the action. The word "module" may be defined as a set of instructions. The word "program" and the word "module" may each be interpreted to include multiple sub-programs or multiple sub-modules, respectively. In this regard, reference to a program or a module may be considered to refer to multiple programs or multiple modules.

Further, it is understood that information or data may be operated upon, manipulated, or converted into different forms as it moves through various devices or workflows. In this regard, unless otherwise explicitly noted or required by context, it is intended that any reference herein to information or data includes modifications to that information or data. For example, "data X" may be encrypted for transmission, and a reference to "data X" is intended to include both its encrypted and unencrypted forms, unless otherwise required or indicated by context. For another example, "image information Y" may undergo a noise filtering process, and a reference to "image information Y" is intended to include both the pre-processed form and the noise-filtered form, unless otherwise required or indicated by context. In other words, both the pre-processed form and the noise-filtered form are considered to be "image information Y", unless otherwise required or indicated by context. In order to stress this point, the phrase "or a derivative thereof" or the like may be used herein. Continuing the preceding example, the phrase "image information Y or a derivative thereof" refers to both the pre-processed form and the noise-filtered form of "image information Y", unless otherwise required or indicated by context, with the noise-filtered form potentially being considered a derivative of "image information Y". However, non-usage of the phrase "or a derivative thereof" or the like nonetheless includes derivatives or modifications of information or data just as usage of such a phrase does, as such a phrase, when used, is merely used for emphasis.

FIG. 1 schematically illustrates at least part of a medical device system 100 according to some embodiments. In some embodiments, the medical device system 100 includes a data processing device system 110, an input-output device system 120, and a processor-accessible memory device system 130. The processor-accessible memory device system 130 and the input-output device system 120 are communicatively connected to the data processing device system 110. The data processing device system 110 includes one or more data processing devices that implement or execute, in conjunction with other devices, such as those in the system 100, methods of various embodiments that may be employed by various aspects described in this disclosure. Each of the phrases "data processing device", "data processor", "processor", "computer", "controller" and the like is intended to include any data processing device, such as a central processing unit ("CPU"), a desktop computer, a laptop computer, a mainframe computer, a tablet computer such as an iPad (Trademark Apple Inc., Cupertino California), a personal digital assistant, a cellular phone, a smartphone, or any other device for processing data, managing data, or handling data, whether implemented with electrical, magnetic, optical, biological components, or otherwise.

The memory device system 130 includes one or more processor-accessible memory devices configured to store information, including the programs, information, or both, needed to execute the methods associated with various embodiments. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" and the like is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include or be a processor-accessible (or computer-readable (e.g., may also referred to as controller-readable)) data storage medium. In some embodiments, each of the phrases "processor-accessible memory" and "processor-accessible memory device" is intended to include or be a non-transitory processor-accessible (or computer/controller-readable) data storage medium. In some embodiments, the processor-accessible memory device system 130 may be considered to include or be a non-transitory processor-accessible (or computer/controller-readable) data storage medium system. And, in some embodiments, the memory device system 130 may be considered to include or be a non-transitory processor-accessible (or computer/controller-readable) storage medium system or data storage medium system including or consisting of one or more non-transitory processor-accessible (or computer/controller-readable) storage or data storage mediums.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing device system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 may be implemented by a single application-specific integrated circuit (ASIC) in some embodiments.

The input-output device system 120 may include a mouse, a keyboard, a touch screen, another computer, an image-generating device system, a display device system, a printer device system, a speaker device system, a processor-accessible memory device system, a transducer or electrode based device system, one or more transducers, one or more electrodes, one or more conductors, or any device or combination of devices (a) from which a desired selection, desired information, desired instructions, or any other data is input to the data processing device system 110, (b) to which information, instructions, or any other data is output from the data processing device system 110, or both (a) and (b). The input-output device system 120 may include a user-activatable control system that is responsive to a user action, such as actions from a care provider such as a physician or technician. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion of a medical system, transducer-based device system, or an electrode-based device system described herein. The phrase "transducer-based device system" is intended to include one or more physical devices or systems that include various transducers. Similarly, the phrase "electrode-based device system" is intended to include one or more physical devices or systems that include various electrodes. In this regard, the phrases "transducer-based device system" and "electrode-based device system" may be used interchangeably in accordance with various embodiments. Similarly, the phrases "transducer-based device" and "electrode-based device" may be used interchangeably in accordance with various embodiments. If the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

Figure 2A:
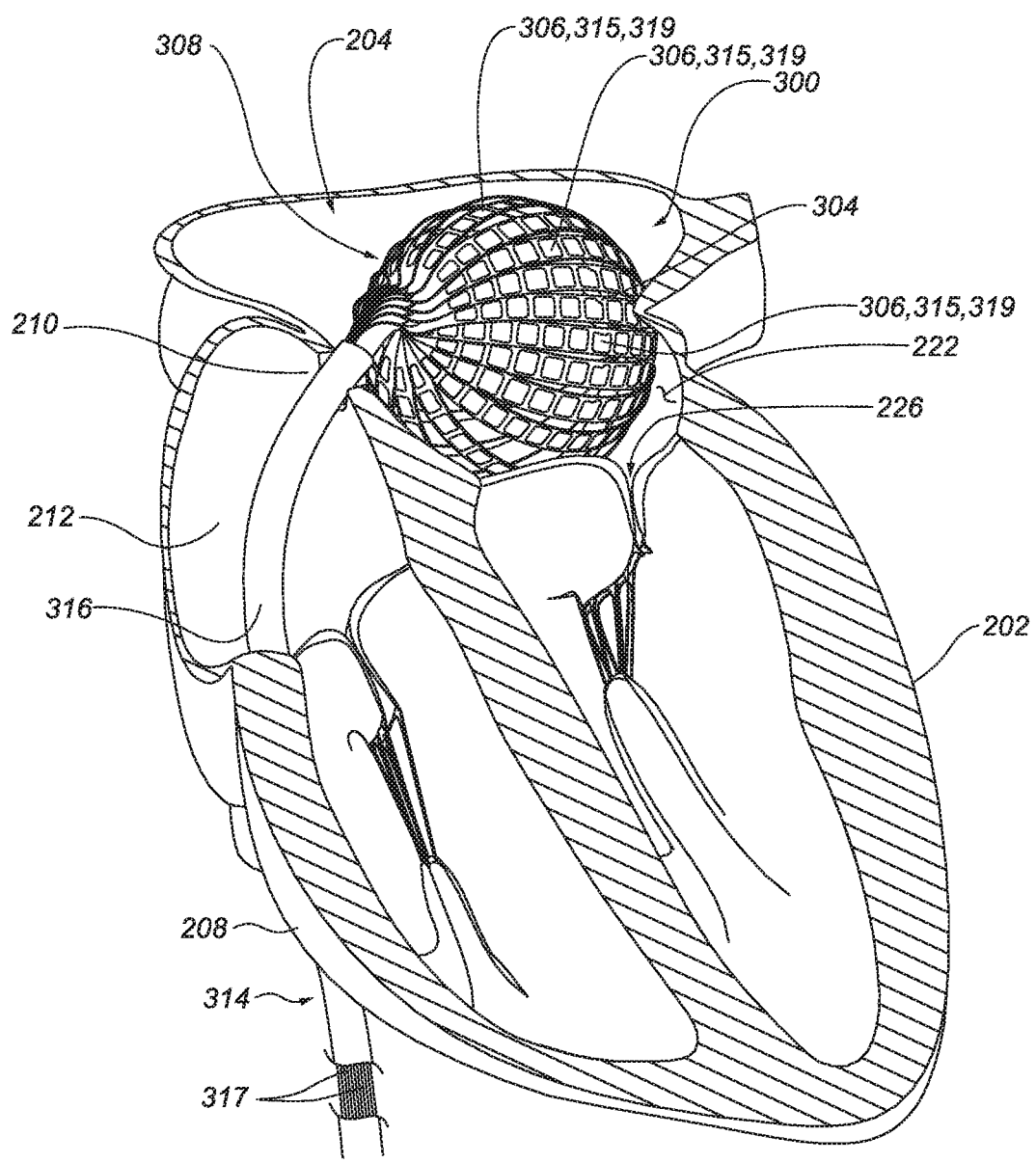
FIGS. 2A and 2B are cutaway diagrams of a heart showing an electrode-based device system percutaneously placed in a left atrium of the heart in respective particular orientations according to various example embodiments, the electrode-based device system optionally being part of the input-output device system of FIG. 1, according to some embodiments.
Figure 2B:
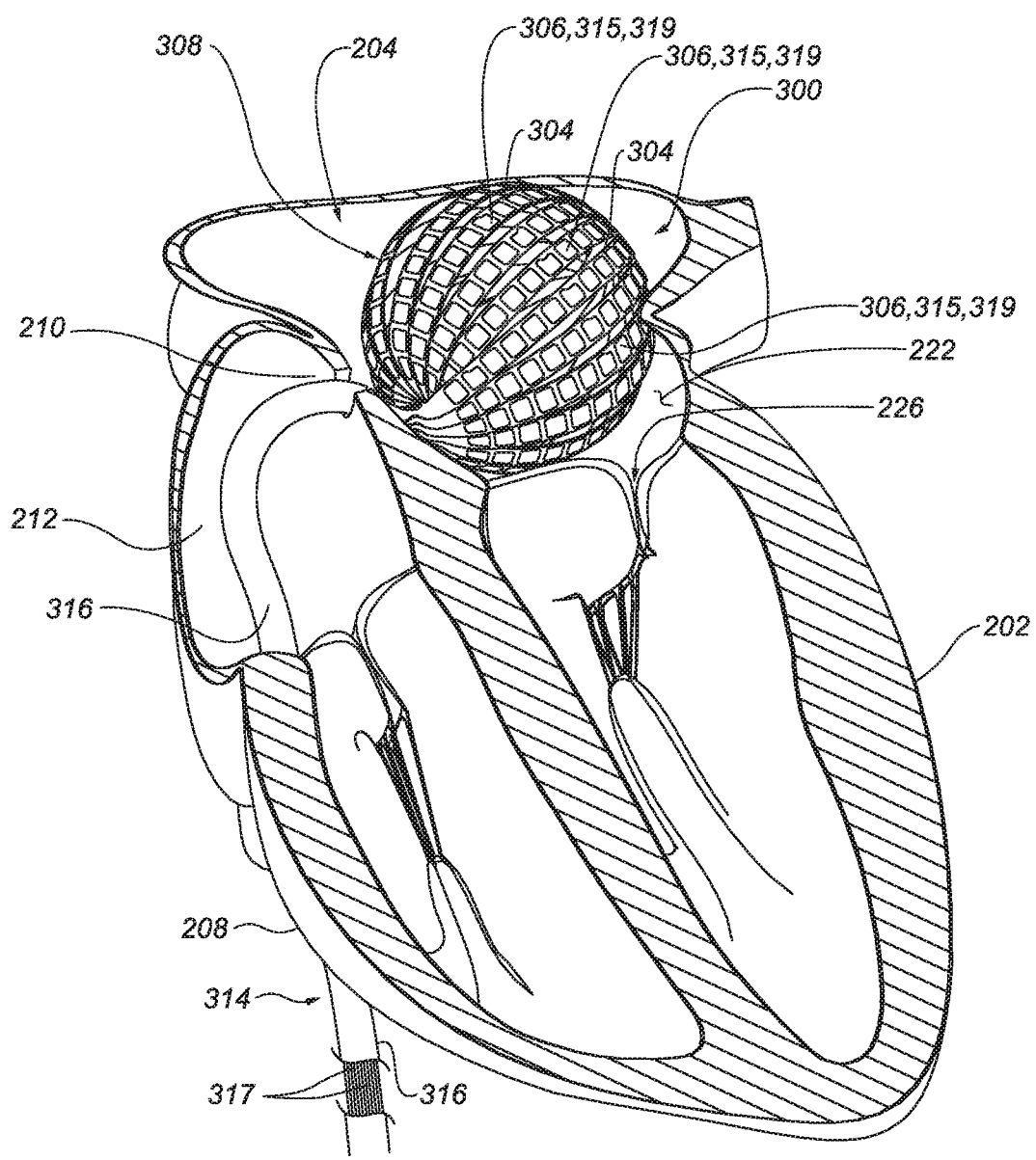

FIGS. 2A and 2B show an electrode-based device system 300, which may be all or part of a medical system or medical device system, and which may be included in the input-output device system 120 of FIG. 1, according to some embodiments. Because, as described in more detail below with respect to FIG. 4, electrodes may be part of transducers, according to some embodiments, the system 300 may also be considered a transducer-based device system in some embodiments.

Such a system 300 may be beneficial for, among other things, investigating or treating a bodily organ, for example, a heart 202, according to some example embodiments. The electrode-based device system 300 may include a frame or structure 308 that may be percutaneously or intravascularly inserted into a portion of the heart 202 of a patient, such as an intra-cardiac cavity like left atrium 204. In some embodiments, the structure 308 is formed at least by a plurality of elongate members 304 (one called out in FIG. 2A and two called out in FIG. 2B) which provide transducers 306. Accordingly, in some embodiments, the plurality of transducers 306 are located on the structure 308. Although the embodiments associated with FIGS. 2A, 2B, 3A, 3B, and 3C show embodiments of systems 300 with ten elongate members 304, different embodiments may have different numbers of elongate members 304.

Returning to the example of FIGS. 2A and 2B, the electrode-based device system 300 includes catheter 314 inserted via the inferior vena cava 208 and penetrating through a bodily opening in transatrial septum 210 from right atrium 212. In other embodiments, other paths may be taken.

Catheter 314 may include an elongated rod or shaft member 316 (also referred to as a carrier member 316) appropriately sized to be deliverable percutaneously or intravascularly. In some embodiments, shaft member 316 is considered to be a flexible member with sufficient flexibility to negotiate a tortuous path to the bodily cavity. According to various embodiments, the shaft member 316 may be employable or configured to percutaneously or intravascularly deliver the structure 308 to a location within a patient, such as, through a bodily opening (e.g., the bodily opening in transatrial septum 210) leading to a bodily cavity of a patient (e.g., left atrium 204 of the heart 202). According to various embodiments, the shaft member 316 may be employable or configured to percutaneously or intravascularly deliver the structure 308 through a bodily opening (e.g., the bodily opening in transatrial septum 210) leading to a bodily cavity of a patient (e.g., left atrium 204 of the heart 202) at least in response to translation of at least part of the shaft member 316. The shaft member 316 may include a shaft proximal end portion 316a (not shown in FIG. 2A or 2B, but shown, for example, in FIG. 3A). The shaft member 316 may also include a shaft distal end portion 316b (shown, for example, in FIG. 3A), with the structure 308 physically coupled to the shaft member 316 at least proximate the shaft distal end portion 316b. At least part of the shaft member 316 may be sized to be percutaneously deliverable toward the location within the patient (e.g., the bodily cavity of the patient) distal end portion 316b ahead of the proximal end portion 316a. The shaft member 316 may include an elongated portion 316c (shown, for example, in FIG. 3A) extending between the shaft proximal end portion 316a and the shaft distal end portion 316b. According to some embodiments, the shaft member 316 includes a length along the shaft member extending between the proximal end portion 316a and the distal end portion 316b. In some embodiments, the length of the shaft member 316 extends from the proximal end of the proximal end portion 316a to the distal end of the distal end portion 316b. In some embodiments, the length of the shaft member 316 is sufficient to position the proximal end portion 316a at a location outside a body comprising the bodily cavity of a patient during a state in which the structure 308 is positioned in the bodily cavity of the patient. In some embodiments, the shaft member 316 includes at least a first lumen sharing the length of the shaft member 316. In this regard, at least the first lumen of the shaft member 316 may extend between the proximal end portion 316a and the distal end portion 316b. The structure 308 may be configured to be delivered through the first lumen of the shaft member 316 as the structure 308 is percutaneously delivered toward a location within a body of a patient (e.g., a bodily cavity of the patient).

In various embodiments, the shaft member 316 is physically coupled to the structure 308 at a location fixed with respect to the shaft distal end portion 316b. In various embodiments, the physical coupling between the shaft member 316 and the structure 308 allows for a movement (e.g., a translation) of the structure 308 in response to a movement (e.g., a translation) of at least part of the shaft member 316. In some embodiments, the structure 308 is physically coupled to shaft member 316 at a location that does not vary with respect to the shaft distal end portion 316b in response to a movement (e.g., a translation) of at least part of the shaft member 316. In some embodiments, the structure 308 is physically coupled to the distal end portion 316b of the shaft member 316. In some embodiments, the shaft member 316 is fixedly coupled to the structure 308. The shaft member 316 may be physically coupled to the plurality of elongate members 304, such that a respective location at which the shaft member 316 is physically coupled to each elongate member 304 is fixed with respect to the shaft distal end portion 316b of the shaft member 316, according to some embodiments.

Various portions of catheter 314 may be steerable. Catheter 314 may include one or more lumens. The lumen(s) may carry one or more communications or power paths, or both. For example, each of at least a first lumen provided by catheter 314 (e.g., each of at least a first lumen provided by the shaft member 316) may carry, or contain within it, one or more electrical conductors or conductors 317. In some embodiments, at least a part or portion of each conductor 317 is located within the shaft member 316. Electrical conductors 317 provide electrical connections for system 300 that are accessible externally from a patient in which the electrode-based device system 300 is inserted, according to some embodiments. In some embodiments, the electrical conductors 317 form part of various elongate members (e.g., elongate members 304 described below). In some embodiments, the electrical conductors 317 include, or form part of, various flexible circuit structures (e.g., as described in FIG. 4, below). In some embodiments, the electrical conductors 317 may be encased within the shaft member 316.

In some embodiments, the electrical conductors 317 are coupled to the transducers 306 to provide electrical connections to transducers 306 (three called out in each of FIGS. 2A and 2B). In some embodiments, each conductor 317 is coupled to a respective transducer 306. The conductors 317 and the transducers 306 may be considered part of the input-output-device system 120, e.g., in at least some embodiments where the conductors 317 are coupled to a data processing device system 110, such as a controller 324 (or data processing device 310 therein) discussed below. In at least such embodiments, the data processing device system 110 is communicatively connected to the transducers 306 via the conductors 317. The transducers 306 respectively may include one or more electrodes, and optionally one or more other devices, (e.g., both discussed with respect to FIG. 4, below) configured to, among other things, provide stimulation (e.g., electrical stimulation that may include pinging or pacing) to tissue within a bodily cavity (e.g., left atrium 204), ablate tissue in a desired pattern within the bodily cavity, sense characteristics of tissue or other physical characteristics (e.g., electrophysiological activity, convective cooling, permittivity, force, temperature, impedance, thickness, or a combination thereof) within the bodily cavity, or a combination thereof.

The sensing of characteristics may, among other things, be configured to distinguish between fluid, such as fluidic tissue (e.g., blood), and non-fluidic tissue forming an interior surface of a bodily cavity (e.g., left atrium 204); may be configured to map the cavity, for example, using positions of openings or ports into and out of the cavity; may be configured to determine a position or orientation (e.g., pose), or both of a portion of the device system 300 in the bodily cavity; may be configured to indicate whether an ablation has been successful; or a combination thereof.

Electrode-based device system 300 may include the frame or structure 308 on which the plurality of transducers 306 are located and which may assume an unexpanded or delivery configuration (e.g., FIG. 3A discussed below) for delivery to left atrium 204. Structure 308 may be deployed or expanded (e.g., shown in a deployed or expanded configuration in FIGS. 2A and 2B, as well as at least FIGS. 3B, and 3C, which are discussed below) upon delivery to left atrium 204. In this regard, in some embodiments, the electrode-based device system 300 or the structure 308 thereof is selectively moveable between a delivery or unexpanded configuration (e.g., FIG. 3A discussed below) and a deployed or expanded configuration (e.g., FIGS. 2A and 2B, as well as at least FIGS. 3B, and 3C discussed below). U.S. Pat. No. 9,452,016, issued Sep. 27, 2016, includes disclosures regarding various actuators, control lines, and other mechanisms by which a transducer or electrode-based device may be selectively moveable between a delivery or unexpanded configuration and a deployed or expanded configuration, and U.S. Pat. No. 9,452,016, issued Sep. 27, 2016 is hereby incorporated herein by reference in its entirety. In the delivery or unexpanded configuration, a portion (e.g., the structure 308) of the device system 300 is sized to be percutaneously or intravascularly deliverable to a bodily cavity, e.g., via passage thereof through a bodily opening leading to the bodily cavity, according to some embodiments. In some embodiments where a first particular portion of each elongate member 304 is included in the structure 308, the first portions of the elongate members 304 are sized to be percutaneously or intravascularly deliverable to the bodily cavity when the structure 308 is in the delivery or unexpanded configuration. In the deployed or expanded configuration, a portion (e.g., the structure 308 or first particular portions 309a of elongate members 304 discussed below) of the device system 300 is sized too large to be percutaneously or intravascularly deliverable to the bodily cavity and to allow passage thereof through the bodily opening leading to the bodily cavity. In some embodiments where a first particular portion 309a of each elongate member 304 is included in the structure 308, the first portions of the elongate members 304 are sized too large to be percutaneously or intravascularly deliverable to the bodily cavity and to allow passage thereof through the bodily opening leading to the bodily cavity.

An example of an expanded or deployed configuration is when the portion of the electrode-based device system (e.g., the structure 308) is in its intended-deployed-operational state inside the bodily cavity. Another example of the expanded or deployed configuration is when the portion of the electrode-based device system 300 is being changed from the delivery configuration to the intended-deployed-operational state to a point where the portion of the device system now has a size too large for passage through the bodily opening leading to the bodily cavity. In some embodiments, the portion of the electrode-based device system 300 has a size or dimension when the structure 308 is in the expanded or deployed configuration that is larger than the corresponding size or dimension of the portion of the electrode-based device system 300 in the delivery configuration. Further, in some embodiments, when the portion (e.g., the structure 308) is in the expanded or deployed configuration in the left atrium 204, various ones of a plurality of transducers 306 may be positionable proximate the interior surface formed by non-fluidic tissue 222 of left atrium 204. In some embodiments, when the portion (e.g., the structure 308) is in the expanded or deployed configuration in the left atrium 204, various ones of plurality of transducers 306 may be positionable such that a physical portion of each of the various ones of the transducers 306 is configured to contact the interior surface formed by non-fluidic tissue 222 of left atrium 204. In some embodiments, at least some of the transducers 306 are configured to sense a physical characteristic of a fluid (i.e., blood), non-fluidic tissue 222 (i.e., cardiac wall tissue), or both, that may be used to determine a position of a particular anatomical feature (e.g., a cardiac port provided by a pulmonary vein or a cardiac valve). In some embodiments, at least some of the transducers 306 are configured to sense a physical characteristic (e.g., an electric or magnetic field created by various locator or navigation systems) to determine a position or orientation (i.e., pose), or both, of a portion of a device system 300 within, or with respect to left atrium 204. For example, transducers 306 may be configured to determine a location of pulmonary vein ostia (not shown) or a mitral valve 226, or both. In some embodiments, at least some of the transducers 306 may be controlled to selectively ablate portions of the non-fluidic tissue 222. For example, some of the transducers 306 may be controlled to ablate a pattern or path around various ones of the bodily openings, ports or pulmonary vein ostia, for instance, to reduce or eliminate the occurrence of atrial fibrillation. Each of various ones of the transducers 306 may include an electrode in various embodiments, as described below with respect to FIG. 4, for example. In some embodiments, structure 308 may take other forms. For example, in some embodiments, structure 308 may form a portion of shaft member 316 upon which at least some of the transducers 306 are located. In some embodiments, structure 308 may not include various elongate members (e.g., elongate members 304). For example, according to some embodiments, structure 308 may be provided at least in part by a bladder or balloon-like structure upon which at least some of the transducers 306 may be located. In some embodiments, such bladder or balloon-like structure may be selectively inflatable (e.g., via an injection of a pressurized fluid such as saline) to move the structure from a delivery configuration in which the structure is sized to be percutaneously or intravascularly deliverable and an expanded or deployed configuration in which the structure is sized too large to be percutaneously or intravascularly deliverable.

Figure 3A:
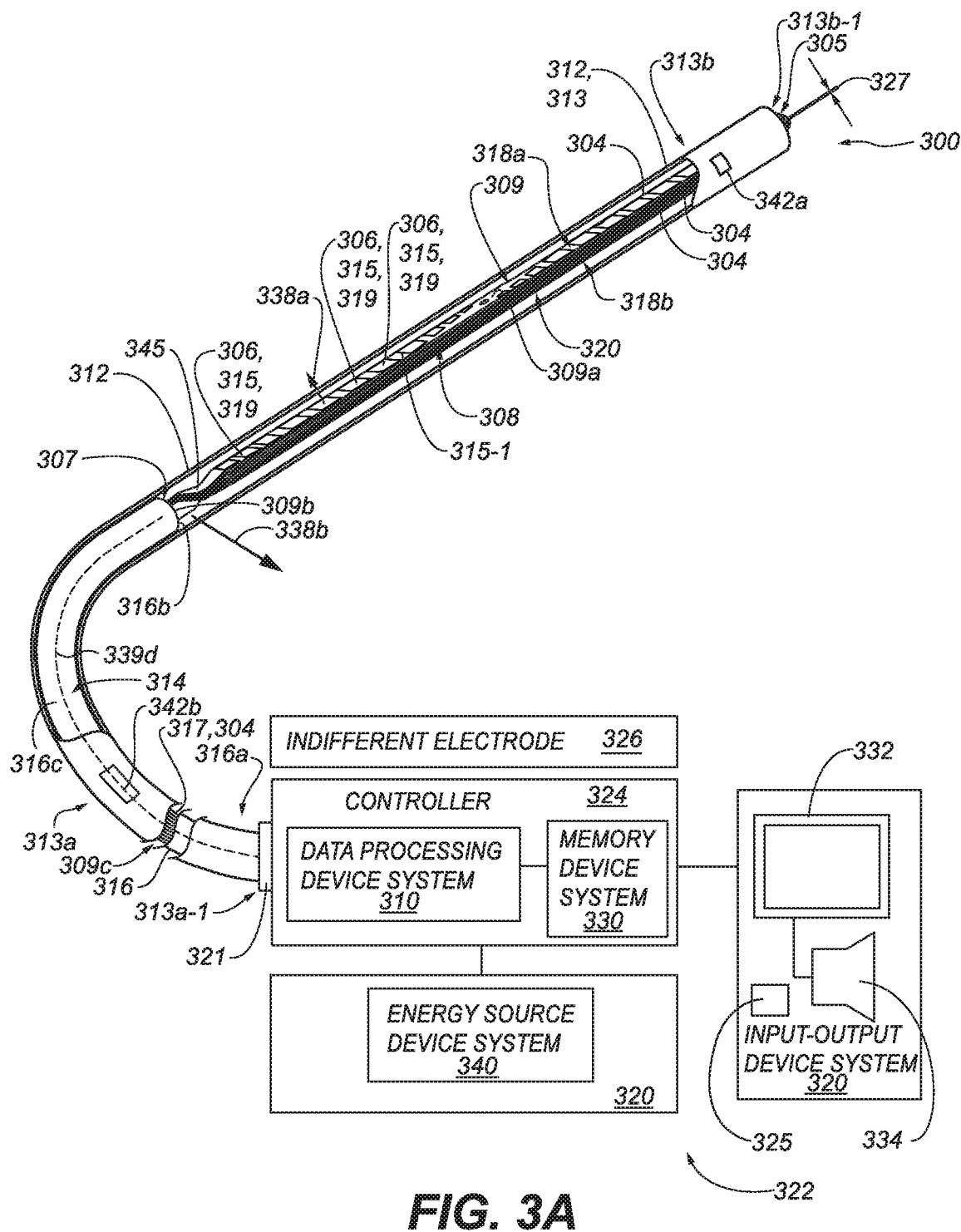
FIG. 3A is a partial schematic view of a medical device system, which may represent one or more implementations of the medical device system of FIG. 1 in which an expandable structure of an electrode-based device system is in a delivery or unexpanded configuration, according to various example embodiments.
Figure 3B:
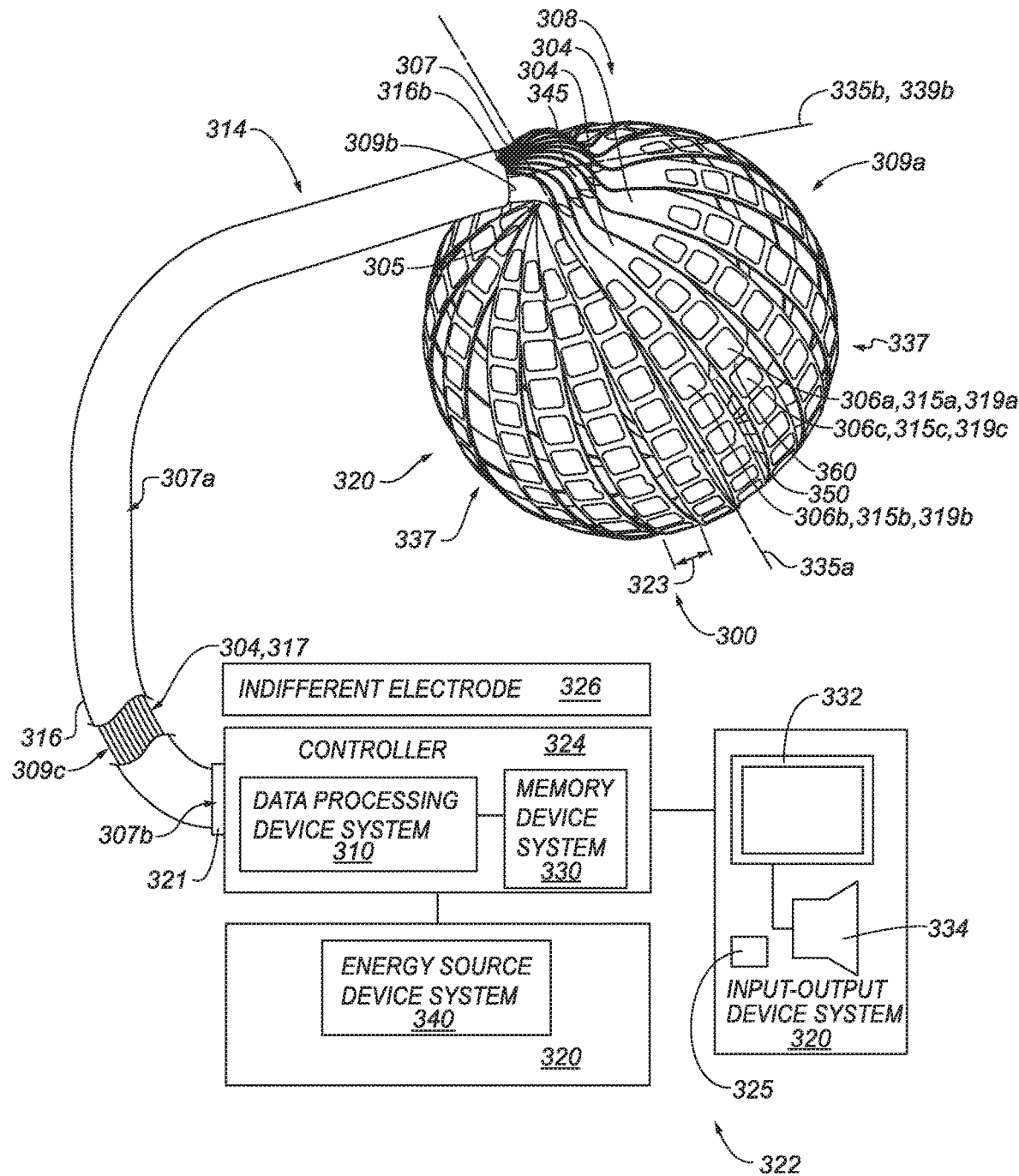
FIG. 3B is a partial schematic view of the medical device system of FIG. 3A with the expandable structure shown in a deployed or expanded configuration, according to some embodiments.

Each of FIGS. 3A and 3B is a partial schematic representation of a medical device system, which may represent one or more implementations of the medical device system 100 of FIG. 1, according to some embodiments. The medical system of each of these figures may include the electrode-based device system 300, which itself may include at least one hundred transducers 306 or electrodes 315 (only a few called out in the figures), but need not include that many. FIG. 3A illustrates the electrode-based device system 300 in a delivery or unexpanded configuration, according to various example embodiments, and FIGS. 3B and 3C illustrate the electrode-based device system 300 in a deployed or expanded configuration, according to some embodiments.

In this regard, the electrode-based device system 300 may include a plurality of elongate members 304 (only a few called out in the figures) and a plurality of transducers 306 or electrodes 315 (only a few called out in the figures). In some embodiments, the transducers 306 or electrodes 315 have the configuration of the transducers 306 or electrodes 315 in FIGS. 2A and 2B (or at least FIG. 3A or 3B and 3C).

In some embodiments, the transducers 306 or electrodes 315 are formed as part of, coupled to, or are located on, at least some of the elongate members 304. In this regard, in some embodiments, each elongate member 304 has located thereon a respective set of one or more of the transducers 306. Accordingly, the transducers 306 located on a single elongate member 304 may be considered a set of transducers in some embodiments. In this regard, it may be considered that a plurality of sets of one or more transducers 306 exists with, in some embodiments, each transducer set being located on a respective elongate member 304. In other contexts, however, a transducer set is not limited to one or more transducers 306 residing on a single elongate member 304. As discussed in more detail below (for example with respect to FIG. 4), the transducers 306 may include electrodes 315, such that each transducer 306 includes a respective electrode 315 according to some embodiments. In some embodiments, the transducers 306 or electrodes 315 are operable to be energized (e.g., via an energy source device system 340, discussed below) to interact with tissue within the bodily cavity.

Figure 3C:
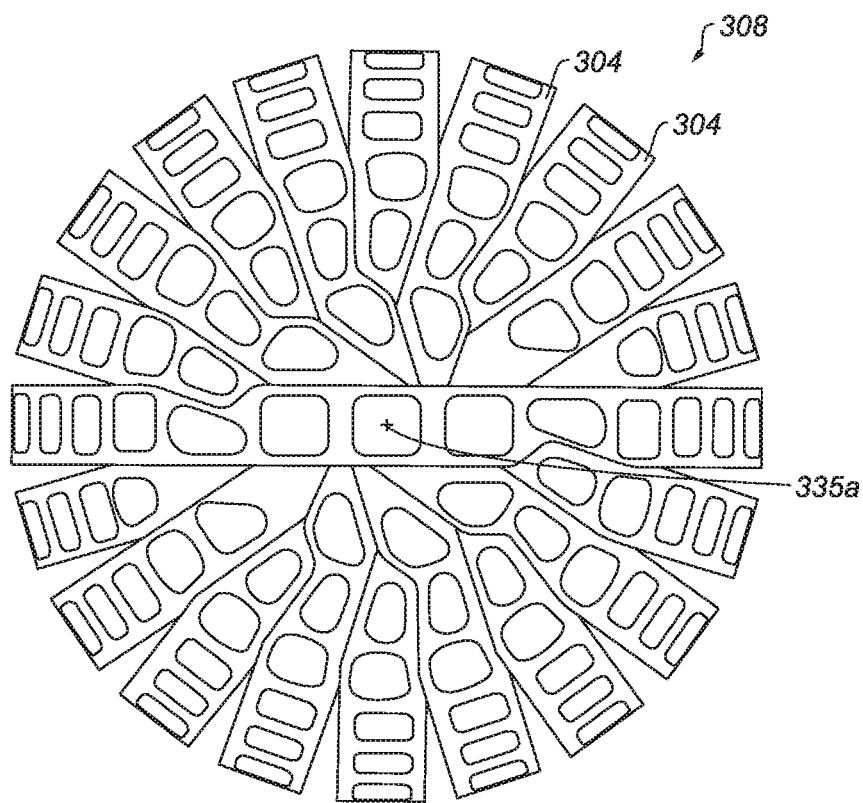
FIG. 3C illustrates a portion of the medical device system of FIG. 3A as viewed from a different viewing angle, according to some embodiments.

In some embodiments, the elongate members 304 are arranged as, or form at least part of, the frame or structure 308 that is selectively moveable between an unexpanded or delivery configuration (e.g., as shown in FIG. 3A) and an expanded or deployed configuration (e.g., as shown in FIGS. 3B and 3C) that may be used to position or distribute particular portions of elongate members 304 at various locations within a bodily cavity (e.g., locations away from a tissue surface within the bodily cavity, locations against a tissue surface, or locations at least proximate the tissue surface).

In some embodiments, the structure 308 has a size in the unexpanded or delivery configuration suitable to allow the structure 308 to be percutaneously or intravascularly deliverable to a location within a patient, e.g., at least partially through a bodily opening (e.g., via catheter sheath 312, shown in FIG. 3A, but not in the other figures for purposes of clarity) to the bodily cavity of the patient. In some embodiments, structure 308 has a size when the structure 308 is in the expanded or deployed configuration too large to allow the structure to be intravascularly or percutaneously deliverable to the location within the patient, e.g., through a bodily opening (e.g., via catheter sheath 312) to the bodily cavity of the patient.

The elongate members 304 may form part of or include a flexible circuit structure (i.e., also known as a flexible printed circuit board (PCB) circuit). In various embodiments, each of the elongate members 304 may form part of or include a respective flexible circuit structure. For example, in some embodiments, each of the elongate members 304 may form part of or include a respective flexible circuit structuring having an elongated or strip-like form. The elongate members 304 may include a plurality of different material layers. Each of the elongate members 304 may include a plurality of different material layers. The structure 308 may include a shape memory material, for instance Nitinol. The structure 308 may include a metallic material, for instance stainless steel, or non-metallic material, for instance polyimide, or the structure 308 may include both a metallic and a non-metallic material by way of non-limiting example. The incorporation of a specific material into structure 308 may be motivated by various factors including the specific requirements of each of the unexpanded or delivery configuration and expanded or deployed configuration, the required position or orientation (i.e., pose) or both of structure 308 in the bodily cavity, or the requirements for successful ablation of a desired pattern. For clarity, not all of the elongate members shown in the deployed or expanded configuration shown in FIG. 3B are shown in the structure 308 in the delivery configuration shown in FIG. 3A.

One or more transducers of the plurality of transducers 306 is or are positionable within a bodily cavity, for example, by positioning of the structure 308. For instance, in some embodiments, various ones of the transducers 306 are able to be positioned in a bodily cavity by movement into, within, or into and within the bodily cavity, with or without a change in a configuration of the plurality of transducers 306 (e.g., a change in a configuration of the structure 308 causes a change in configuration of the transducers 306 in some embodiments). In some embodiments, the plurality of transducers 306 is arrangeable to form a two- or three-dimensional distribution, grid or array capable of mapping, ablating or stimulating or otherwise interacting with an inside surface of a bodily cavity or lumen without requiring mechanical scanning.

As shown for example in FIG. 3A, the plurality of transducers 306 is arranged in a distribution receivable in a bodily cavity (not shown in FIG. 3A). As shown for example, in FIG. 3A, the plurality of transducers 306 is arranged in a distribution suitable for delivery to a bodily cavity, according to some embodiments. Also as shown for example in FIG. 3A, the structure 308, when in the delivery configuration, arranges at least part of each respective elongate member of the plurality of elongate members 304 to be advanced with a distal end (also referred to as the second end) 305 of the respective elongate member 304 ahead of a proximal portion 307 of the respective elongate member 304 toward the bodily cavity, according to some embodiments. In some embodiments, proximal portion 307 is located within shaft member 316 (e.g., within a lumen in shaft member 316). In some embodiments, the proximal portion 307 may be considered an external proximal portion, because it exists just external of the shaft member 316 (for example as described below), according to some embodiments.

FIG. 3B shows another proximal portion 307a of each respective elongate member 304 located within the shaft member 316. Also shown in FIG. 3B is yet another proximal portion 307b of each respective elongate member 304 located at a proximal end of each respective elongate member 304 where each respective elongate member 304 terminates, e.g., at the connector 321, at a controller 324, or at the data processing device system 310, according to various embodiments. Accordingly, the proximal portion 307b of each respective elongate member 304 may be considered a respective proximal end of the respective elongate member 304. (Although the arrows 307a, 307b point near an exterior of the shaft member in FIG. 3B, such arrows are intended to refer to an interior where the elongate members reside according to some embodiments.) In some embodiments, the proximal portion (e.g. 307a, 307b) of each respective elongate member 304 includes portions of various ones of conductors 317. In some embodiments, an end of the proximal portion 307 of each respective elongate member 304 may be located within shaft member 316. In some embodiments, an end of the proximal portion 307 of each respective elongate member 304 may be located closer to the distal end portion 316b of shaft member 316 than to proximal end portion 316a of shaft member 316.

In some embodiments, as shown, for example, in FIG. 3A, each of the plurality of elongate members 304 is arranged to be percutaneously or intravascularly deliverable distal end first or distal end ahead of various ones of the proximal portions 307 to the bodily cavity when the structure is in the delivery configuration. In some embodiments, at least some of the elongate members 304 are arranged to be percutaneously or intravascularly deliverable with a portion thereof other than the distal end delivered first to the bodily cavity when the structure is in the delivery configuration.

Figure 4:
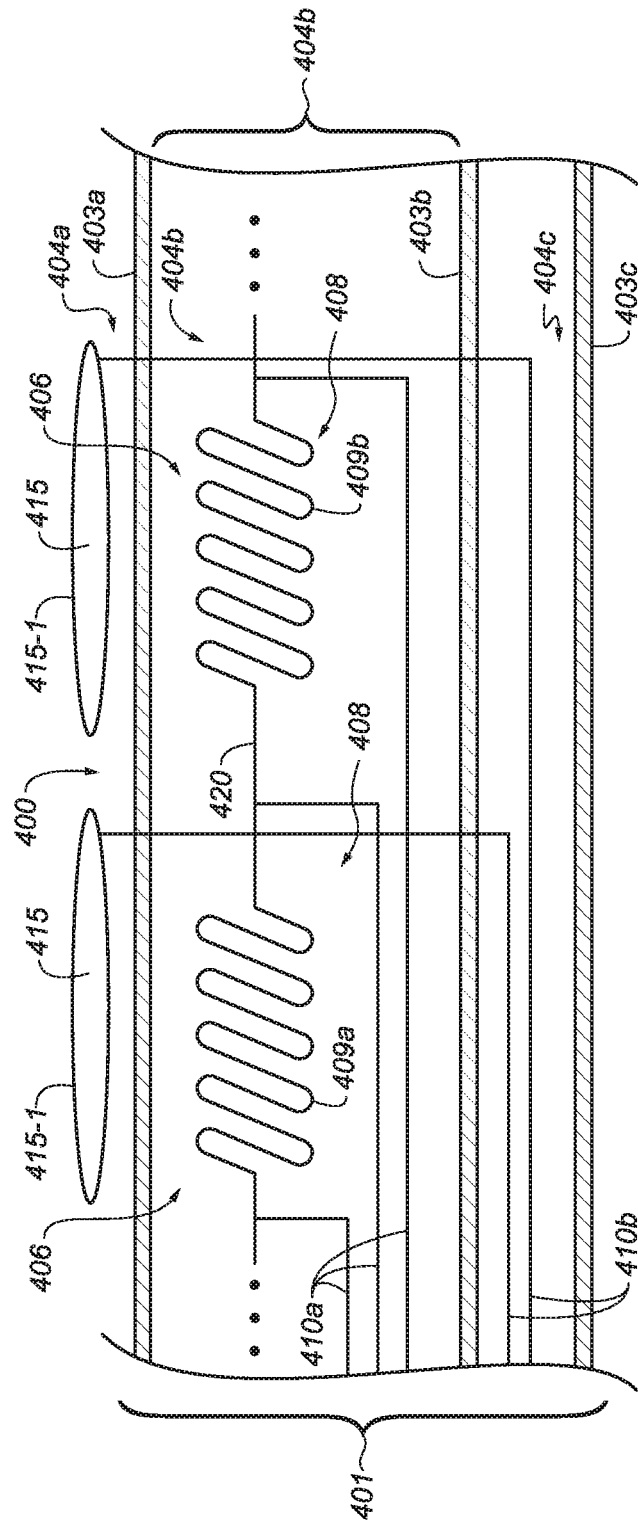
FIG. 4 is a schematic representation of an electrode-based device system that includes a flexible circuit structure, according to various example embodiments.

FIG. 4 is a schematic side elevation view of at least a portion of an electrode-based device system 400 that includes a flexible circuit structure 401 that is employed to provide a plurality of transducers 406 (two called out) according to various example embodiments. The portion of the electrode-based device system 400 may form part of each of one or more or all elongate members 304, according to some embodiments. In some embodiments, the transducers 406 correspond to the transducers 306. In some embodiments, at least a particular portion of the flexible circuit structure 401 may form part of a structure (e.g., structure 308) that is selectively moveable between a delivery configuration sized for percutaneous or intravascular delivery and an expanded or deployed configuration sized too large for percutaneous or intravascular delivery. In some embodiments, at least a particular portion of the flexible circuit structure 401 may be located on, or form at least part of, a structural component (e.g., elongate member 304) of an electrode-based device system (e.g., electrode-based device system 300). In some embodiments, at least part of the flexible circuit structure 401 may provide each particular portion of an elongate member. For each respective elongate member 304, the flexible circuit structure 401 may include or may form at least part of a respective portion (e.g., the respective portion 309a (discussed in more detail below), the respective portion 309b (discussed in more detail below), the respective portion 309c (discussed in more detail below), or a combination of two or all of such portions or other portions described herein) of the respective elongate member 304. For example, in some embodiments, the flexible circuit structure 401 may begin at a connection associated with data processing device system 310 and extend at least to and in some embodiments, include the transducers 306 of the respective elongate member 304. For another example, in some embodiments, conductors may be connected at one end to one or more connectors associated with the data processing device system 310 and extend through some proximal portion of the shaft member 316 and be connected at the other end to the flexible circuit structure 401 at some intermediate internal proximal portion (e.g., 307a or other portion within the shaft member 316) where the flexible circuit structure 401 and its respective elongate member 304 begin. In some embodiments, for each respective elongate member 304, a multi-layer structure (e.g., flexible circuit structure 401) may include or may form at least part of a respective portion (e.g., the respective portion 309a (discussed in more detail below), the respective portion 309b (discussed in more detail below), the respective portion 309c (discussed in more detail below), or a combination of two or all of such portions or other portions described herein) of the respective elongate member 304. According to some embodiments, for each respective elongate member 304, the flexible circuit structure 401 may extend or exist at least from a proximal end of the respective elongate member 304 to a distal end of the respective elongate member 304. According to some embodiments, for each respective elongate member 304, the flexible circuit structure 401 may proximally begin at a proximal end of the respective elongate member 304 and end at a distal end of the respective elongate member 304. In some embodiments, for each particular elongate member 304, the particular elongate member 304 includes the flexible circuit structure 401 extending at least between the proximal end of the particular elongate member 304 and the distal end of the particular elongate member 304. In some embodiments, for each particular elongate member 304, the particular elongate member 304 includes the flexible circuit structure 401 extending at least between the proximal portion 307, the proximal portion 307a, or the proximal portion 307b, and the distal end 305 of the particular elongate member 304.

In some embodiments, for each particular elongate member 304, the particular elongate member 304 includes a flexible circuit structure 401 that includes a plurality of separately formed portions, each of the portions physically and electrically coupled together to form flexible circuit structure 401 extending between the proximal end of the particular elongate member 304 and the distal end of the particular elongate member 304. The use of physically and electrically coupled, but separately formed portions may be motivated for different reasons including limitations in flexible printed circuit manufacturing techniques in forming a single flexible circuit structure 401 having sufficient length to extend between the proximal end of the particular elongate member 304 and the distal end of the particular elongate member 304.

In some embodiments, at least a particular portion of the flexible circuit structure 401 may form, provide, or be connected to at least part of one or more conductors (e.g., conductors 317, one or more of which may be connected to, or at least in part form, conductors 410a, 410b in FIG. 4, discussed in more detail below) arranged to provide a power or communications path to various ones of the transducers 406. It is noted that conductors provided by the flexible circuit structure 401 need not be confined to portions of flexible circuit structure 401 forming part of, or positioned at least proximate the structure (e.g., structure 308), but rather may be configured to extend over a substantial portion of a path extending from various ones of the transducers 306 located within a bodily cavity to a location outside a body that comprises the bodily cavity. Such configuration may provide enhanced reliability from a reduced number of required connectors as well as reducing various economic costs associated with the system.

The flexible circuit structure 401 may be formed by various techniques including flexible printed circuit techniques. In some embodiments, the flexible circuit structure 401 includes various layers including flexible layers 403 (three called out in FIG. 4 as reference symbols 403a, 403b, and 403c). In some embodiments, each of the flexible layers 403 includes an electrical insulator material (e.g., polyimide). One or more of the flexible layers 403 may include a different material than another of the flexible layers 403. In some embodiments, the flexible circuit structure 401 includes various electrically conductive layers 404 (three called out in FIG. 4 as reference symbols 404a, 404b, and 404c). The electrically conductive layers 404 may be interleaved with the flexible layers 403. In some embodiments, each of the electrically conductive layers 404 is patterned to form various electrically conductive elements. For example, electrically conductive layer 404a may be patterned to form a respective electrode 415 included as part of each of the transducers 406. Electrodes 415 may have respective electrode edges 415-1 that form a periphery of an electrically conductive surface or surface portion associated with the respective electrode 415.

In some embodiments, the respective electrically conductive surface or surface portion of one or more of the electrodes 415 (or 315) is configured to transmit energy to adjacent or contacting tissue at a level sufficient for ablation of the tissue. Other energy levels may be transmitted to, for example, provide stimulation (e.g., electrical stimulation that may include pinging or pacing) to tissue within a bodily cavity (e.g., left atrium 204), sense characteristics of tissue (e.g., electrophysiological activity, convective cooling, permittivity, force, temperature, impedance, thickness, or a combination thereof) within the bodily cavity, or a combination thereof.

Electrically conductive layer 404*b* is patterned, in some embodiments, to form respective temperature sensors 408 for each of the transducers 406 as well as various conductors 410*a* arranged to provide electrical energy to the temperature sensors 408. In some embodiments, each temperature sensor 408 includes a patterned resistive element 409 (two called out as 409*a* and 409*b*) having a predetermined electrical resistance. In some embodiments, each resistive element 409 includes a metal having relatively high electrical conductivity characteristics (e.g., copper). In some embodiments, the resistive element 409 has a serpentine form. The serpentine form has the advantage of providing an increase in the overall resistance of resistive element 409 by increasing its overall length while maintaining a compact spatial arrangement. In some embodiments, each resistive element 409 is connected to an adjacent resistive element 409 by a conductive element 420 (only one instance of conductive element 420 is shown in FIG. 4 for clarity).

In some embodiments, electrically conductive layer 404*c* is patterned to provide portions of various conductors 410*b* arranged to provide an electrical communication path to electrodes 415. In some embodiments, conductors 410*b* are arranged to pass though vias (accounted for in FIG. 4, e.g., by the upward (with respect to the proper orientation of FIG. 4) movement of the leads 410*b*) in flexible layers 403*a* and 403*b* to connect with electrodes 415. In various embodiments, electrically conductive layer 404*b*, electrically conductive layer 404*c*, or both electrically conductive layer 404*b* and electrically conductive layer 404*c* have sufficient length to allow various ones of conductors 410*a* and 410*b* (or other conductors) to extend at least outside the body of the patient when the transducers 406 are positioned at desired locations within a bodily cavity comprised by the body of the patient. In various embodiments, electrically conductive layer 404*b*, electrically conductive layer 404*c*, or both electrically conductive layer 404*b* and electrically conductive layer 404*c* have sufficient length to allow at least various ones of conductors 410*a* and 410*b* (or other conductors) to extend across all the particular portions of an elongate member. In various embodiments, at least a portion of each of the conductors 410*a* and 410*b* (or other conductors that may or may not be formed by flexible circuit manufacturing techniques) may be located in shaft member 316. In some embodiments, the conductors 410*a*, 410*b* (or other conductors that may or may not be formed by flexible circuit manufacturing techniques) may be considered to be at least part of conductors 317 (e.g., FIGS. 3A and 3B).

Although FIG. 4 shows flexible layer 403*c* as being a bottom-most layer, some embodiments may include one or more additional layers underneath or backing flexible layer 403*c*, such as one or more structural layers, such as a stainless steel or composite layer. These one or more structural layers, in some embodiments, are part of the flexible circuit structure 401 and may be part of, e.g., elongate member 304. In addition, although FIG. 4 shows only three flexible layers 403*a*-403*c* and only three electrically conductive layers 404*a*-404*c*, it should be noted that other numbers of flexible layers, other numbers of electrically conductive layers, or both, may be included. It should be noted that the various structures of the flexible circuit system, such as the electrode 415 and resistive element 409, for example, may include different metals or conductive materials according to some embodiments.

It is noted that various elements such as electrodes 415 and resistive elements 409 are schematically represented in various orientations that are convenient for the sake of clarity in FIG. 4, and that at least some of these orientations may be different from one another. It is also noted that various elements are not shown to scale. For example, according to some embodiments, while layers 403*a*, 403*b* and 403*c* may be considered to be depicted by side elevation views of the layers on FIG. 4, electrodes 415 and resistive elements 409 may be considered to be depicted by perspective or plan views of the particular layers they are formed from. It is understood that these different orientations are provided to facilitate the discussion of these various elements and do not impose a limitation on the spatial or structural arrangements.

In some embodiments, the flexible circuit structure 401 may include at least one electrically nonconductive flexible layer 403 (electrically nonconductive substrate), at least one electrically conductive flexible circuit layer 404 coupled, directly or indirectly, to the at least one electrically nonconductive flexible layer 403. In some embodiments, the electrically conductive flexible circuit layer 404 may include conductive patterns including the plurality of resistive elements 409. In some embodiments, the flexible circuit structure 401 is electrically connected to a voltage or current measurement system (e.g., provided at least in part by (a) input-output device system 120, 320, (b) data processing device system 110, 310, or both (a) and (b), by the plurality of measurement conductors or leads 410*a*. In some embodiments, respective pairs of measurement conductors or leads 410*a* are arranged to sense voltage or current across each resistive element 409. In some embodiments, at least some of the measurement conductors or leads 410*a* are electrically connected to a respective conductive element 420. In some embodiments, measurement conductors or leads 410*a* are arranged to allow for a sampling of electrical voltage between each resistive element 409. These arrangements allow for the electrical resistance of each resistive element 409 to be accurately determined. The ability to accurately determine the electrical resistance of each resistive element 409 may be motivated by various reasons including determining temperature values at locations at least proximate the resistive element 409 based at least on changes in the resistance caused by convective cooling effects (e.g., as provided by blood flow). For example, the resistance of an electrically conductive metal (e.g., copper) changes based on the temperature of the electrically conductive metal. The rate of change is denominated as a temperature coefficient of resistance (TCR). In some embodiments, the resistance of various ones of the resistive members 409 may be related to the temperature of the resistor element 409 by the following relationship:

$R = R_0 * [1 + TCR * (T - T_0)]$, where:

R is a resistance of the electrically conductive metal at a temperature T;

$R_0$ is a resistance of the electrically conductive metal at a reference temperature $T_0$;

TCR is the temperature coefficient of resistance for the reference temperature (i.e., the TCR for copper is 4270 ppm at $T_0 = 0°$ C.); and T is the temperature of the electrically conductive metal.

In some embodiments, electrodes 415 are employed to selectively deliver particular energy (e.g., RF energy) to various tissue structures within a bodily cavity (not shown) (e.g., a tissue cavity such as an intra-cardiac cavity). The energy delivered to the tissue structures may be sufficient for ablating portions of the tissue structures. In various embodiments, the tissue structures are typically formed from non-fluidic tissue and the energy sufficient for ablating portions of the tissue structures is typically referred to as sufficient for tissue ablation. It is noted that energy sufficient for non-fluidic-tissue ablation may include energy levels sufficient to disrupt or alter fluidic tissue (e.g., blood) that may, for example, be located proximate the tissue structure. In many cases, the application of non-fluidic-tissue-ablative energy (i.e., energy that is sufficient to ablate non-fluidic tissue) to fluidic tissue, such as blood, is undesired when the energy is sufficient to disrupt or adversely impact a property of the fluidic tissue. For example, the application of non-fluidic-tissue-ablative energy to blood may be undesired when the energy is sufficient to cause various parts of the blood to coagulate in a process typically referred to as thermal coagulation. In this regard, some embodiments facilitate detection of conditions where an electrode configured to deliver non-fluidic-tissue-ablative energy may be in a configuration where it is not able to properly transmit such energy. In some embodiments, a detection of such a condition results in an error notification being transmitted or otherwise presented to a user or, in some embodiments, a restriction of that electrode from transmitting at least a portion of the non-fluidic-tissue-ablative energy. In some embodiments, a detection of such a condition results in an error notification being transmitted or otherwise presented to a user or, in some embodiments, a restriction of that electrode from being selected by a user action (e.g., a user selection of that electrode from a number of selectable electrodes to perform a particular function, such as transmitting at least a portion of the non-fluidic-tissue-ablative energy).

The energy delivered to the tissue may be delivered to cause monopolar tissue ablation, bipolar tissue ablation, or blended monopolar-bipolar tissue ablation by way of non-limiting example. In some embodiments, each electrode 415 is employed to sense an electrical potential in the tissue proximate the electrode 415. In some embodiments, each electrode 415 is employed in the generation of an intra-cardiac electrogram. In some embodiments, each resistive element 409 is positioned adjacent a respective one of the electrodes 415. In some embodiments, each of the resistive elements 409 is positioned in a stacked or layered array with a respective one of the electrodes 415 to form a respective one of the transducers 406. In some embodiments, the resistive elements 409 are connected in series to allow electrical current to pass through all of the resistive elements 409. In some embodiments, conductors or leads 410a are arranged to allow for a sampling of electrical voltage across each resistive element 409. This arrangement allows for the electrical resistance of each resistive element 409 to be accurately determined. The ability to accurately determine the electrical resistance of each resistive element 409 may be motivated by various reasons including determining temperature values at locations at least proximate the resistive element 409 based at least on changes in the resistance caused by convective cooling effects (e.g., as provided by blood flow). In various embodiments, some of the transducers 406 are controlled to provide one or more electrical signals to tissue (e.g., non-fluidic tissue associated with a tissue wall or fluidic tissue such as blood) and information or a derivative thereof is determined in response to the provided signals, the information or the derivative thereof indicating a result of an interaction between the one or more signals and the tissue. In various ones of these embodiments, the one or more signals may include one or more energy levels insufficient for tissue ablation.

In some embodiments in which the electrode-based device system 300 is deployed in a bodily cavity (e.g., when the electrode-based device system 300 takes the form of a catheter device system arranged to be percutaneously or intravascularly delivered to a bodily cavity), it may be desirable to perform various mapping procedures in the bodily cavity. For example, when the bodily cavity is an intra-cardiac cavity, a desired mapping procedure may include mapping electrophysiological activity in the intra-cardiac cavity. Other desired mapping procedures may include mapping of various anatomical features within a bodily cavity. An example of the mapping performed by devices according to various embodiments may include locating the position of the ports of various bodily openings positioned in fluid communication with a bodily cavity. For example, in some embodiments, it may be desired to determine the locations of various ones of the pulmonary veins or the mitral valve that each interrupts an interior surface of an intra-cardiac cavity such as a left atrium.

In some example embodiments, the mapping is based at least on locating bodily openings by differentiating between fluid and non-fluidic tissue (e.g., tissue defining a surface of a bodily cavity). There are many ways to differentiate non-fluidic tissue from a fluid such as blood or to differentiate tissue from a bodily opening in case a fluid is not present. Four approaches may include by way of non-limiting example, and, depending upon the particular approach(es) chosen, the configuration of transducers 406 in FIG. 4 may be implemented accordingly:

1. The use of convective cooling of heated transducer elements by fluid. An arrangement of slightly heated transducer elements that is positioned adjacent the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity may be responsive to electrical tissue impedance. Typically, heart tissue will have higher associated tissue impedance values than the impedance values associated with blood.

3. The use of a differing change in dielectric constant as a function of frequency between blood and tissue. A set of transducers positioned around the tissue that forms the interior surface(s) of the atrium and across the ports of the atrium monitors the ratio of the dielectric constant from 1 kHz to 100 kHz. Such may be used to determine which of those transducers are not proximate tissue, which is indicative of the locations of the ports.

4. The use of transducers that sense force (i.e., force sensors). A set of force detection transducers positioned around the tissue that forms the interior surface(s) of a bodily cavity and across the bodily openings or ports of the bodily cavity may be used to determine which of the transducers are not engaged with the tissue, which may be indicative of the locations of the ports.

Various ones of the above approaches may be used, at least in part, to determine proximity of a transducer to non-fluidic tissue or to fluidic tissue in some embodiments. Various ones of the above approaches may be used, at least in part, to determine contact between a transducer and non-fluidic tissue or contact between a transducer and fluidic tissue in some embodiments. Various ones of the above approaches may be used, at least in part, to determine an amount of an electrically conductive surface portion of an electrode that contacts non-fluidic tissue or contacts fluidic tissue in some embodiments. Various ones of the above approaches may be used, at least in part, to determine an amount of an electrically conductive surface portion of an electrode that is available to contact non-fluidic tissue or available to contact fluidic tissue in some embodiments.

Referring again to the medical device systems of FIGS. 3A and 3B, according to some embodiments, electrode-based device system 300 communicates with, receives power from or is controlled by a transducer-activation system 322, which may include a controller 324 and an energy source device system 340. In some embodiments, the controller 324 includes a data processing device system 310 and a memory device system 330 that stores data and instructions that are executable by the data processing device system 310 to process information received from other components of the medical device system of FIGS. 3A and 3B or to control operation of components of the medical device system of FIGS. 3A and 3B, for example by activating various selected transducers 306 to ablate tissue, sense tissue characteristics, et cetera. In this regard, the data processing device system 310 may correspond to at least part of the data processing device system 110 in FIG. 1, according to some embodiments, and the memory device system 330 may correspond to at least part of the memory device system 130 in FIG. 1, according to some embodiments. The energy source device system 340, in some embodiments, is part of an input-output device system 320, which may correspond to at least part of the input-output device system 120 in FIG. 1. Although only a single controller 324 is illustrated, it should be noted that such controller 324 may be implemented by a plurality of controllers. In some embodiments, the electrode-based device system 300 is considered to be part of the input-output device system 320. The input-output device system 320 may also include a display device system 332, a speaker device system 334, or any other device such as those described above with respect to the input-output device system 120. At least because the controller 324 includes the data processing device system 310, the controller 324 is referred to herein at times as being itself a data processing device system. For at least this reason, data processing device systems may equivalently be referred to as controllers according to some embodiments.

In some embodiments, particular portions (e.g., 309, where 309a, 309b are shown in FIGS. 3A and 3B) of the elongate members 304 may include or form at least a portion or an extension of conductors 317 that reside, at least in part (e.g., portion 309c), in the shaft member 316 and, at least in part, in the flexible catheter 314. For example, the conductors 410a, 410b in FIG. 4 may be or form a portion or an extension of conductors 317 in some embodiments. The conductors may be connected to the controller 324 at a connector 321 or other interface with the transducer-activation system 322 and provide communication pathways between at least the transducers 306 and the controller 324, according to some embodiments. In some embodiments in which particular portions of the elongate members 304 may include, or form a portion or an extension of, conductors 317, various particular portions of the elongate members 304 may be provided by flexible circuit structures (e.g., 401). In some embodiments, the elongate members 304 may terminate at connector 321 or other interface with the transducer-activation system 322, e.g., at the controller 324 or data processing device system 310, and provide communication or energy delivery pathways between at least the transducers 306 and the controller 324. In some embodiments, in which particular portions of the elongate members 304 may include or form a portion or an extension of conductors 317, the elongate members 304 may terminate at or in a housing physically coupled to shaft member 316. A non-limiting example of such a housing is a housing provided as part of a handle portion as described in U.S. Pat. No. 9,452,016, issued Sep. 27, 2016, such housing disclosures being hereby incorporated herein by reference in its entirety).

As discussed with respect to FIG. 4, each of various ones of the transducers 306, 406 includes an electrode 315, 415, according to some embodiments. In these various embodiments, each of at least some of the electrodes 315, 415 may include a respective energy transmission surface (e.g., energy transmission surface 319 in FIG. 3A) configured to transfer, transmit, or deliver energy, for example, to tissue. In some embodiments, at least some of the respective energy transmission surfaces 319 are configured to receive energy, for example, from tissue. Each of the energy transmission surfaces may be bound by a respective electrode edge 315-1 (e.g., FIG. 3A), 415-1 (e.g., FIG. 4).

In various embodiments, each of the electrodes 315 includes an electrically conductive surface portion (e.g., energy transmission surface 319) that, in some embodiments, has an electrical conductivity that is typically greater than that of fluidic and non-fluidic tissue. In some embodiments, the entirety of the electrically conductive surface portion is configured to contact or is configured to be available or exposed for contact with a contiguous portion of a non-fluidic tissue surface (e.g., a tissue surface that defines a tissue wall). Complete contact between the entirety of the electrically conductive surface portion and the non-fluidic tissue may be motivated for different reasons. For example, various desired characteristics required in a lesion formed in a tissue wall in a tissue ablation procedure may be dependent on the degree of intimate contact established between the electrically conductive surface portion of the electrode 315 and the tissue wall. For example, intimate contact may be required to form a lesion having sufficient transmurality to act as an effective electrophysiological activity block (e.g., a block capable of forming a barrier to spurious electrical signals causing fibrillation in an atrium). In some cases, complete contact between the entirety of the electrically conductive surface portion and the non-fluidic tissue may be desired to reduce the time required to form a lesion to a desired tissue depth under the influence of a given ablation energy level. In some cases, complete contact between the entirety of the electrically conductive surface portion of the electrode 315 and the non-fluidic tissue may be desired to reduce transmission of ablative energy to a surrounding fluidic tissue. In some cases, complete contact between the entirety of the electrically conductive surface portion of the electrode 315 and the non-fluidic tissue may be desired to reduce or eliminate exposure of the electrically conductive surface portion of the electrode 315 to surrounding fluidic tissue when the electrically conductive surface portion of the electrode 315 is positioned in contact with non-fluidic tissue. In some embodiments, the entirety of the portion of the electrically conductive surface of the electrode 315 that is configured to contact or is configured to be available or exposed (e.g., without some obstruction preventing at least some of the ability) to contact a tissue wall surface includes all of the electrically conductive surface. For example, this may occur when the electrically conductive surface has a generally planar form (e.g., a generally planar conductive surface provided by an electrode formed by flexible circuit fabrication techniques (e.g., electrode 415)). In some embodiments, the entirety of the portion of the electrically conductive surface of the electrode that is configured to contact or is configured to be available or exposed to contact a tissue wall surface includes some, but not all, of the electrically conductive surface. For example, this may occur when the electrode has a generally three-dimensional surface (e.g., a surface having a cylindrical, hemi-spherical or other three-dimensional form) with only a portion less than the entirety of the three-dimensional surface configured to contact or configured to be available or exposed for contact with a tissue surface wall.

In some embodiments, input-output device system 320 may include a sensing device system 325 configured to detect various characteristics or conditions including, but not limited to, at least one of tissue characteristics (e.g., electrical characteristics such as tissue impedance, tissue type, tissue thickness) and thermal characteristics such as temperature. Various other particular conditions may be detected by sensing device system 325 according to various embodiments. It is noted that in some embodiments, sensing device system 325 includes various sensing devices or transducers configured to sense or detect a particular condition while positioned within a bodily cavity. In some embodiments, at least part of the sensing device system 325 may be provided by electrode-based device system 300 (e.g., various ones of transducers 306). In some embodiments, sensing device system 325 includes various sensing devices or transducers configured to sense or detect a particular condition while positioned outside a given bodily cavity or even outside a body that includes the bodily cavity. In some embodiments, the sensing device system 325 may include an ultrasound device system or a fluoroscopy device system or portions thereof by way of non-limiting example.

The energy source device system 340 may, for example, be connected to various selected transducers 306 or their respective electrodes 315 to provide energy in the form of electrical current or energy (e.g., RF energy) to the various selected transducers 306 or their respective electrodes 315 to cause ablation of tissue. In this regard, although FIGS. 3A and 3B show a communicative connection between the energy source device system 340 and the controller 324 (and its data processing device system 310), the energy source device system 340 may also be connected to the transducers 306 or their respective electrodes 315 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 or their respective electrodes 315 (e.g., via one or more conductors (e.g., 317) through or within catheter 314, shaft member 316 or catheter sheath 312) that does not pass through the controller 324. In this regard, the energy source device system 340 may provide results of its delivering energy to, receiving energy from, or both delivering energy to and receiving energy from one or more of the transducers 306 or the respective electrodes 315 to the controller 324 (and its data processing device system 310) via the communicative connection between the energy source device system 340 and the controller 324.

The energy source device system 340 may, for example, provide energy in the form of electrical current to various selected transducers 306 or their respective electrodes 315. Determination of a temperature characteristic, an electrical characteristic, or both, at a respective location at least proximate each of the various transducers 306 or their respective electrodes 315 may be made under the influence of energy or current provided by the energy source device system 340 in various embodiments. Energy provided to an electrode 315 by the energy source device system 340 may in turn be transmittable by the electrodes 315 to adjacent tissue (e.g., tissue forming a tissue wall surface). In various embodiments, the transmittable energy is sufficient for tissue ablation. In some embodiments, the energy is insufficient for tissue ablation. The energy source device system 340 may include various electrical current sources or electrical power sources. In some embodiments, an indifferent electrode 326 is provided to receive at least a portion of the energy transmitted by at least some of the transducers 306 or their respective electrodes 315. Consequently, although not shown in FIGS. 3A and 3B, the indifferent electrode may be communicatively connected to the energy source device system 340 via one or more communication lines in some embodiments. The indifferent electrode 326 is typically configured to be positioned outside of a bodily cavity and may be positioned on an exterior body surface and, in some embodiments, although shown separately in FIGS. 3A and 3B, is considered part of and communicatively connected to the energy source device system 340.

In some embodiments, structure 308 may be delivered and retrieved at least in part via other forms of carrier members or shaft members, for example, a catheter sheath 312 (shown in FIG. 3A). Catheter sheath 312 includes a shaft member 313 with at least a first lumen extending between a proximal end portion of the shaft member 313 and a distal end portion of the shaft member 313 according to some embodiments. The shaft member 313 of the catheter sheath 312 is to be distinguished from the shaft member 316, which is deliverable through a lumen (e.g., the first lumen) of the catheter sheath 312 according to some embodiments. The shaft member 313 may be a wall of the catheter sheath 312. It is noted according to some embodiments that structure 308 is typically deliverable or retrievable (e.g., in an unexpanded or delivery configuration) through the first lumen of catheter sheath 312 by way of translation of at least part of the shaft member 316 through the lumen of the catheter sheath 312. In this regard, it may be understood that the structure 308 and the associated elongate members 304 are not coupled to catheter sheath 312 at a location that is fixed with respect to a reference location on the catheter sheath 312 (e.g., a distal end of the catheter sheath) since the structure 308 and associated elongate members 304 are free to translate through the catheter sheath 312. In some embodiments, at least part or a portion of each conductor 317 is located within at least a portion of the shaft member 313 that contacts a patient (e.g., when inserted into the body of the patient). In some embodiments, at least some or all of the plurality of conductors 317 are located within the first lumen of the shaft member 313. For example, in some embodiments in which at least some of the conductors 317 are located within the shaft member 316 of catheter 314, the at least some of the conductors are also located within the first lumen of shaft member 313 of catheter sheath 312 at least when catheter 314 is delivered through catheter sheath 312.

In some embodiments, the structure 308 provides expansion and contraction capabilities for a portion of a medical device (e.g., an arrangement, distribution or array of transducers 306). The transducers 306 may form part of, be positioned or located on, mounted or otherwise carried on the structure 308 and the structure 308 may be configurable to be appropriately sized to slide within catheter sheath 312 in order to be deployed percutaneously or intravascularly. FIG. 3A shows one embodiment of such a structure 308, where particular portions of the elongate members 304 (e.g., first portions or (e.g., also referred to as) first particular portions 309a that may be included in and collectively form structure 308), in some embodiments, are stacked in a stacked arrangement in the delivery or unexpanded configuration to facilitate fitting within the flexible catheter sheath 312 or to facilitate percutaneous or intravascular delivery of structure 308 to a bodily cavity. FIG. 3B shows an embodiment of structure 308 in an expanded or deployed configuration in which structure 308 has an arrangement of first particular portions 309a of elongate members 304 have enlarged or expanded to a size unsuitable to facilitate fitting with the catheter sheath 312 or unsuitable to facilitate percutaneous or intravascular delivery of structure 308 to a bodily cavity.

In some embodiments, each of the elongate members 304 includes a respective distal or second end 305 (only one called out in each of FIGS. 3A and 3B), a respective proximal or first end (e.g., 307, only one called out in each of FIGS. 3A and 3B), and various particular portions 309 positioned or arranged between the proximal end portion (e.g., 307) and the distal end portion 305. In some embodiments, each particular elongate member 304 includes a length extending along the elongate member 304 from the respective distal or second end 305 to the respective proximal or first end (e.g., 307) of the particular elongate member 304. In some embodiments, at least one particular portion 309 of each respective elongate member 304 may be located at a location where the structure 308 is coupled to the distal portion (e.g., a portion at least adjacent distal end 316b) of the shaft member 316. In some embodiments, at least a first particular portion 309 (e.g., first particular portion 309a bearing transducers 306) of each elongate member 304 extends outwardly from the shaft distal end 316b of the shaft member 316. In some embodiments, at least a first particular portion 309 (e.g., first particular portion 309a including transducers 306) of each elongate member 304 extends outwardly from the shaft distal end 316b of the shaft member 316, while concurrently, other particular portions 309 (e.g., second portions or second particular portions 309c) of the elongate member reside or are located within the elongated portion 316c of the shaft member 316. In some embodiments, at least a second particular portion (e.g., second particular portion 309c) of each elongate member resides or is located within the elongated portion 316c of the shaft member 316.

In some embodiments, the plurality of portions 309 of each particular elongate member 304 collectively provide a first or front surface or side 318a of the particular elongate member 304, the first or front surface or side 318a positionable to face away from an interior of the bodily cavity toward an interior tissue surface within the bodily cavity (e.g., FIGS. 2A and 2B). In some embodiments, the plurality of portions 309 of each particular elongate member 304 collectively provide a second or back surface or side 318b opposite across a thickness 327 of the particular elongate member 304 from the front surface or side 318a of the particular elongate member 304. In some embodiments, at least a portion of the front surface or side 318a of each particular elongate member 304 faces outwardly from an interior of the structure 308 when the structure 308 is in the deployed or expanded configuration (e.g., as shown in FIGS. 2A, 2B, 3B, 3C). A width 323 (e.g., FIG. 3B) of each respective elongate member 304 is perpendicular to and longer than the thickness 327 and perpendicular to the length of the respective elongate member 304, according to some embodiments. In the expanded or deployed configuration, it may be considered, according to some embodiments, that the width 323 of a respective elongate member 304 at a particular location along the elongate member 304 is perpendicular to a tangent of the length of the respective elongate member 304 at the particular location, since the respective elongate member 304 may exhibit curvature.

In some embodiments, at least part of the front surface 318a of each elongate member 304 is an outward-facing surface portion, each outward-facing surface portion positionable to face away from an interior of the bodily cavity and an interior of the structure 308 toward a tissue surface of a wall of the bodily cavity in a state in which the structure 308 is positioned in the bodily cavity in an expanded or deployed configuration (e.g., FIGS. 2A, 2B, 3B, 3C). Similarly, in some embodiments, all or part of the back surface 318b of each elongate member 304 is an inward-facing surface portion opposite the respective outward-facing surface portion, each inward-facing surface portion positionable to face toward an interior of the bodily cavity and an interior of the structure 308 in the state in which the structure 308 is positioned in the bodily cavity in an expanded or deployed configuration (e.g., FIGS. 2A, 2B, 3B, 3C).

In some embodiments, all or part of the front surface 318a of each elongate member 304 is an outward-facing surface portion, each outward-facing surface portion positionable to face outwardly or away from an interior of the structure 308 when the structure 308 is an expanded or deployed configuration (e.g., FIGS. 2, 3B, 3C). Similarly, in some embodiments, all or part of the back surface 318b of each elongate member 304 is an inward-facing surface portion opposite the respective outward-facing surface portion, each inward-facing surface portion positionable to face toward an interior of the structure 308 when the structure 308 is in an expanded or deployed configuration. In various embodiments, the various particular portions 309 of each particular elongate member 304 of the particular elongate member 304 collectively provide the front surface 318a, the back surface 318b, or both the front surface 318a and the back surface 318b of the particular elongate member 304.

In some embodiments, each elongate member 304 includes twisted portion 345 (only one called out in each of FIGS. 3A and 3B) at a location proximate at least the respective first particular portion 309a or at least proximate shaft distal end 316b of shaft member 316. The twisted portions 345 are located outside of the shaft member 316, beyond the shaft distal end 316b, when the structure 308 is in the expanded or deployed configuration (e.g., FIGS. 2A, 2B, 3B, 3C) and also when the structure 308 is in the unexpanded or delivery configuration (e.g., FIG. 3A). According to some embodiments, various particular portions (e.g., first particular portions 309a) of the elongate members 304 in the expanded or deployed configuration (e.g., FIGS. 2A, 2B, 3B, 3C) are fanned as compared to their corresponding positions in the unexpanded or delivery configuration (e.g., FIG. 3A). In some embodiments, various portions of the elongate members 304, such as twisted portions 345, may assist in or facilitate fanning of the elongate members 304 when the structure 308 moves from the delivery configuration (e.g., FIG. 3A) to the expanded or deployed configuration (e.g., FIGS. 2A, 2B, 3B, 3C). In various embodiments, each twisted portion 345 assumes a twisted configuration that includes about a quarter turn of rotation (approximately 90 degrees in some embodiments, less than 110 degrees in some embodiments, or less than 90 degrees in some embodiments). This relatively small amount of twist in portions 345 allows the first particular portions 309a to be oriented with their front surfaces 318a facing outwardly from an interior of the structure 308 when the structure 308 is in the expanded or deployed configuration. Alternatively or additionally, the relatively small amount of twist in portions 345 may facilitate a movement of the first particular portions 309a during a movement from the unexpanded or delivery configuration to the expanded or deployed configuration by allowing the portions 309b to be oriented in a favorable orientation to provide at least part of the fanning action. That is, while first particular portions 309a may be too stiff to adequately bend in the direction of fanning (e.g., across their width 323) in some embodiments, portions 309b are oriented by the non-helical twisted portion 345 in their preferred bending orientation (e.g., across their thickness 327) to at least in part provide the required fanning action, according to some embodiments. It is noted that portions 309b may be pre-formed to bend outwardly when portions 309b are advanced outwardly from the confines of the catheter sheath 312 to provide some degree of autonomous fanning capability to the first particular portions 309a, for example, as described in U.S. Pat. No. 9,492,227, issued Nov. 15, 2016, which is hereby incorporated herein by reference in its entirety. According to various embodiments, each of the twisted portions 345 may twist along a same rotational direction when structure 308 is in the unexpanded or delivery configuration, the same rotational direction being a same clockwise direction or a same counterclockwise direction. In various embodiments, the twisted portions 345 of the elongate members 304 are arranged in a collective twisted configuration when the structure 308 is in the unexpanded or delivery configuration.

As shown in FIG. 3A, according to some embodiments, particular portions (e.g., first particular portions 309a) of the elongate members 304 are arranged successively with respect to one another in a stacked arrangement (which may provide an example of what is sometimes referred to herein as a second stacked arrangement) when the structure 308 is in an unexpanded or delivery configuration. In various embodiments, the arrangement of the portions of the elongate members 304 in the stacked arrangement is an orderly one with each of the elongate members 304 arranged successively with respect to one another along a first direction (e.g., a stacking direction) represented by arrow 338a. It is understood that the first direction need not be a vertical or "up-down" direction but can also include other orientations. For instance, in some embodiments, various portions of elongate members 304, which are successively adjacent one another along the first direction 338a, may be stepped with respect to one another in one or more other directions. Thus, the set of elongate members 304 may be arranged in a non-stepped stacked arrangement fitting in a rectangular parallelepiped or may be arranged in a stepped stacked arrangement, for instance, fitting in a non-rectangular parallelepiped. As shown in FIG. 3A, according to some embodiments, particular portions (e.g., first particular portions 309a) of at least a set (which may provide an example of what is sometimes referred to herein as a second set) of at least three of the plurality of elongate members 304 are arranged front surface (e.g., 318a)-toward-back surface (e.g., 318b) in a stacked arrangement (which may provide an example of what is sometimes referred to herein as a second stacked arrangement) when the structure 308 is in a delivery or unexpanded configuration. According to some embodiments, each of the elongate members 304 is a strip-like member. According to some embodiments, each of the elongate members 304 is a planar member. Planar members may include at least one surface that is flat or generally flat, according to some embodiments. It is noted, according to some embodiments, that a planar member need not be flat (i.e., in two orthogonal directions) in all states or configurations. For example, a member including at least a flattened surface may be sufficiently flexible to impart some amount of curvature to the member and its flattened surface. Such a member is still considered to be, according to various embodiments, a planar member, since the flexibility of the member allows it to be bent into form in which the flattened surface may conform at least generally to a plane. According to some embodiments, each of the elongate members 304 is a non-planar member. For example, according to some embodiments, a non-planar member includes a member that does not include at least one flattened or planar surface or a member which does not have flexibility to be elastically manipulated (e.g., by bending) to include at least one flattened or planar surface.

In various embodiments, various portions of the elongate members 304 are successively arranged in an arrayed or stacked arrangement sized to be delivered through a lumen of catheter sheath 312, with each elongate member 304 positioned in the arrayed or stacked arrangement, such that the first surface 318a of the elongate member 304 is toward the second surface 318b of a first additional elongate member 304 in the arrayed or stacked arrangement, or the second surface 318b of the elongate member 304 is toward the first surface 318a of a second additional elongate member 304 in the arrayed or stacked arrangement, or both. For example, one of the outermost elongate members 304 in the arrayed or stacked arrangement is positioned in the arrayed or stacked arrangement such that its first surface 318a is toward the second surface 318b of another elongate member 304. Another of the outermost elongate member 304 is positioned in the arrayed or stacked arrangement such that its second surface 318b is toward the first surface 318a of another elongate member 304. An inboard elongate member 304 in the arrayed or stacked arrangement is positioned such that its first surface 318a is positioned toward the second surface 318b (not called out) of another elongate member 304 and the second surface 318b of inboard elongate member 304 is toward the first surface 318a of yet another elongate member 304. In some example embodiments, the first and the second surfaces 318a, 318b of the elongate members 304 are interleaved in the arrayed or stacked arrangement.

In various embodiments, each of the elongate members 304 has at least one surface that has a common characteristic with, or corresponds to, at least one surface of each of the other elongate members 304, and the elongate members 304 are arranged in an arrayed arrangement or stacked arrangement such that respective portions of the at least one surfaces of the elongate members 304 are successively arranged along the first direction of the stacked arrangement. In this respect, it is noted that the stacked arrangement does not require that the individual elongate members 304 actually rest on one another. In many instances of the stacked arrangement, the elongate members 304 or portions thereof may be separated from successively adjacent elongate members 304, or portions thereof for instance by space, such as in an embodiment of an interleaved arrangement. In some of these various embodiments, each at least one surface is a first surface, at least part thereof positionable adjacent, or proximate a tissue surface in the bodily cavity when the structure 308 is in the expanded or deployed configuration within the bodily cavity. In some of these various embodiments, each of at least the one surface is a first surface with a portion thereof that is positionable to face or contact a tissue surface in the bodily cavity when the structure 308 is in an expanded or deployed configuration within a bodily cavity. In some of these various embodiments, each at least one surface is a first surface that includes, or supports (i.e., directly or indirectly) one or more transducer elements. In some of these various embodiments, each at least one surface includes a first surface that includes, or supports (i.e., directly or indirectly) one or more transducer elements (e.g., an electrode) that are positionable adjacent a tissue surface in the bodily cavity when the structure 308 is in an expanded or deployed configuration within the bodily cavity. In some of these various embodiments, each at least one surface includes a first surface that includes, or supports (i.e., directly or indirectly) at least part of a flexible circuit structure. In some of these various embodiments, each at least one surface is a second surface with a portion thereof that is positionable to face away from a tissue surface in the bodily cavity when the structure 308 is in an expanded or deployed configuration within the bodily cavity. In some of these various embodiments, a respective portion of each at least one surface is arranged to face outwardly away from an interior or interior space of the structure 308 when the structure 308 is in an expanded or deployed configuration.

In some embodiments, various portions of the elongate members 304 are arranged successively adjacent one another when the structure 308 is in an unexpanded or delivery configuration. In some embodiments, various particular portions of the elongate members 304 face (and, in some embodiments, contact) each other when the structure 308 is in an unexpanded or delivery configuration. For example, a particular portion (e.g., a facing or contacting portion) of the front surface 318a of a first elongate member 304 may face (and, in some embodiments, contact) a particular portion (e.g., a facing or contacting portion) of the back surface 318b of a second elongate member 304 when the structure 308 is in an unexpanded or delivery configuration. In some embodiments, the respective portions (e.g., facing or contacting portions) of the first elongate member 304 and the second elongate member 304 are provided at least in part by respective ones of the first particular portions 309a of the first and the second elongate members 304. In some embodiments, at least the facing or contacting portion of the front surface 318a of the first elongate member 304 follows a contour of at least the facing or contacting portion of the back surface 318b of the second elongate member 304 when the structure is in an unexpanded or delivery configuration. For example, in the unexpanded or delivery configuration shown in FIG. 3A according to some embodiments, the first particular portions 309a of the elongate members 304 face (and, in some embodiments contact) each other in a front surface-toward-back surface manner and the contour of the front surface 318a of at least one of the elongate members 304 follows the contour of the back surface 318b of another of the elongate members 304.

In some embodiments, the respective facing or contacting portions of the first elongate member 304 and the second elongate member 304 are arranged front surface-toward-back surface as part of stacked arrangement when the structure 308 is in an unexpanded or delivery configuration. Depending on the degree of compacting of the elongate members in the stacked arrangement, partial or full separations or gaps can be present between two elongate members 304 of various ones of the successive pairs of elongate members 304 in the stacked arrangement (e.g., when the structure 308 is in an unexpanded or delivery configuration). Substantially uniform or non-uniform separations or varying sized separations between the two elongate members 304 of each successive pair of the elongate members 304 in the stacked arrangement can be present. In some example embodiments, various other elements may be disposed between two elongate members 304 of various ones of the successive pairs of the elongate members 304 in the stacked arrangement. For example, various transducer elements may be positioned between two elongate members 304 of various ones of the successive pairs of the elongate members 304 in the stacked arrangement. Various particular portions (e.g., first particular portions 309a) of the elongate members 304 can be linearly arrayed along the first direction (i.e., as represented by arrow 338a) in the stacked arrangement. In some embodiments, various particular portions (e.g., first particular portions 309a) of at least three elongate members 304 are linearly arrayed along a first direction (e.g., as represented by arrow 338a) in an arrayed arrangement when the structure is in the unexpanded or delivery configuration. In some embodiments, various particular portions (e.g., first particular portions 309a) of at least three elongate members 304 are successively arranged with respect to one another along a first direction (e.g., as represented by arrow 338a) in a stacked arrangement when the structure is in the unexpanded or delivery configuration. In some embodiments, various particular portions (e.g., first particular portions 309a) of at least three elongate members 304 are arranged front surface-toward-back surface in a stacked arrangement when the structure is in the unexpanded or delivery configuration.

Various particular portions of elongate members 304 (e.g., first particular portions 309a) may be substantially planar in form with or without some degree of curvature (e.g., curvature imparted by bending) (a) when the structure 308 is in the unexpanded or delivery configuration, (b) when the structure 308 is in the expanded or deployed configuration, or both (a) and (b). At least one of surfaces 318a and 318b need not be a flat surface. For example, at least one of surfaces 318a and 318b may include a convex or concave surface portion (e.g., across width 323) according to some embodiments. In embodiments where the electrodes 315 are considered part of their respective elongate members, the energy transmission surfaces 319 of such electrodes 315 may respectively represent an elevated surface portion of the respective front surface 318a of the respective elongate member 304, which is an example of a non-flat surface. However, in some embodiments, the energy transmission surfaces 319 may be flush (e.g., flush to the touch) with other surface portions of the respective elongate member 304, at least in some embodiments where the respective front surface 318a of the respective elongate member 304 is flat. In some example embodiments, various portions of the elongate members 304 have a shape that allows them to be successively stacked in a stacked arrangement. Stacked arrangements advantageously allow elongate members 304 to be arranged in a substantially spatially efficient manner to allow for delivery through bodily openings or catheter sheaths, thereby enabling reduced cross-sectional dimensions.

Advantageously, stacked portions of elongate members 304 allow for reduced bending stiffness about a bending axis arranged perpendicularly to the first or stacking direction of the portions of the elongate members 304 in stacked arrangement, especially when the portions of the elongate members are allowed to slide relatively with respect to one another during the bending. A reduced bending stiffness can facilitate the delivery of the stacked arrangement through catheter sheath 312 especially when catheter sheath 312 extends along a tortuous path to a bodily cavity.

The elongate members 304 may be constructed from various materials including, but not limited to, various metal and non-metal compositions, composite materials such as carbon fiber, or flexible PCB substrates. In some embodiments, each elongate member 304 includes a flexible printed structure (for example, as described with respect to FIG. 4). The elongate members 304 can include one or more material layers. The elongate members 304 may form an integral component of the transducer elements 306. The elongate members 304 may also include a support for a secondary assembly that carries the sensing and ablation transducer elements. An example of this is a stainless steel or Nitinol structure used to support transducer elements made with a flexible PCB circuit structure. In some embodiments, at least some of the elongate members 304 include resilient metallic portions. Suitable metallic materials may include stainless steel or Nitinol by way of non-limiting example. In some embodiments, structure 308 may alternatively or additionally include various members, components or assemblies other than the elongate members 304. For example, in some embodiments, the elongate members 304 may be supported on, located on, or provided on other structures including selectively expandable balloons. In some embodiments, the elongate members 304 include or take the form of flexible circuit structures (e.g., 401) which may be supported on, located on, or provided on other structures including selectively expandable balloons.

The transducers 306 may be arranged in various distributions or arrangements in various embodiments. In some embodiments, a set of one or more of the transducers 306 is located on structure 308. In some embodiments, structure 308 includes a particular portion (e.g., first particular portion 309a) of each particular elongate member 304 of the plurality of elongate members 304. According to some embodiments, at least parts (e.g., first particular portions 309a) of the elongate members 304 collectively form the structure 308. In some embodiments, a respective set of one or more of the transducers 306 is located on at least one portion (e.g., first particular portion 309a) of a respective one of the elongate members 304 of the plurality of elongate members. For example, in FIG. 3B, a set of one or more of the transducers 306 is shown located on the first particular portion 309a of each elongate member 304, which, in some embodiments, forms part of structure 308. In some embodiments, each particular elongate member 304 of the plurality of elongate members 304 comprises a length from a proximal end of the particular elongate member to the distal end 305 of the particular elongate member 304, and a plurality of sets of one or more of transducers 306 are located on distal portions (e.g., portions 309a) of the plurality of elongate members 304, each respective distal portion closer to, along the length of the respective elongate member 304, the respective distal end 305 of the respective elongate member 304 than at least some other particular portion of the respective elongate member (e.g., the respective twisted portion 345). In some embodiments, each particular elongate member 304 of the plurality of elongate members 304 comprises a length from the proximal portion 307, 307a, or 307b of the particular elongate member 304 to the distal end 305 of the particular elongate member 304, and a plurality of sets of one or more of transducers 306 are located on distal portions (e.g., portions 309a) of the plurality of elongate members 304, each respective distal portion closer to, along the length of the respective elongate member 304, the respective distal end 305 of the respective elongate member 304 than at least some other particular portion of the respective elongate member 304 (e.g., the respective twisted portion 345). In some embodiments, each respective distal portion is distinct from or does not include the respective distal end 305.

In some embodiments, various ones of the transducers 306 are spaced apart from one another in a spaced apart distribution as shown, for example, in at least FIGS. 3A and 3B at least when the structure 308 is in an expanded or deployed configuration. In some embodiments, various regions of space are located between various pairs of the transducers 306. For example, in FIG. 3B the transducer-based device system 300 includes at least a first transducer 306a, a second transducer 306b, and a third transducer 306c (all collectively referred to as examples of transducers 306). In some embodiments, each of the first, the second, and the third transducers 306a, 306b, and 306c are adjacent transducers in the spaced apart distribution. In some embodiments, the first and the second transducers 306a, 306b are located on different elongate members 304 (e.g., on the respective first portions 309a of the different elongate members 304) while the second and the third transducers 306b, 306c are located on a same elongate member 304 (e.g., on the first portion of 309a of the same elongate member 304). In some embodiments, a first region of space 350 is between the first and the second transducers 306a, 306b. In some embodiments, the first region of space 350 is not associated with any physical portion of structure 308. In some embodiments, a second region of space 360 associated with a physical portion of transducer-based device system 300 (e.g., a portion of an elongate member 304, such as at least part of the respective first portion 309a) is located between the second and the third transducers 306b, 306c. In some embodiments, each of the first and the second regions of space 350, 360 does not include a transducer or electrode thereof of electrode-based device system 300. In some embodiments, each of the first and the second regions of space 350, 360 does not include any transducer or electrode.

In various example embodiments, structures other than those shown in the accompanying figures may be employed to support or carry transducers of a transducer-based device such as a transducer-based catheter. For example, single tip catheters, basket catheters or balloon catheters may be used to distribute the transducers in a one-dimensional, two-dimensional or three-dimensional array.

In various example embodiments, the energy transmission surface 319 of each electrode 315 is provided by an electrically conductive surface. In some embodiments, each of the electrodes 315 is located on various surfaces of an elongate member 304 (e.g., front surfaces 318a or back surfaces 318b). In this regard, in some embodiments, each of one or more electrodes 315 is provided at least in part on the first side or front surface 318a, the second side or back surface 318b, or both the first side 318a and the second side 318b of a respective elongate member 304. In some embodiments, each of one or more electrodes 315 is located on one, but not both of the front surface 318a and back surface 318b of a respective elongate member 304. For example, various electrodes 315 may be located only on the respective front surfaces 318a of each of the various ones of the elongate members 304. Three of the electrodes 315 are identified as electrodes 315a, 315b, and 315c in FIG. 3B. Three of the energy transmission surfaces 319 are identified as 319a, 319b, and 319c in FIG. 3B. In various embodiments, it is intended or designed to have the entirety of each of various ones of the energy transmission surfaces 319 be available or exposed (e.g., without some obstruction preventing at least some of the ability) to contact non-fluid tissue at least when structure 308 is positioned in a bodily cavity in the expanded configuration. In various embodiments, it is intended or designed to have no portion of each of at least one of the energy transmission surfaces 319 contact fluidic tissue when the at least one of the energy transmission surfaces 319 contacts a contiguous portion of a non-fluidic tissue surface (e.g., a tissue surface that defines a tissue wall).

In some embodiments, like those shown in FIG. 3B, the respective first particular portions 309a of various ones of the elongate members 304 are angularly arranged with respect to one another about a first axis 335a when structure 308 is in the expanded or deployed configuration. In some embodiments, the first axis 335a is oblique with respect to an extension direction of a second axis 335b (e.g., in FIG. 3B) in which the shaft member 316 extends at the distal end 316b. In this regard, the second axis 335b may be collinear with the longitudinal axis 339d of the shaft member 316 at the distal end 316b of the shaft member 316. The second axis 335b (or longitudinal axis 339d when collinear with the second axis 335b) may extend through a center (e.g., centroid or geometric center) of a cross-section of the shaft member 316 at or adjacent the distal end 316b of the shaft member 316. It is understood that that shaft member 316 is a flexible member in some embodiments. Accordingly, the longitudinal axis 339d of shaft member 316 need not be straight within various portions of shaft member 316, but rather may follow a bend associated with these various portions of shaft member 316. Nonetheless, the longitudinal axis 339b extends outwardly in a straight-line path from the proximal and distal ends 316a, 316b of shaft member 316 (for example, as shown in FIG. 3B).

The terms "radially arranged" and "angularly arranged" may be used interchangeably, to refer to an arrangement that, in some embodiments, is the same or similar to lines of longitude distributed at least partially (e.g., hemispherically) about an axis (e.g., polar or other axis) of a body (e.g., body of revolution), which may, or may not, be spherical.

As shown in FIG. 3C, in some embodiments, at least one of the elongate members 304 crosses another of the elongate members 304 (for example, in an X configuration) (only two elongate members 304 called out in FIG. 3C for clarity) at a location proximate a first axis 335a (extending into and out of the page of FIG. 3C and illustrated with an "+" in FIG. 3C). In some embodiments, various ones of the elongate members 304 are fanned about first axis 335a. In some embodiments, first axis 335a passes through a plurality of spaced apart locations along the respective length of each of at least some of the elongate members 304 when structure 308 is in the expanded or deployed configuration. In various embodiments, first axis 335a may pass through two or more spaced apart locations along the respective length of each of at least one of the elongate members 304.

In some embodiments, each of the at least some of the plurality of elongate members 304 includes a curved portion 337 (two called out in FIG. 3B) arranged to extend along at least a portion of a respective curved path that intersects the first axis 335a at each of a respective at least two spaced apart locations along first axis 335a when the structure 308 is in an expanded or deployed configuration. In various embodiments, a curved portion 337 of an elongate member 304 may extend entirely along, or at least part way along a respective curved path that intersects the first axis 335a at each of a respective at least two spaced apart locations along first axis 335a when the structure 308 is in an expanded or deployed configuration. In some embodiments, each of the elongate members 304 includes a curved portion 337 including a curvature configured to cause the curved portion 337 to extend along at least a portion of a curved path, the curvature configured to cause the curved path to intersect the first axis 335a at each of a respective at least two spaced apart locations along the first axis 335a when structure 308 is in an expanded or deployed configuration. In some embodiments, the curved path is defined to include an imagined extension of the curved portion 337 along the curved portion's extension direction while maintaining the curved portion's curvature (e.g., radius of curvature or change in radius of curvature) at a location where the curved portion 337 ends and the imagined extension begins. In some embodiments, each curved portion 337 may extend entirely along, or at least part way along, the respective curved path to physically intersect at least one of the respective at least two spaced apart locations along the first axis 335a. In some particular embodiments, no physical portion of a given elongate member 304 of an employed structure intersects some of the at least two spaced apart locations along the first axis 335a intersected by the respective curved path associated with the curved portion 337 of the given elongate member 304. In various embodiments, the curved path is an arcuate path. In various embodiments, at least the portion of the curved path extended along by curved portion 337 is arcuate. In some embodiments, at least a first elongate member 304 crosses a second elongate member 304 (e.g., in an X configuration) at each of at least one of the respective at least two spaced apart locations along the first axis 335a intersected by at least the portion of the respective curved path extended along by the curved portion 337 of the second elongate member 304 when the structure 308 is in the expanded or deployed configuration. In some embodiments, at least a first elongate member 304 crosses a second elongate member 304 at each of the respective at least two spaced apart locations along the first axis 335a intersected by at least the portion of the respective curved path extended along by the curved portion 337 of the second elongate member 304 when the structure 308 is in an expanded or deployed configuration. In various embodiments, each respective curved portion 337 is arranged to extend along at least a portion of a respective curved path that intersects the first axis 335a at each of a respective at least two spaced apart locations along first axis 335a when the structure 308 is in an expanded or deployed configuration.

In various embodiments, various particular portions of all of the plurality of elongate members 304 are circumferentially arranged about first axis 335a when the structure 308 is in an expanded or deployed configuration. For example, when the structure 308 is the expanded or deployed configuration, at least respective parts of the elongate members 304 (e.g., at least the first particular portion 309a or the curved portion 337) are circumferentially arranged about the first axis 335a, in the same or similar manner as lines of longitude about an axis of a body, which body may, or may not, be spherical. In some embodiments, at least one portion (e.g., the first particular portion 309a or the curved portion 337) of each of the elongate members 304 extends like a line of longitude about the structure 308 when the structure is in the deployed or expanded configuration. In some embodiments, at least one portion (e.g., at least the first particular portion 309a or the curved portion 337) of each elongate member 304 is not arranged in a helical configuration when the structure 308 is in an expanded or deployed configuration. It is noted in various embodiments that various particular portions of the elongate members may include configurations in each of the delivery and the deployed configurations that differ from one another on aspects other than differences in size. Other aspects can include inherent differences in structure. For example, according to some embodiments, the first particular portions 309a of the elongate members 304 are arranged like lines of longitude in the expanded or deployed configuration shown in FIG. 3B and are arranged in a stacked configuration in an unexpanded or delivery configuration shown in FIG. 3A. Without limitation, other arrangements of some of the various particular portions of the elongate members 304 are possible in various embodiments.

In some embodiments, each of the elongate members 304 includes a respective portion (e.g., at least part of first particular portion 309a or at least part of curved portion 337) radially spaced from the first axis 335a when the structure 308 is in an expanded or deployed configuration, the respective portions of the elongate members 304 circumferentially arranged about the first axis 335a when the structure is in the expanded configuration. Similarly, in various embodiments, at least some of the electrodes 315 are radially spaced about or from a first axis 335a when structure 308 is in an expanded or deployed configuration. In various embodiments, at least some of the electrodes 315 are circumferentially arranged about first axis 335a when structure 308 is in the deployed configuration. For example, various ones of the electrodes 315 are circumferentially arranged about first axis 335a in the expanded or deployed configuration in at least some of the embodiments associated with various ones of at least FIG. 3B. It is understood that although electrodes 315 are referred to in these described embodiments, the same analysis applies to the corresponding transducers 306 in some embodiments. In various embodiments, the electrodes 315 are arranged such that the first axis 335a passes through, or alternatively does not pass through a particular electrode (e.g., a central electrode). The presence or non-presence of such a particular electrode may be dependent on various factors including a required size of the device and particular anatomy characteristics into which the device is deployed. For example, different bodily cavities have different sizes and shapes and, therefore, different sizes and shapes of various parts of the transducer-based device system 300 (e.g., structure 308) may be appropriate to match the different sizes and shapes of the bodily cavities, according to some embodiments. Different bodily cavities may have different anatomical features or different positionings of various anatomical features. Accordingly, in some embodiments, it may be beneficial to have an arrangement of transducers or electrodes in which an electrode intersected by first axis 335a exists. In other applications, it may be beneficial to have an arrangement of transducers or electrodes in which an electrode intersected by first axis 335a does not exist.

It may be noted that distances between adjacent ones of the elongate members 304 shown in at least FIG. 3B vary as elongate members 304 extend toward first axis 335a when structure 308 is in the deployed configuration. In some cases, the varying distances between adjacent elongate members 304 in an expanded or deployed configuration may give rise to shape, size or dimensional constraints for the electrodes 315 located on the elongate members 304. In some cases, the overlapping portions of various ones of the elongate members 304 in the deployed configuration may give rise to shape, size or dimensional constraints for the electrodes 315 located on the portions of the various ones of the elongate members 304. For example, it may be desirable to reduce a surface area of an electrode adjacent an overlap region on an overlapped elongate member to accommodate the reduced exposed surface area of the overlapped elongate member in the region adjacent the overlap region.

In various embodiments, the respective shape of various electrically conductive surfaces (e.g., energy transmission surfaces 319) of various ones of the electrodes 315 vary among the electrodes 315. In various embodiments, the respective shape of various electrically conductive surfaces (e.g., energy transmission surfaces 319) of various ones of the electrodes 315 vary among the electrodes 315 in accordance with their proximity to first axis 335a. In various embodiments, one or more dimensions or sizes of various electrically conductive surfaces (e.g., energy transmission surfaces 319) of at least some of the electrodes 315 vary among the electrodes 315. In various embodiments, one or more dimensional sizes of various electrically conductive surfaces (e.g., energy transmission surfaces 319) of at least some of the electrodes 315 vary in accordance with their proximity to first axis 335a. The shape or size variances associated with various ones of the electrodes 315 may be motivated for various reasons. For example, in various embodiments, the shapes or sizes of various ones of the electrodes 315 may be controlled in response to various ones of the aforementioned size or dimensional constraints.

The ever increasing demand for short procedure times (and reduced patient risk associated therewith) as well as enhanced efficacy continues to place increased demands to activate greater numbers of transducers (e.g., 306) or activate various transducers (e.g., 306) in accordance with increased power levels. For example, in tissue ablation procedures, complex ablation patterns may require larger numbers of ablating transducers to provide the necessary spatial resolution necessary to efficiently complete the ablation pattern. Further, demands for completing the necessary ablations in shorter times often drive the demand to employ higher power levels. Other diagnostic or treatment procedures can also place similar demands on the activation of various transducers.

Power levels, however, cannot typically be increased without limit. Various safety requirements that pertain to the health of the care provider, the patient, or both may require consideration. Typically, the use of increased power levels leads to an increase in the temperature of various components, possibly to unsafe levels if left unchecked. Various regulatory standards may impose restrictions or limits on a temperature that a particular component may reach. For example, IEC 60601-1:2005/A1:2012 (*Medical Electrical Equipment—General Requirements*) subclause 11.1.2.2 imposes a requirement that the temperature of components that are not intended to deliver heat to a patient not exceed a specified limit. According to IEC 60601-1:2005/A1:2012, the specified limit depends on the material type of the component and the length of time for which the component can remain in contact with the patient. This requirement applies in normal operating conditions and in single fault conditions (e.g. failure of a cooling circuit). Typically, compliance with the requirement is evaluated by operating the system (e.g., 100, 300, or 400) in the least favorable operating conditions and measuring the temperature of the components that would normally contact the patient. The requirement is met if all component temperatures are below their specified limits in these conditions.

In various catheter-based procedures, a catheter including an elongated shaft member which is percutaneously, intravascularly or otherwise deliverable through a bodily opening leading to a bodily cavity within a patient is employed. The elongated shaft member (e.g., 313 or 316) is in many cases an example of a component that includes a portion of which that contacts the patient (e.g., when inserted into the body of the patient), and the portion of which typically is not configured to intentionally apply heat to the patient (e.g., the portion of the elongated shaft member is not required by a particular diagnostic or therapeutic procedure and is not configured to intentionally apply particular heat to the patient). In this regard, the portion of the shaft member (e.g., 313 or 316) may not include any therapeutic transducer (e.g., any ablation or other therapeutic transducer) or may not include any transducer, including any therapeutic transducer, e.g., that applies heat upon activation. However, in some embodiments, the portion of the shaft member (e.g., 313 or 316) may include one or more conductors within it that deliver electrical energy to one or more transducers, e.g., located beyond the portion of the shaft member. For example, when various conductors (e.g., 317), or at least respective parts thereof, are located within the portion of the shaft member, (e.g., 313 or 316) resistive heating associated with the delivery of electric current through various ones of the conductors may cause the surrounding portion of the shaft member to heat up in an undesired manner. In many medical device systems (e.g., 100, 300, or 400) which deliver energy sufficient for tissue ablation, the least favorable operating condition that can lead to undesired heating of the shaft member may be during the delivery of high levels or maximum levels of ablative power to the patient via at least some (e.g., one or more) of a plurality of transducers (e.g., 306). This operating condition typically causes relatively large increases in the shaft member temperature due to the non-zero resistance of the conductors located with the shaft member (e.g., 313 or 316).

IEC 60601-1:2005/A1:2012, for example, provides the allowable maximum temperature for skin contact for various durations and materials. For instance, metal and liquid applied parts having contact with a patient (a) for less than one minute can have a maximum allowable temperature of 51 degrees Celsius, (b) for greater than or equal to one minute and less than ten minutes can have a maximum allowable temperature of 48 degrees Celsius, and (c) for greater than or equal to ten minutes can have a maximum allowable temperature of 43 degrees Celsius. For another example, glass, porcelain, and vitreous material applied parts having contact with a patient (a) for less than one minute can have a maximum allowable temperature of 56 degrees Celsius, (b) for greater than or equal to one minute and less than ten minutes can have a maximum allowable temperature of 48 degrees Celsius, and (c) for greater than or equal to ten minutes can have a maximum allowable temperature of 43 degrees Celsius. For yet another example, molded rubber, plastic, rubber, and wood applied parts having contact with a patient (a) for less than one minute can have a maximum allowable temperature of 60 degrees Celsius, (b) for greater than or equal to one minute and less than ten minutes can have a maximum allowable temperature of 48 degrees Celsius, and (c) for greater than or equal to ten minutes can have a maximum allowable temperature of 43 degrees Celsius.

Figure 5A:
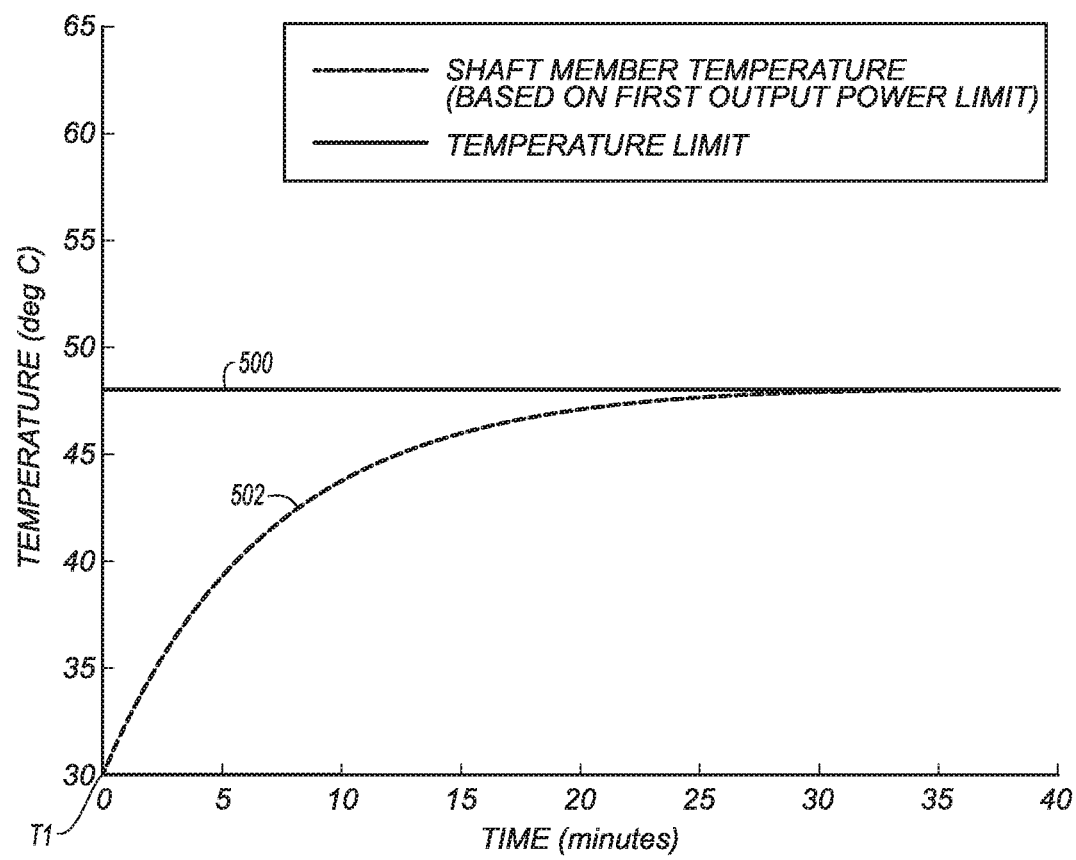
FIG. 5A shows a graph in which an output power has been limited based on a first output power limit to cause a temperature of a portion of a shaft member of a medical device system to not exceed a particular temperature limit, according to some embodiments.

One approach to prevent the portion of the shaft member (e.g., 313 or 316) from reaching an unacceptable temperature is to limit the maximum power dissipation in the portion of the shaft member (e.g., 313 or 316) by limiting the maximum output power that can be delivered via a set of the conductors (e.g., 317) located with the portion of the shaft member. FIG. 5A shows a graph in which the output power has been limited by a first output power limit to cause a temperature (e.g., along temperature curve 502) of a portion of the shaft member (e.g., 313 or 316) to not exceed a particular temperature limit 500 (approximately 48 degree Celsius in this exemplary illustration). According to FIG. 5A, the applied output power (e.g., as limited by the first output power limit) is applied for a particular time period sufficient to cause the temperature (e.g., along temperature curve 502) of the portion of the shaft member (e.g., 313 or 316) to reach a first steady-state temperature (e.g., a portion of the temperature curve 502 that asymptotically approaches the horizontal line representing the temperature limit 500) (e.g., approximately 48 degree Celsius, according to some embodiments), the first steady-state temperature determined or considered insufficient (e.g., pursuant to IEC 60601-1: 2005/A1:2012 or other determination) to thermally harm the patient. It is noted, according to some embodiments, that temperatures that exceed the temperature limit 500 may be determined sufficient to thermally harm the patient. From a mathematical perspective, as shown in FIG. 5A, since, e.g., the temperature curve 502 might be deemed to asymptotically approach, but not mathematically achieve the temperature limit 500, the phrases, 'reach the steady-state temperature', 'transition to a steady-state temperature', and similar phrases as used in such a context herein may be deemed to include, in some embodiments, the point in time at which the slope of the temperature vs. time curve (e.g., as represented by temperature curve 502) of the portion of the shaft member essentially becomes flat or zero, such as, for example, a slope less than 0.1 degrees Celsius per minute or less than 0.01 degrees Celsius per minute or lower according to some embodiments. On the other hand, the steady-state temperature may be deemed, in some embodiments, to be parallel to, but just under the temperature limit (e.g., limit 500). In such cases, the temperature vs. time curve (e.g., as represented by temperature curve 502) of the portion of the shaft member may be deemed to actually achieve a zero slope at the steady-state temperature, but such steady-state temperature is just under the temperature limit. Mathematical considerations aside, however, in practice, trivial variations in temperature occur even at steady-state, and the invention is not limited to any particular characterization of the close relationship between the temperature of the portion of the shaft member (e.g., temperature curve 502) at steady-state with respect to a temperature limit (e.g., limit 500).

It is noted, for example, as per the graph of FIG. 5A, that, in some cases in which long thermal time constants are involved, it may take significant time (e.g., several tens of minutes) for the portion of the shaft member to reach thermal equilibrium at the first steady-state temperature. It is noted that typically according to some embodiments, the first output power limit may be determined for a particular set of least favorable conditions. For example, if various conductors in the shaft member undergo cooling by delivery of a coolant or other fluid through the shaft member, such delivery may be disabled to mimic various fault conditions that would thus cause the portion of the shaft member to increase to a higher than normal temperature. In some cases where multiple coolant delivery channels are provided, a single one of the multiple channels may be disabled to provide a single fault condition.

Accordingly, the graph of FIG. 5A corresponds to the first output power limit that may be employed to prevent the portion of the shaft member (e.g., 313 or 316) from exceeding its required temperature limit 500 even when the portion of the shaft member has reached a steady-state temperature under the influence of the applied maximum output power. In some embodiments, the first output power limit is related to the sum of the squares of electrical current signals that are provided through the shaft member (e.g., each current signal having a respective value that is multiplied by the same respective value). Typically in ablation type systems (e.g., 100, 300, or 400), the provided electrical current signals have the highest values when they are employed to cause energy sufficient to cause tissue ablation to be delivered. Accordingly, in systems (e.g., 100, 300, or 400) that employ a plurality of transducers (e.g., 306) the ability to concurrently or simultaneously activate all or particular groups of the transducers (e.g., 306) may be impacted by the first output power limit. That is, if a particular requirement to concurrently activate a particular number of the transducers (e.g., 306) requires a particular set of electrical current signals to be delivered via a set of the conductors (e.g., 317) located in the shaft member (e.g., 313 or 316), the delivery of the particular set of electrical current signals may lead to a condition in which the temperature of the portion of the shaft member (e.g., 313 or 316) would exceed the temperature limit. This condition, in turn, may limit the number of transducers (e.g., 306) that can be concurrently activated and, thus, may lead to a requirement for sequential activation of smaller sets (i.e., sets with fewer numbers) of the transducers to reduce the electrical current delivered at one time and, consequently, reduce the increase in temperature of the portion of the shaft member that would be caused by the delivery of higher electrical current if all transducers were to be activated concurrently. It is noted that limiting the number of transducers (e.g., 306) that can be concurrently activated can increase the overall time of the procedure, which can result in increased risk for the patient and increased financial costs. This problem becomes compounded as systems (e.g., 100, 300, or 400) with greater numbers of transducers (e.g., 306) are employed and the desire to concurrently activate increasing numbers of the transducers increases. Accordingly, various embodiments of the present invention may advantageously provide safer ways to concurrently activate a large number of transducers that might otherwise, absent precautions, exceed a temperature limit (e.g., at least by controlling transducer activation durations or start times, according to some embodiments as described herein).

Figure 5B:
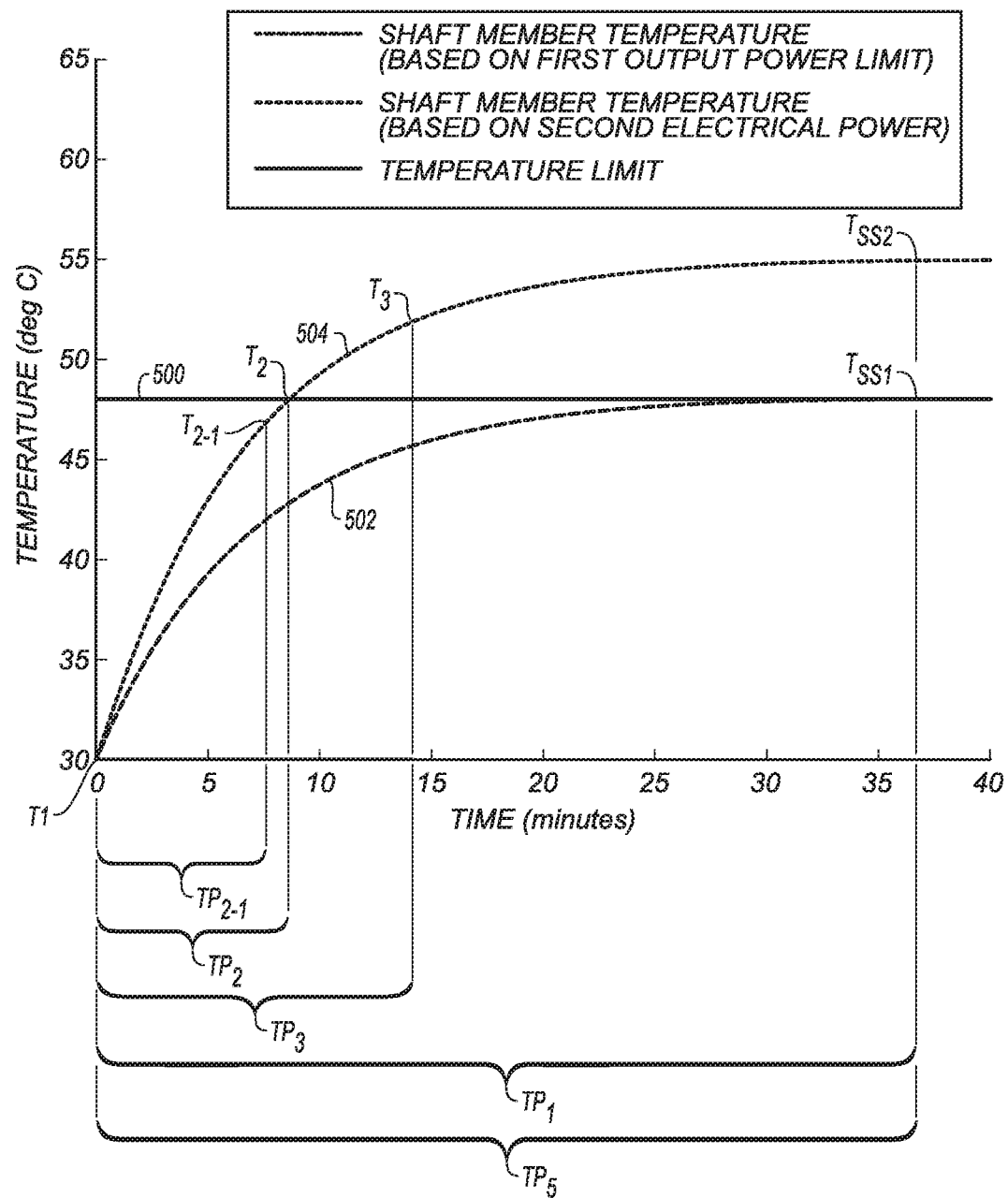
FIG. 5B shows a graph of the temperature of a shaft member of a medical device system that would result under the influence of an applied second electrical power that is greater than the first output power limit, according to some embodiments.

For example, FIG. 5B is a graph of the temperature of the shaft member (e.g., 313 or 316) operated in accordance with some embodiments. FIG. 5B includes the temperature limit 500 (i.e., shown as a horizontal line) of FIG. 5A, and, for ease of the following discussion, also includes the shaft member temperature (e.g., represented by temperature curve 502 of FIG. 5A) that was generated under the influence of the first output power limit. FIG. 5B shows the temperature curve 504 that would result under the influence of an applied second electrical power that is greater than the first output power limit, as might occur when a larger number of transducers are concurrently activated as compared to the number of transducers that may be concurrently activated to produce temperature curve 502 (although other reasons for a greater second electrical power exist, such as merely providing more power to a same or fewer number of transducers).

In a manner similar to FIG. 5A, FIG. 5B shows the temperature curve 504 reaching a steady-state value under the influence of the greater second electrical power. It is noted that, although operation with the increased second electrical power (i.e., increased over the first output power limit) would allow for the concurrent activation of a greater number of the transducers (e.g., 306), at least the steady-state portion of the temperature curve 504 of the portion of the shaft member (e.g., 313 or 316) would exceed the temperature limit 500 and thus possibly could be determined to cause thermally-induced tissue cellular damage (for example, based at least on contact between the portion of the shaft member and tissue), if the greater second electrical power was to be delivered for at least a sufficient amount of time.

In some embodiments, this sufficient amount of time is dependent on a relatively long thermal time constant associated with the representative system (e.g., 100, 300, or 400). This relatively long thermal time constant allows for a particular amount of time to elapse from the start of delivery of various electrical current signals via various conductors (e.g., 317) in the shaft member, before the temperature limit 500 is exceeded. For example, FIG. 5B indicates that the temperature limit 500 is not exceeded by curve 504 until approximately eight minutes after the start of the delivery of the greater second electrical power. The present inventors recognized that such an amount of time may be utilized to concurrently activate a greater number of transducers for a shorter amount of time, while maintaining the temperature of the portion of the shaft member (e.g., 313 or 316) safely below the temperature limit (e.g., 500). Many successful results may be achieved by transducer activations that last for less than the period of time for which the temperature of the portion of the shaft member (e.g., 313 or 316) is below the temperature limit (e.g., 500), e.g., less than the eight minutes shown in FIG. 5B. For example, in various transducer activation procedures (e.g., occurring during a tissue ablation procedure), electrical current is delivered to the transducers for three minutes or less. Electrical current may be delivered to the transducers for five minutes or less in some transducer activation procedures, or for six minutes or less in other transducer activation procedures or for seven minutes or less in yet other transducer activation procedures.

Advantageously, operation of the system (e.g., 100, 300, or 400) is improved according to some embodiments by either actively monitoring or predicting (e.g., based on a predetermined model) the temperature of the portion of the shaft member (e.g., 313 or 316) and then allowing the output power to be increased (e.g., to levels above the first output power limit) for particular periods of time that do not result in the temperature (e.g., along temperature curve 504) of the portion of the shaft member (e.g., 313 or 316) exceeding the temperature limit (e.g., 500), while simultaneously allowing a greater number of the transducers (e.g., 306) to be concurrently activated or larger amount of power to be delivered.

For example, consider a case where it is desired to select five transducers (e.g., 306) for concurrent activation, each of the transducers having a respective current limit of 0.5 A associated with the activation thereof. If the first output power limit equates or correlates to a squared current limit of 1.0 $A^2$, then concurrently activating all five of the transducers (e.g., 306) would exceed the squared current limit (i.e., $5*(0.5 A)^2=1.25 A^2$). If all five of the transducers (e.g., 306) were to be activated (e.g., for three minutes by way of non-limiting example), the first output power limit would be exceeded. Accordingly, in some embodiments, the five transducers may be broken into two sequentially activated subsets of, e.g., three transducers and then two transducers. Such an arrangement may be beneficial in cases where it is required that the first output power limit not be exceeded, but overall activation time for the five transducers would be increased to six minutes (three minutes for the group of three transducers followed by three minutes for the group of two transducers). In at least some embodiments where it is acceptable to exceed the first output power limit so long as the temperature (e.g., along temperature curve 504) of the portion of the shaft member (e.g., 313 or 316) does not exceed the temperature limit (e.g., 500), at least some embodiments concurrently activate all five of the transducers, but for only the three minutes, which would keep the temperature (e.g., along temperature curve 504) of the portion of the shaft member (e.g., 313 or 316) well below the temperature limit 500 in the example of FIG. 5B. Such an arrangement reduces the overall activation time of the five transducers from six minutes, in the case where two subsets of the five transducers are sequentially activated, to three minutes.

Accordingly, in some example embodiments, the first output power limit may be defined as a level of power, that, if delivered via a first set of the plurality of conductors (e.g., 317) to a first set of the plurality of transducers (e.g., 306) for a first time period $TP_1$, causes a portion of the shaft member (e.g., 313 or 316) to transition from a first temperature $T_1$ to a first steady-state temperature $T_{SS1}$ immediately upon conclusion of the first time period $TP_1$, the first steady-state temperature insufficient, or determined to be insufficient to cause (via the portion of the shaft member) thermally-induced tissue cellular damage or thermally-induced tissue cellular necrosis. For example, in FIG. 5B, a first output power limit is a level of power, that if delivered via a first set of the plurality of conductors (e.g., 317) to a first set of the plurality of transducers (e.g., 306) for a first time period $TP_1$ causes a temperature (e.g., along temperature curve 502) of a portion of the shaft member (e.g., 313 or 316) to transition from a first temperature $T_1$ (approximately 30 degrees Celsius) to a first steady-state temperature $T_{SS1}$ (approximately 48 degrees Celsius) immediately upon conclusion of the first time period $TP_1$, the first steady-state temperature $T_{SS1}$ being insufficient, or determined or considered to be insufficient (for example, according to the determination of IEC 60601-1:2005/A1:2012 or some other requirement) to cause thermally-induced tissue cellular damage or thermally-induced tissue cellular necrosis (e.g., via at least contact with the portion of the shaft member). In some embodiments, the first temperature $T_1$ is a temperature of the portion of the shaft member at the start of the first time period $TP_1$. In the illustrated embodiments associated with FIG. 5B, the first temperature $T_1$ is an ambient temperature (e.g., a generally consistent surrounding temperature) of at least the portion of the shaft member (e.g., 313 or 316), and the first time period $TP_1$ is approximately 37 minutes, but it is understood that other first temperatures and first time periods may be employed in other embodiments. In some embodiments, the first temperature $T_1$ is a temperature that is less than or equal to a temperature of a portion of the body of the patient that at least part of the shaft member (e.g., 313 or 316) is percutaneously deliverable through. In some embodiments, the first temperature $T_1$ may represent a state in which the portion of the shaft member (e.g., 313 or 316) is unheated or substantially unheated by delivery of electrical power, e.g., to any of one or more transducers, through any or one or more conductors (e.g., 317) within the shaft member (e.g., 313 or 316). In some embodiments, the first temperature $T_1$ is a temperature of the portion of the shaft member (e.g., 313 or 316) prior to the controller (e.g., 324) causing electrical power to be delivered to any transducer of the plurality of transducers (e.g. 306). In some embodiments, the first temperature $T_1$ is a temperature of the portion of the shaft member (e.g., 313 or 316) prior to the activation of any one of the plurality of transducers (e.g., 306). In some embodiments, the first temperature $T_1$ is a temperature of the portion of the shaft member (e.g., 313 or 316) prior to the controller (e.g., 324) causing electrical power to be delivered to any particular transducer of the plurality of transducers (e.g. 306) to cause the particular transducer to emit energy sufficient for tissue ablation. In some embodiments, as discussed in more detail below, the first temperature $T_1$ may represent a state in which the portion of the shaft member (e.g., 313 or 316) is heated from a prior delivery of electrical power, e.g., to one or more transducers (e.g., 306) through one or more conductors (e.g., 317) within the shaft member (e.g., 313 or 316).

In some embodiments, a controller (e.g., 324) is configured to cause delivery, via a second set of the plurality of conductors (e.g., 317), of second electrical power to a second transducer set of the plurality of transducers (e.g., 306) for a second time period $TP_2$ (approximately 8 minutes in FIG. 5B), an average of the second electrical power over the second time period $TP_2$ being greater than the first output power limit (e.g., indicated by the steeper slope of the initial portion of curve 504 as compared to the initial portion of temperature curve 502). In some embodiments, the second time period $TP_2$ is shorter than the first time period $TP_1$, and the delivery of the second electrical power to the second transducer set for the second time period $TP_2$ is (a) sufficient to cause tissue ablation via the second transducer set, and (b) sufficient to cause the portion of the shaft member (e.g., 313 or 316) to transition from the first temperature $T_1$ to a second temperature $T_2$ immediately upon conclusion of the second time period $TP_2$. In some embodiments, the second temperature $T_2$ is less than or equal to the first steady-state temperature $T_{SS1}$. Advantageously, the average of the second electrical power being greater than the first output power limit, along with the shorter time period (e.g., $TP_2$ as compared to $TP_1$) of application of such second electrical power, allows more power to be deliverable to the second set of the plurality of transducers (e.g., 306) to reduce ablation times without subjecting the patient to thermal injury via a carrier member (e.g. shaft member 313 or 316) employed to deliver the second output power.

It is noted according to various embodiments that the average of the second electrical power rather than an instantaneous value of the second electrical power is compared against the first output power level, because an instantaneous value of the power can fluctuate at a relatively high frequency (e.g., 10 Hz relative to the thermal time constant of the system). For example, instantaneous values of the power may fluctuate as an employed control loop updates setpoint voltages to achieve desired electrical currents, which correspond to the desired power level. Additionally, instantaneous levels of the power can also fluctuate with changing physiological conditions. For example, if an energy transmitting electrode (e.g., 319) is in intermittent contact with a tissue surface, various control loops can modulate the applied power accordingly in order to achieve a desired setpoint temperature.

Although the example of FIG. 5B is described in the context of the delivery of the second electrical power for a second time period $TP_2$, the delivery of the second electrical power may be delivered for any second time period that does not result in the temperature of the portion of the shaft member exceeding a temperature limit (e.g., 500) determined to cause thermally-induced tissue cellular damage, according to some embodiments. For instance, in the example of FIG. 5B, the second time period $TP_2$ may be considered a maximum time period of which the second electrical power may be delivered, according to some embodiments.

In FIG. 5B, at the end of the second time period $TP_2$, the temperature (on temperature curve 504) of the portion of the shaft member (e.g., 313 or 316) under the influence of the second electrical power is shown to reach the second temperature $T_2$ that is equal to the first steady-state temperature $Tss_1$ (e.g., approximately 48 degrees Celsius) according to some exemplary embodiments. In other embodiments, the temperature (e.g., represented by curve 504) of the portion of the shaft member (e.g., 313 or 316) under the influence of the second electrical power may reach a second temperature $T_{2\text{-}1}$ that is less than the first steady-state temperature $Tss_1$ (e.g., approximately 48 degrees Celsius) in a second time period $TP_{2\text{-}1}$, for example, as shown in FIG. 5B. That is, the shorter second time period (e.g., $TP_{2\text{-}1}$ approximately 7 minutes) may be considered sufficiently long to perform the desired ablations and the lower second temperature $T_{2\text{-}1}$ (i.e., lower than first steady-state temperature $Tss_1$) may provide an additional degree of safety in avoiding potentially harmful thermal energy delivery to the patient via at least tissue contact with the portion of the shaft member (e.g., 313 or 316). Additionally, the lower second temperature $T_{2\text{-}1}$ may allow for the reduction of potential delay for additional or subsequent ablations to be performed upon immediate conclusion of the second time period as described in more detail below in this disclosure. In some embodiments, the second temperature is not a steady-state temperature. For example in FIG. 5B, neither second temperature $T_2$ nor second temperature $T_{2\text{-}1}$ is a steady-state temperature $T_{SS2}$ of the temperature curve 504 of the shaft member (e.g., 313 or 316). It is noted in FIG. 5B that steady-state temperature $T_{SS2}$ is reached after a time period $TP_5$ has elapsed. In FIG. 5B, time period $TP_5$ is shown to be of the same duration as the first time period $TP_1$ on the basis that a time constant that characterizes the response to a step input of a first order system is the same regardless of whether the model reflects the first set of conductors (e.g., 317) or the second set of conductors (e.g. 317). In some embodiments, the first time period $TP_1$ may be different than time period $TP_5$ (for example, when time constant differences are present). It is noted that in some embodiments, the first set of the plurality of conductors (e.g., 317) that would deliver electrical power to define the first output power limit resulting in, e.g., temperature curve 502, may be the same as the second set of the plurality of conductors (e.g., 317) that deliver the higher second electrical power resulting in, e.g., temperature curve 504. In some embodiments, the first and the second sets of the plurality of conductors are different sets of the plurality of conductors (e.g., 317). For example, when the first set of the plurality of conductors is other than the second set of the plurality of conductors, but both the first and the second sets of the plurality of conductors have substantially equal overall electrical resistances (e.g., substantially identical resistances) provided by similar or substantially identical (e.g., within typical manufacturing tolerances) cross-sectional areas and similar or substantially identical (e.g., within typical manufacturing tolerances) lengths, then the identification of a suitable first output power limit that would be applicable to the delivery of the second electrical power via the first set of the plurality of conductors (e.g., 317) would also be applicable to the delivery of the second electrical power via the second set of the plurality of conductors (e.g., 317) as both sets of conductors would provide substantially the same amount of resistive heating under the influence of the delivered second electrical power. In some embodiments, the first transducer set is the second transducer set while, in other embodiments, the first transducer set is other than the second transducer set.

In some embodiments, the second electrical power, if delivered to the second transducer set for a time period longer than the second time period, is sufficient to cause the portion of the shaft member (e.g., 313 or 316) to transition from the first temperature to a third temperature, the third temperature determined to be sufficient to cause the thermally-induced tissue cellular damage (e.g., at least via contact between the portion of the shaft member and tissue). For example, in FIG. 5B, the second electrical power, if delivered to the second transducer set for a third time period $TP_3$ greater than the second time period $TP_2$, is sufficient to cause the portion of the shaft member (e.g., 313 or 316) to transition from the first temperature $T_1$ to a third temperature $T_3$, the third temperature $T_3$ being greater than the temperature limit 500. In various embodiments, the third temperature is greater than the first steady-state temperature. For example, in FIG. 5B, the third temperature $T_3$ is greater than the first steady-state temperature $T_{SS1}$. In some embodiments, the third temperature $T_3$ is sufficient to cause thermally-induced tissue cellular damage (e.g., at least via tissue contact by the portion of the shaft member). In some embodiments, the third temperature $T_3$ is sufficient to cause thermally-induced tissue cellular necrosis (e.g., at least via tissue contact by the portion of the shaft member). In some embodiments, the third time period is shorter than the first time period. For example, in FIG. 5B, the third time period $TP_3$ is shorter than the first time period $TP_1$. In some embodiments, the third temperature is a steady-state temperature. Although not shown in FIG. 5B, the third temperature $T_3$ may be the steady-state temperature $T_{SS2}$ associated with the temperature (e.g., represented by curve 504) of the portion of the shaft member (e.g., 313 or 316) under the influence of the second electrical power. In some embodiments, the third time period $TP_3$ may approach or exceed the first time period $TP_1$ (for example, when the third temperature $T_3$ approaches the steady-state temperature $T_{SS2}$). In some embodiments, the second electrical power may include a second output power limit that is greater than the first output power limit. For example, in FIG. 5B, the second electrical power is delivered with a second output power limit that is greater than the first output power limit according to some embodiments. That is, the second output power limit is sufficient to cause the second electrical power, if delivered for a particular time period, to cause the portion of the shaft member (e.g., 313 or 316) to exceed the temperature limit 500.

The second temperature (e.g., $T_2$ or $T_{2\text{-}1}$) may fall within various regions depending on, e.g., the applied temperature limit (e.g., 500 in the case of FIG. 5B). In some embodiments, the second temperature is a temperature within a range of 43 to 60 degrees Celsius, inclusive. It is noted that second temperatures above about 48 degrees Celsius may be associated with a higher temperature limit than limit 500 in FIG. 5B, according to some embodiments. In some embodiments, the second time period may extend for a particular amount of time. In some embodiments, the second temperature (e.g., $T_2$ or $T_{2\text{-}1}$) is a temperature less than or equal to 48 degrees Celsius, and the second time period (e.g., $TP_2$ or $TP_{24}$) is shorter than 10 minutes or shorter than or equal to 10 minutes. In some embodiments, the second temperature (e.g., $T_2$ or $T_{2\text{-}1}$) is a temperature less than or equal to 60 degrees Celsius, and the second time period (e.g., $TP_2$ or $TP_{2\text{-}1}$) is shorter than 1 minute or shorter than or equal to 1 minute. The selection of particular values or ranges of values for (a) the second temperature (e.g., $T_2$ or $T_{2-1}$), (b) the second time period (e.g., $TP_2$ or $TP_{2-1}$), or both (a) and (b) may be motivated by different reasons. For example, the second time period (e.g., $TP_2$ or $TP_{2-1}$) may be selected in accordance with various factors including, by way of non-limiting example, a particular thermal time constant of the system (e.g., 100, 300, or 400) or a required activation time period of various ones of the transducers (e.g., 306). By way of another example, the second temperature (e.g., $T_2$ or $T_{2-1}$) may be selected in accordance with various factors including by way of non-limiting example, the particular material or materials that the portion of the shaft member (e.g., 313 or 316) is made from, the duration of a particular activation time period required of particular ones of the transducers (e.g., 306) or the requirements for additional activations after the completion of the associated second time period (e.g., $TP_2$ or $TP_{2-1}$). In some embodiments, various regulatory requirements may have a bearing on the selection of (a) the second temperature (e.g., $T_2$ or $T_{2-1}$), (b) the second time period (e.g., $TP_2$ or $TP_{2-1}$), or both (a) and (b). Similarly, the third temperature (e.g., $T_3$), the third time period ($TP_3$), or both may vary for the same or similar reasons. Also similarly, the first steady-state temperature (e.g., $T_{SS1}$), the first time period (e.g., $TP_1$), or both may vary, e.g., based on the material or materials of the portion of the shaft member, or the type of tissue in contact with the portion of the shaft member, or various regulatory requirements. Also similarly, the second steady-state temperature (e.g., $T_{SS2}$) may vary, e.g., based on the material or materials of the portion of the shaft member and the amount of the second electrical power provided.

In some embodiments, the first temperature (e.g., $T_1$) corresponds to a state where the portion of the shaft member (e.g., 313 or 316) has been heated due to a prior delivery of electrical power e.g., to one or more transducers via one or more conductors (e.g., 317). In some embodiments, such prior electrical power is sometimes referred to herein as a third electrical power. Third electrical power may also be referred to herein at times as electrical power delivered after delivery of the second electrical power, as discussed in more detail further below. In some embodiments, the controller (e.g., 324) is configured to cause third electrical power to be delivered to at least a third transducer set of the plurality of transducers (e.g., 306), the third electrical power delivered to at least the third transducer set prior to the delivery of the second electrical power to the second transducer set, and the first temperature $T_1$ is a temperature of the portion of the shaft member (e.g., 313 or 316) after the third electrical power is delivered to at least the third transducer set. For example, in some embodiments, the temperature of the portion of the shaft member (e.g., 313 or 316) may be heated to a temperature at least equal to the first temperature (e.g., $T_1$) as the result of an activation of a particular transducer set prior to the activation of the second transducer set with the second electrical power, which causes the temperature curve 504. That is, in some embodiments, the delivery of the third electrical power may be considered to be a first or preceding delivery of electrical power during a particular diagnostic or treatment procedure, and the delivery of the second electrical power (e.g., resulting in temperature curve 504) may be considered to be a secondary or subsequent delivery of electrical power that is preceded by at least one other delivery of electrical power during the particular diagnostic or treatment procedure. In various embodiments, the third electrical power delivered to at least the third transducer set is sufficient to cause tissue ablation via the third transducer set. In various embodiments, the second transducer set is other than the third transducer set, while in other embodiments, the second transducer set is the third transducer set.

In some embodiments, the delivery of the second electrical power to the second transducer set is not the only delivery of electrical power to a transducer set of the plurality of transducers (e.g., 306) during a particular diagnostic or treatment procedure or a last or final delivery of electrical power to a transducer set of the plurality of transducers (e.g., 306) during a particular diagnostic or treatment procedure. In some embodiments, the delivery of the second electrical power to the second transducer set is followed by a subsequent delivery of electrical power to another transducer set of the plurality of transducers (e.g., 306) (for example, after the completion of the delivery of the second electrical power), both the delivery of the second electrical power and the subsequent delivery of electrical power occurring during a same diagnostic or treatment procedure.

In some embodiments, the controller (e.g., 324) is configured to cause third electrical power to be delivered to at least a third transducer set of the plurality of transducers (e.g., 306), the third electrical power delivered to at least the third transducer set after the delivery of the second electrical power to the second transducer set has completed. For example, according to some embodiments, the delivery of the second electrical power is followed by the delivery of third electrical power after the completion of the delivery of the second electrical power. Some of such embodiments are described in further detail below with respect to FIGS. 8B and 8C, where it is discussed that a "first" electrical power (which may correspond to the presently discussed "third" electrical power) may be delivered during a time period $TP_0$ in FIGS. 8B and 8C after completion of delivery of a second electrical power during a time period $TP_2$ in FIGS. 8B and 8C. In some embodiments (for example, as described in further detail below with respect to at least FIG. 8B), the third electrical power includes a third output power limit that is determined based at least on the temperature of the portion of the shaft member at a point in time (e.g., time $t_1$ in FIG. 8B) after the completion of the delivery of the second electrical power (e.g., during time period $TP_2$ in FIG. 8B) and before the start of the delivery of the third electrical power (e.g., time $t_1$ is before delivery of the third electrical power (also referred to as the first electrical power in the discussions of FIGS. 8B and 8C below) during time period $TP_0$ in FIGS. 8B and 8C).

In some embodiments, the third output power limit is less than the second output power limit. For example, as described in further detail below, the second temperature (e.g., $T_2$, $T_{2-1}$) of the portion of the shaft member (e.g., 313 or 316) after the delivery of the second electrical power has been completed may be sufficiently high that, if followed by the delivery of the third electrical power with an output power limit at least as large as the second output power limit, would subsequently cause the temperature of the portion of the shaft member to undesirably increase beyond the temperature limit 500. Therefore, in some embodiments, the delivery of the third electrical power is associated with a lower output power limit to keep the temperature of the portion of the shaft member below the temperature limit 500 throughout the delivery of the third electrical power.

In some embodiments, the system (e.g., 100, 300, or 400) includes at least a first temperature sensor configured to sense any particular temperature described in this disclosure such as, but not limited to, the first temperature $T_1$, the second temperature $T_2$, $T_{2-1}$, or both the first temperature and the second temperature. In various embodiments, the at least the first temperature sensor is configured to directly sense temperature information. In some embodiments, the at least the first temperature sensor is configured to sense particular information that is responsive to a particular temperature that is to be sensed. For example, with reference to FIG. 4, temperature sensors 408 include various elements 409 (which may be conductors) whose resistance varies in response to temperature changes. Various electrical current and voltage information may be sensed (e.g., by controller 324 or other data processing device system 110) to determine a resistance of at least part of an element 409 to in turn determine related temperature information according to some embodiments. In some embodiments, the resistance of a particular conductor that is located in the shaft member (e.g., 313 or 316) is determined to in turn determine a temperature of at least a portion of the shaft member. In some embodiments, the particular conductor is configured to not delivery energy sufficient for tissue ablation to a particular transducer (e.g., 306). In some embodiments, the particular conductor is electrically coupled or connected to a particular transducer that is not employed to ablate tissue. In some embodiments, the particular conductor is electrically coupled or connected to a particular portion of a transducer (e.g., 409a, 409b), the particular portion of the transducer being configured to not ablate tissue. In some embodiments, the temperature sensor is located on or in the shaft member. For example, the first temperature sensor may be included on or in the shaft member 313 of catheter sheath 312. For example, in FIG. 3A, the shaft member 313 of catheter sheath 312 includes a proximal end portion 313a that includes a proximal end 313a-1 and distal end portion 313b that includes a distal end 313b-1. In various embodiments, the distal end portion 313b is arranged to be advanced ahead of the proximal end portion 313a when the shaft member 313 is inserted into the patient. In some embodiments, the first temperature sensor is provided by a sensor 342a located on or in the shaft member 313 at a location closer to the distal end 313b-1 of the shaft member 313 than the proximal end 313a-1 of the shaft member 313. In some embodiments, the first temperature sensor is provided by a sensor 342b located on or in the shaft member 313 at a location closer to the proximal end 313a-1 of the shaft member 313 than the distal end 313b-1 of the shaft member 313.

According to various embodiments, the location of the first temperature sensor may be motivated by various factors including a desire to position the first temperature sensor on or in a particular portion of the shaft member (e.g., a particular portion of the shaft member that is positionable in contact with or adjacent to a tissue surface during a diagnostic or treatment procedure) to determine the temperature of the particular portion of the shaft member. In some embodiments, the first temperature sensor may be located on or in the shaft member 316 of the catheter 314 itself. This location may be motivated for various reasons. For example, in several embodiments, the shaft member 316 acts as a carrier member for various conductors including the various conductors (e.g., 317) electrically connected to the plurality of transducers (e.g., 306) located on the structure (e.g., 308). Accordingly, one or more conductors connected to the first temperature sensor may be carried by the shaft member 316 with comparatively little effort or additional cost (e.g., as compared to the catheter sheath 312 upon which few or no transducers may be located). In some embodiments, the first temperature sensor is provided at least in part by a first conductor, at least a portion thereof included in the shaft member (e.g., 313 or 316). In some embodiments, the controller (e.g., 324) is configured to measure any particular temperature described in this disclosure including, but not limited to, the first temperature $T_1$, the second temperature $T_2$, $T_{2-1}$ or both the first temperature and the second temperature based at least on a (measured) resistance of at least part of the first conductor. For example, as described above with respect to FIG. 4, various conductors 410 are employable to determine a resistance of a resistive element 409, and subsequently determine a temperature change that is related to changes in the measure resistance. In a similar manner, a resistance of a particular portion of the first conductor extending through the portion of the shaft member may be determined by the controller (e.g., 324), the resistance value varying with changes in the temperature (e.g., as discussed above with respect to FIG. 4). In some embodiments, in which the first temperature sensor is located in or on the shaft member 316 of catheter 314, controller 324 may, by way of non-limiting example, adjust a measured temperature value by a) employing a temperature offset or b) by employing scaling, or both a) and b) to account for the presence of an intervening structure (e.g., catheter sheath 312) between the portion of the shaft member 316 and adjacent tissue.

In some embodiments, the controller (e.g., 324) is configured to determine (such as, but not limited to, predict, measure, or estimate) the second temperature $T_2$, $T_{2-1}$ based at least on a predictive model and (a) information related to the first temperature (e.g., $T_1$), (b) information related to electrical power (e.g., the second electrical power), (c) information related to the second time period or a combination of (a) and (b), or (a) and (c), or (b) and (c), or (a), (b) and (c). The use of a predictive model, may in some embodiments be more economically desirable than the use of a particular temperature sensor configured and arranged to sense temperature information. Various predictive models are described below in this disclosure.

In some embodiments, the controller (e.g. 324) is configured to cause delivery, via a first set of conductors of the plurality of conductors (e.g., 317), of first electrical power, e.g., via a first electrical current signal set including one or more electrical current signals delivered via the first set of conductors 317, to a first transducer set of the plurality of transducers (e.g. 306), the first electrical power/first electrical current signal set sufficient to cause, if delivered for a first time period, a portion of the shaft member (e.g., 313 or 316) to transition from a first temperature to a steady-state temperature immediately upon conclusion of the first time period, the steady-state temperature sufficient to cause thermally-induced tissue cellular damage and, in some cases, thermally-induced tissue cellular necrosis. For example, in FIG. 5B, the temperature curve 504 of the portion of shaft member (e.g., 313 or 316) may be associated with the delivery, via a first set of the plurality of conductors (e.g., 317), of first electrical power, e.g., via a first electrical current signal set including one or more electrical current signals delivered via the first set of conductors 317, to a transducer set of the plurality of transducers (e.g. 306), the first electrical power sufficient to cause, if delivered for a first time period $TP_5$, a portion of the shaft member (e.g., 313 or 316) to transition (e.g., along temperature curve 504) from a first temperature $T_1$ to a steady-state temperature $T_{SS2}$ immediately upon conclusion of the first time period $TP_5$, the steady-state temperature $T_{SS2}$ sufficient to cause at least thermally-induced tissue cellular damage (e.g., at least via tissue contact with the portion of the shaft member). It is noted that various particular portions of the temperature curve 504 for the portion of the shaft member (e.g., 313 or 316) (e.g., a portion of the curve 504 that are above the temperature limit 500 that does not represent the steady-state temperature $T_{SS2}$) are also sufficient to cause, or determined to be sufficient to cause thermally-induced tissue cellular damage via at least contact between the portion of the shaft member and tissue. In some embodiments, the steady-state temperature $T_{SS2}$ is sufficient to cause thermally-induced tissue cellular necrosis. In some embodiments, the controller (e.g., 324) is configured to cause delivery of the first electrical power/first electrical current signal set to the first transducer set for a second time period (e.g., $TP_2$ or $TP_{2-1}$), the second time period shorter than the first time period $TP_5$, and the delivery of the first electrical power/first electrical current signal set to the transducer set for the second time period (e.g., $TP_2$, $TP_{2-1}$) is (a) sufficient to cause tissue ablation via the first transducer set, and (b) sufficient to cause the portion of the shaft member (e.g., 313 or 316) to transition from the first temperature $T_1$ to a second temperature (e.g., $T_2$ or $T_{2-1}$) immediately upon conclusion of the second time period (e.g., $TP_2$, $TP_{2-1}$), the second temperature (e.g., $T_2$, $T_{2-1}$) less than the steady-state temperature $T_{SS2}$. In various embodiments, the second temperature (e.g., $T_2$, $T_{2-1}$) is insufficient or is determined to be insufficient to cause thermally-induced tissue cellular damage (e.g., at least via tissue contact with the portion of the shaft member). In various embodiments, the second temperature (e.g., $T_2$, $T_{2-1}$) is insufficient or is determined to be insufficient to cause thermally-induced tissue cellular necrosis.

It is noted that electrical power is related to, or proportional to, the mathematical square of the electrical current that is delivered during the delivery of the electrical power. Accordingly, the delivery of the first electrical current signal set via the first set of the plurality of conductors (e.g., 317) is accompanied by, or associated with, a delivery of electrical power (e.g., the first electrical power described above) via the first set of conductors. According to various embodiments, resistive heating created in the first set of conductors from the delivery of the first set of electrical current signals or the delivery of the first electrical power, can lead to temperature increases in a portion of the shaft member (e.g., 313 or 316), the first set of conductors located at least in part in the shaft member. The first electrical current signal set may include one or more signals having a particular set of characteristics. For example, in some embodiments in which radio frequency (RF) ablation techniques are employed, the first electrical current signal set may include one or more RF signals. RF signals typically employ electromagnetic wave frequencies that lie in a range from about 3 kHz to 300 GHz. A 480 kHz RF signal waveform has been employed by the current inventors in some tissue ablation applications. In some embodiments, the first electrical current signal set may include other forms or types of AC signals. Without limitations, an AC signal that forms at least part of the first electrical signal set may include any suitable amplitude, frequency, phase, or a combination thereof that may be required during an activation of an associated transducer (e.g., 306). In some embodiments, the first electrical current signal set may include an electrical current signal having a duty cycle waveform marked by a sequence of on-and-off energy delivery intervals (i.e., the duty cycle describing a percentage of the signal's "on" interval over a period of time having a duration equal to a combination of an "on" interval and an "off" interval).

In some embodiments, the second temperature (e.g., $T_2$, $T_{2-1}$) is not a steady-state temperature. For instance, the examples of second temperature $T_2$, $T_{2-1}$ are in a rising portion of the temperature curve 504 of the portion of the shaft member (e.g., 313 or 316) under the influence of the delivery of the first electrical power/first electrical current signal set.

As discussed above, in some embodiments, the system (e.g., 100, 300, or 400) includes at least a first temperature sensor configured to sense the first temperature, the second temperature, or both the first temperature and the second temperature. The first temperature sensor may be provided by various suitable sensors including those described above in this disclosure. In some embodiments, the controller (e.g., 324) is configured to estimate the second temperature $T_2$, $T_{2-1}$ based at least on a predictive model and (a) information related to the first temperature $T_1$, (b) information related to the first electrical power or first electrical current signal set, (c) information related to the second time period, or a combination of (a) and (b), or (a) and (c), or (b) and (c), or (a), (b) and (c). As discussed above, the use of a predictive model, may, in some embodiments, be more economically desirable than the use of a particular temperature sensor configured and arranged to sense temperature information. Various predictive models are described below in this disclosure.

In some embodiments, delivery of the first electrical power/first electrical current signal set to the first transducer set, if delivered for a third time period longer than the second time period, is sufficient to cause the portion of the shaft member (e.g., 313 or 316) to transition from the first temperature to a third temperature, the third temperature sufficient to cause thermally-induced tissue cellular damage. For example, in some embodiments associated with FIG. 5B, the delivery of the first electrical power to the first transducer set, if delivered for a third time period (e.g., $TP_3$) greater than the second time period (e.g., $TP_2$, $TP_{2-1}$), is sufficient to cause the portion of the shaft member (e.g., 313 or 316) to transition from the first temperature $T_1$ to a third temperature $T_3$, the third temperature determined sufficient to cause thermally-induced tissue cellular damage since the third temperature $T_3$ is above the temperature limit 500. According to some embodiments associated with FIG. 5B, the third time period (e.g., $TP_3$) is shorter than the first time period $TP_1$. In some embodiments, third temperature (e.g., $T_3$) is sufficient to cause thermally-induced tissue cellular necrosis.

As discussed above, the first temperature (e.g., $T_1$) may represent a state where the portion of the shaft member (e.g., 313 or 316) is unheated or substantially unheated from a prior delivery of electrical power e.g., via a set of one or more electrical current signals to one or more transducers via one or more conductors (e.g., 317). Or, as discussed above, the first temperature (e.g., $T_1$) may represent a state where the portion of the shaft member (e.g., 313 or 316) has been heated due to a prior delivery of electrical power, e.g., via a set of one or more electrical current signals to one or more transducers via one or more conductors (e.g., 317). In the heated case, for example, the controller (e.g., 324) is configured, in some embodiments, to cause particular electrical power via a particular electrical current signal set to be delivered to at least a second transducer set of the plurality of transducers (e.g., 306), the particular electrical power delivered to at least the second transducer set delivered prior to the delivery of the first electrical power/first electrical current signal set to the first transducer set (causing temperature curve 504 in FIG. 5B in some embodiments), and the first temperature (e.g., $T_1$) is a temperature of the portion of the shaft member (e.g., 313 or 316) after the particular electrical power/particular electrical current signal set is delivered to at least the second transducer set. For example, in some embodiments, the temperature of the portion of the shaft member (e.g., 313 or 316) may be heated to a temperature at least equal to the first temperature (e.g., $T_1$) as the result of an activation of a particular transducer set prior to the activation of the first transducer set. That is, according to some embodiments, the delivery of the particular electrical power/particular electrical current signal set may be considered to be an initial or preceding delivery of electrical power during a particular diagnostic or treatment procedure, and the delivery of the first electrical power/first electrical current signal set may be considered to be a secondary or subsequent delivery of power that is preceded by at least one other delivery of electrical power during the particular diagnostic or treatment procedure. In various embodiments, the particular electrical power/particular electrical current signal set delivered to at least the second transducer set is sufficient to cause tissue ablation via the second transducer set. In various embodiments, the first transducer set is other than the second transducer set, while in other embodiments, the first transducer set is the second transducer set.

On the other hand, as discussed above, the first temperature (e.g., $T_1$) may represent a state where the portion of the shaft member is unheated relative to an ambient temperature or substantially unheated relative to an ambient temperature (e.g., a prior delivery of electrical power, e.g., via a set of one or more electrical current signals to any or one or more transducers via any or one or more conductors (e.g., 317) within the shaft member (e.g., 313 or 316) sufficient to measurably heat the shaft member has not occurred). In some embodiments, the first temperature $T_1$ is an ambient temperature. In some embodiments, the first temperature $T_1$ is a temperature of the portion of the shaft member (e.g., 313 or 316) prior to the controller (e.g., 324) causing electrical power to be delivered to any transducer of the plurality of transducers (e.g. 306). In some embodiments, the first temperature $T_1$ is a temperature of the portion of the shaft member (e.g., 313 or 316) prior to the activation of any one of the plurality of transducers (e.g., 306). In some embodiments, the first temperature $T_1$ is a temperature of the portion of the shaft member (e.g., 313 or 316) prior to the controller (e.g., 324) causing electrical power to be delivered to any particular transducer of the plurality of transducers (e.g. 306) to cause the particular transducer to emit energy sufficient for tissue ablation.

According to various embodiments, various particular relationships may be employed to derive power (e.g., a power limit or a power level) that is dissipated in a particular conductor or portion thereof. For example, one particular generalized relationship between power, voltage, and electrical current may be represented as:

$$\text{Power }(P) = \text{Voltage }(V) * \text{Current }(I) \qquad \text{(rel. \#1)}$$

For example, if electrical current is flowing through a portion of a conductor (e.g., 317), and, if the voltage difference from one end of the portion of the conductor to the other end of the portion of the conductor is measured at a same particular moment in time, then the product of voltage and current will be the rate at which heat is generated in the portion of the conductor at the same particular moment in time.

Other particular relationships may also be employed to determine the generated heat in a particular conductor (e.g., 317). For example, the generalized relationship rel. #1 may be alternatively expressed (e.g., based on Ohm's Law where V=I*R) as:

$$P = I^2 * R \qquad \text{(rel. \#2)}$$

where P and I are defined as above and R is the resistance of the portion of the conductor through which the power is delivered.

It is noted that electrical current can only flow in the portion of the conductor (e.g., 317) if the portion of the conductor is included in some particular circuit forcing it or inducing it to do so. If conditions at some other moment in time are different, then various ones of V, I and P will be different, but they will still be interrelated via the same relationship.

When voltage and electrical current values vary with time (for example, in the case of voltage/current signals having sinusoidal waveforms (e.g., AC signals), quasi-sinusoidal waveforms, or other forms of time varying waveforms), then the average power that generates heat in the portions of the conductor (and a surrounding part of the shaft member (e.g., 313 or 316)) may be determined by the following particular relationship:

$$P = (1/T) \int_0^T V(t) I(t) dt \qquad \text{(rel. \#3)}$$

where P is the average power measured over a time interval T, V(t) is the time varying voltage (i.e., varying across the time interval T), and I(t) is the time varying electrical current (i.e., varying across the time interval T).

Root mean square (RMS) is defined as the square root of mean square (i.e., the mathematical or arithmetic mean of the squares of a set of values). RMS may, in some cases also be defined for a continuously varying function in terms of an integral of the squares of the instantaneous values during a cycle. For a time varying electrical current signal, the RMS value of the electrical current signal may be defined as a value that is equal to a value of direct current that produces the same power dissipation in a resistive load. As power dissipation through a portion of a conductor is primarily related to resistive losses, particular relationships employing RMS values are preferably employed with time varying signals. It is noted that some capacitive or inductive losses may be associated with power dissipation through a conductor (e.g., 317) and thus, the power dissipation may not be solely attributable to resistive losses. Nonetheless, the capacitive or inductive losses are generally considered insignificant in various embodiments. Different electrical current signal waveforms will have different associated RMS values. The RMS values for a few different signals are provided by way of non-limiting examples:

a) a pure sinusoidal signal that is symmetrical about zero with a peak amplitude value of $A_1$ has an associated RMS value equal to $A_{RMS} = A_1/\sqrt{2}$;

b) a half-wave rectified sinusoid signal that only contains the positive (or negative) values of a sinusoid signal with a peak value (i.e., from zero) of $A_1$ has an associated RMS value equal to $A_{RMS} = A_1\sqrt{2}$; and c) a square-wave with only positive (or negative) values $A_1$ (i.e., from zero) with a duty cycle $\delta$ has an associated RMS value equal to $A_{RMS} = A_1 * \sqrt{\delta}$.

The respective RMS values of other electrical current signals may be derived from the following relationship:

$$I_{RMS} = \sqrt{\left(\frac{1}{T}\right) \int_0^T I(t)^2 \, dt} \qquad \text{(rel. \#4)}$$

where $I_{RMS}$ is the RMS value of the electrical current signal over a period of time from 0 to T, and $I(t)^2$ is the mathematical square of the time varying electrical current.

With reference to relationships (rel. #1) and (rel. #2), above, it is noted that there are particular relationships between the dissipated power within a portion of a conductor (e.g., 317) and the electrical current that flows in the portion of the conductor. For example, according to some embodiments in which the resistance of the portion of the conductor remains essentially constant, power dissipated in the portion of the conductor is proportional to a mathematical square of electrical current. In some embodiments, an output power limit may be alternatively expressed by an electrical current-based limit. In some embodiments, an electrical current-based limit is derivable based on a particular relationship that includes a mathematical square of a value of the electrical current delivered through a portion of the conductor (e.g., 317). In this regard, both the terms output power limit and electrical current-based limit may be used interchangeably depending on the context (e.g., an output power may be proportional to a value of a corresponding electrical current-based limit). In this light, although the graphed temperatures in FIGS. 5A, 5B, and FIGS. 8A, 8B, and 8C (described in further detail below) are referenced to various output power limits, it is understood that they can also be referenced to corresponding electrical current-based limits.

In some embodiments, a controller (e.g., 324) is operatively coupled to one or more transducers (e.g., 306) via one or more conductors (e.g., 317), the one or more conductors coupled to the one or more transducers. According to various embodiments, the controller (e.g., 324) is configured to cause delivery of electrical current or power (e.g., via energy source device system 340) to the one or more transducers via the one or more conductors (e.g., 317), at least a portion of each conductor of the one or more conductors located in the shaft member (e.g., 313 or 316). In some embodiments, the one or more transducers (e.g. 306) include multiple transducers. In some embodiments, the one or more conductors include a plurality of conductors.

According to some embodiments, an electrical current-based limit is defined as a first value derivable, according to a particular relationship, from each electrical current signal of a first electrical current signal set. The first electrical current signal set, if delivered via a first set of the one or more conductors (e.g., 317) to a first transducer set of the one or more transducers for a first time period, is sufficient to cause a portion of the shaft member (e.g., 313 or 316) to transition from a first temperature to a first steady-state temperature immediately upon conclusion of the first time period. The first steady-state temperature is or is determined to be insufficient to cause thermally-induced tissue cellular damage in some embodiments. For example, with reference to FIG. 5B, a first electrical current signal set may provide a level of power that, if delivered via a first set of the one or more conductors (e.g., 317) to a first transducer set of the one or more transducers (e.g., 306) for a first time period $TP_1$ causes a temperature (e.g., along temperature curve 502) of a portion of the shaft member (e.g., 313 or 316) to transition from a first temperature $T_1$ (e.g., approximately 30 degrees Celsius) to a first steady-state temperature $T_{SS1}$ (e.g., approximately 48 degrees Celsius) immediately upon conclusion of the first time period $TP_1$. The first steady-state temperature $T_{SS1}$ is insufficient, or is determined to be insufficient (for example, according the determination of IEC 60601-1:2005/A1:2012 or another requirement) to cause thermally-induced tissue cellular damage or thermally-induced tissue cellular necrosis (e.g., via at least contact with the portion of the shaft member). Accordingly, in the present discussion, the first electrical current signal set is associated with a delivery of electrical power that is insufficient to cause thermally-induced tissue cellular damage. As described above, in some embodiments associated with FIG. 5B, the first temperature $T_1$ is an ambient temperature (e.g., a generally consistent surrounding temperature) and the first time period $TP_1$ is approximately 37 minutes, but it is understood that other first temperatures and first time periods may be employed in other embodiments.

In some embodiments, a controller (e.g., 324) is configured to cause delivery, via a second set of conductors of the one or more conductors (e.g., 317), of a second electrical current signal set to a second transducer set of the one or more transducers (e.g., 306) for a second time period (e.g., $TP_2$ which is approximately 8 minutes in FIG. 5B or $TP_{2-1}$ which is approximately 7 minutes in FIG. 5B), a second value derivable, according to the particular relationship, from each electrical current signal of the second electrical current signal set being greater than the electrical current-based limit, the second time period (e.g., $TP_2$, $TP_{2-1}$) being shorter than the first time period $TP_1$, and the delivery of the second electrical current signal set to the second transducer set for the second time period (e.g., $TP_2$, $TP_{2-1}$) being (a) sufficient to cause tissue ablation via the second transducer set, and being (b) sufficient to cause the portion of the shaft member (e.g., 313 or 316) to transition from the first temperature $T_1$ to a second temperature (e.g., $T_2$, $T_{2-1}$) immediately upon conclusion of the second time period (e.g., $TP_2$, $TP_{2-1}$), the second temperature (e.g., $T_2$, $T_{2-1}$) being less than or equal to the first steady-state temperature $T_{SS1}$. The first temperature (e.g., $T_1$) and the second temperature (e.g., $T_2$, $T_{2-1}$) have the characteristics described above, according to various embodiments.

As discussed above, in some embodiments, the system (e.g., 100, 300, or 400) includes at least a first temperature sensor configured to sense the first temperature, the second temperature, or both the first temperature and the second temperature. The first temperature sensor may be provided by various suitable sensors including those described above in this disclosure.

In some embodiments, the controller (e.g., 324) is configured to estimate the second temperature (e.g., $T_2$, $T_{2-1}$) based at least on a predictive model and (a) information related to the first temperature $T_1$, (b) information related to the second electrical current signal set, (c) information related to the second time period, or a combination of (a) and (b), or (a) and (c), or (b) and (c), or (a), (b) and (c). Various predictive models are described below in this disclosure According to various embodiments, the second value derivable, according to the particular relationship, from each electrical current signal in the delivered second electrical current signal set is greater than the corresponding first value of the first electrical current-based limit (the first value also derivable from the particular relationship) and therefore advantageously allows more power or an aggregate greater amount of electrical current to be deliverable to the second transducer set of the one or more transducers (e.g., 306) for shorter treatment (e.g., ablation) or diagnostic times without subjecting the patient to thermal injury via a carrier member (e.g. shaft member 313 or 316) employed to deliver the second electrical current signal set. In some embodiments, the second transducer set includes at least two transducers of a plurality of transducers (e.g., 306).

The second electrical current set may include particular characteristics. For example, in some embodiments, the second electrical current signal set, if delivered to the second transducer set for a third time period longer than the second time period, is sufficient to cause the portion of the shaft member (e.g., 313 or 316) to transition from the first temperature to a third temperature, the third temperature sufficient or deemed sufficient to cause thermally-induced tissue cellular damage. For example, in some embodiments associated with FIG. 5B, the second electrical current signal set, if delivered to the second transducer set for a third time period (e.g., $TP_3$) greater than the second time period (e.g., $TP_2$, $TP_{2-1}$), is sufficient to cause the portion of the shaft member (e.g., 313 or 316) to transition from the first temperature $T_1$ to a third temperature $T_3$, the third temperature sufficient to cause thermally-induced tissue cellular damage since the third temperature $T_3$ is above the temperature limit 500. According to some embodiments associated with FIG. 5B, the third time period (e.g., $TP_3$) is shorter that the first time period $TP_1$. In some embodiments, the third temperature is sufficient to cause thermally-induced tissue cellular necrosis. In some embodiments, the third temperature is a steady-state temperature (e.g., $T_{SS2}$). In some embodiments, the third temperature is greater the first steady-state temperature (e.g., $T_{SS1}$).

In some embodiments, the particular relationship discussed above with respect to derivation of the first value associated with the first electrical current signal set and derivation of the second value associated with the second electrical current signal set, is related to a particular value associated with each electrical current signal in an electrical current signal set. For example, according to some embodiments, the particular value associated with each particular electrical current signal in the electrical current signal set may be related to an amplitude of the particular electrical current signal in the electrical current signal set. In some embodiments, the particular value associated with each particular electrical current signal in the electrical current signal set may be related to one or more magnitudes of the particular electrical current signal in the electrical current signal set. In some embodiments, the particular relationship includes a summation of respective particular values, each respective particular value associated with a respective electrical current signal in an electrical current signal set. That is, the one or more conductors (e.g., 317) may, in some embodiments, include multiple conductors located within the shaft member (e.g., 313 or 316), and the particular relationship may include a summation of the particular values associated with the electrical current signals flowing in the multiple conductors. In some embodiments, the particular relationship includes as summation of a square (i.e., a mathematical square) of a root mean square (RMS) value of electrical current signal in an electrical current signal set. When dealing with time varying signals, such as AC electrical current signals, attempts to find an average value of each signal can lead to an answer of 'zero'. The use of RMS values allows for an effective or more meaningful value to be determined (e.g., a value that is equal to a value of direct current that would produce the same power dissipation in a resistive load). The particular relationship may be defined according to some embodiments as follows:

$$\text{Value} = \sum_{n=1}^{N} IRMS_n^2 \quad \text{(rel. \#5)}$$

where Value is a particular electrical current-based value and $IRMS_n^2$ is the mathematical square of an RMS value of electrical current signal "n" in an electrical current signal set of "N" electrical current signals, "N" being an integer greater than or equal to one. It is noted in various embodiments that "N" may be equal to the number of conductors (e.g., 317) within the shaft member (e.g., 313 or 316) that deliver the electrical current signal set. For example, in some embodiments, the controller (e.g., 324) is configured to cause delivery of each electrical current signal of at least the second electrical current signal set to each transducer in the second transducer set via a respective conductor of the one or more conductors. In some embodiments, "N" is a number greater than one.

In some embodiments, each of (a) the first value (e.g., the electrical current-based limit) derivable from each electrical current signal of the first electrical current signal set deliverable via the first set of one or more conductors to a first transducer set, and (b) the second value derivable from each electrical current signal in the second electrical current signal set deliverable via the second set of one or more conductors to a second transducer set, may be derivable according to a particular relationship that is provided by relationship (rel. #5). In some embodiments, the first transducer set is the second transducer set, while in other embodiments, they are different. In some embodiments, the first set of one or more conductors carrying the first electrical current signal set is the second set of one or more conductors carrying the second electrical current signal set. In such cases in which the first set of the one or more conductors (e.g., 317) is the second set of one or more conductors (e.g., 317), (i.e., both the first and the second sets of the one or more conductors are provided by a same set of the one or more conductors) and each electrical current signal in each of the first and the second electrical current signal sets is deliverable via a respective one of the one or more conductors, then the second value is greater than the first value that provides the electrical current-based limit primarily on the basis that the respective RMS values of at least some of the electrical current signals that are employed to derive the second value is or are different (e.g., greater) than the respective RMS values of at least some of the electrical current signals that are employed to derive the first value.

In other embodiments, different first and second sets of the one or more conductors (e.g., 317) may be employed to derive respective ones of the first value and the second value. In some embodiments, the first set of one or more conductors may include a different number of conductors than the second set of one or more conductors. For example, assuming that the RMS value of each signal of the first electrical current signal set and the second electrical current signal set is a same RMS value and each electrical current signal in each of the first and the second electrical current signal sets is deliverable via a respective one of the one or more conductors, then the second value is greater than the first value that provides the electrical current-based limit primarily on the basis that the number of conductors that are associated with the derivation of the first value number fewer than the number of conductors that are associated with the derivation of the second value.

As per another example, assuming that at least some of the RMS values of the second electrical current signal set are different than at least some of the RMS values of the first electrical current signal set, then the second value is greater than the first value that provides the electrical current-based limit in a case where the sum of the mathematical squares of the RMS values of the second electrical current signal set is greater than the sum of the mathematical squares of the RMS values of the first electrical current signal set. Accordingly, in some embodiments in which a particular second electrical current signal set associated with the second value has a greater number of electrical current signals than a particular first electrical current signal set associated with the first value that provides the electrical current-based limit, the second value will be greater than the first value in a case in which the sum of the mathematical squares of the RMS values of the electrical currents of the particular second electrical current signal set is greater than the sum of the mathematical squares of the RMS values of the electrical currents of the particular first electrical current signal set based at least on the particular values of the RMS values associated with the particular first and the particular second electrical current signal sets. Conversely, in some embodiments in which a particular second electrical current signal set associated with the second value has the same or a fewer number of electrical current signals than a particular first electrical current signal set associated with the first value that provides the electrical current-based limit, the second value to be greater than the first value in a case in which the sum of the mathematical squares of the RMS values of the electrical currents of the particular second electrical current signal set is greater than the sum of the mathematical squares of the RMS values of the electrical currents of the particular first electrical current signal set based at least on the particular values of the RMS values associated with the particular first and the particular second electrical current signal sets.

It is noted that, in a case where each electrical current signal in each of the particular first and the particular second electrical current signal sets is deliverable via a respective conductors, then the number of the conductors in the first set of the one or more conductors via which the particular first electrical current signal set is delivered will equal the number of the electrical current signals in the particular first electrical current signal set, and the number of the conductors in the second set of the one or more conductors via which the particular second electrical current signal set is delivered will equal the number of the electrical current signals in the particular second electrical current signal set according to some embodiments.

Accordingly, numerous different combinations of electrical current signals having particular associated RMS values may be employed to derive each of the electrical current-based limit and the current-based value that is associated with the delivery of the second electrical current signal set to advantageously allow the second electrical current signal set to provide greater electrical power (e.g., to cause temperature curve 504 in FIG. 5B) than the first electrical current signal set (e.g., causing temperature curve 502), while being deliverable for a second time period $TP_2$ or $TP_{2-1}$ that is shorter than the first time period $TP_1$ that is associated with the electrical current-based limit (e.g., associated with temperature limit 500), without causing the portion of the shaft member (e.g., 313 or 316) to transition to a temperature that would cause, or be deemed to cause, thermally-induced tissue cellular damage (e.g., a temperature above the temperature limit 500).

It is noted that at least some of the electrical current signals in the second electrical current signal set may have different associated RMS values for different reasons. For example, in some embodiments, each electrical current signal of the second electrical current signal set may be deliverable to a respective one of a group of a plurality of transducers (e.g., 306). Different ones of the group of the plurality of transducers (e.g., 306) may require different levels of electrical current during their activation. For example, in applications in which each transducer of the group of the plurality of transducers (e.g., 306) includes a respective electrode, a group of the electrodes having different sizes may include differences between the RMS values of the associated electrical current signals delivered to the group of electrodes (e.g., smaller electrodes typically require more current than larger electrodes to ablate tissue to a particular depth). A particular condition caused by loss of tissue contact or intermittent contact between a particular electrode and tissue can also cause the electrical current signal supplied to the electrode to vary as the control system (e.g., provided at least by the controller 324 in some embodiments) responds to the particular condition. These and other conditions can lead to differences among the electrical current signals of the second electrical current signal set or other electrical current signals, such as at least some of the electrical current signals in the first electrical current signal set, discussed herein.

As stated above in relationship (rel. #2), the power P dissipated in a portion of a conductor (e.g., 317) through which an electrical current is delivered is provided by $P=I^2*R$, where R is the electrical resistance of the portion of the conductor. Relationship (rel. #5) is based on the premise that the electrical resistances of the conductor portions through which the electrical currents of the electrical current signal set flow are substantially the same. Thus, under this premise, the value provided by relationship (rel. #5) is proportional to, but not equal to, the total power dissipated by the conductors through which the electrical current signal set flows. However, when the electrical resistances of various ones of the conductor portions through which the electrical currents of the electrical current signal set flow are not substantially the same, the resulting value provided by relationship (rel. #5) would no longer be proportional to the power dissipated by the conductors through which the electrical current signal set flows. Accordingly, the following particular relationship may, in some embodiments, be more appropriate:

$$\text{Value}=\Sigma_{n=1}^{N}IRMS_n^2*R_n \qquad \text{(rel. #6)}$$

where Value is a particular electrical current-based value, $IRMS_n^2$ is the mathematical square of an RMS value of an electrical current signal "n" in an electrical current signal set of "N" electrical current signals, and $R_n$, is the resistance of the conductor portion through which the electrical signal "n" flows, "N" being an integer at least equal to one.

In some embodiments, the electrical current-based limit (e.g., providing temperature curve 502 in FIG. 5B) is a value determined during a treatment or diagnostic procedure. In some embodiments, the electrical current-based limit is a value determined before a treatment or diagnostic procedure is commenced. In some embodiments, the electrical current-based limit is a value determined prior to insertion of a least a portion of the system (e.g., 100, 300, or 400) into a patient. In some embodiments, the value is stored in a memory device system (e.g., 130 or 330) of a data processing device system (e.g., 110 or 310). In some embodiments, the electrical current-based limit is a predetermined value stored in a memory device system (e.g., 130 or 330) of the data processing device system (e.g., 110 or 310). In some embodiments, the value of the electrical current-based limit may be determined experimentally (e.g., at a place of manufacture) using the first set of conductors (e.g., 317) according to a particular relationship (e.g., (rel. #5)). For example, RMS current values may be determined for various sets of the conductors (e.g., 317) using expected operating currents. If various ones of the conductors have different resistances (e.g., different resistances caused by different cross-sectional areas, different lengths, or different material compositions) the value of electrical current-based limit may be determined experimentally using the first set of conductors (e.g., 317) according to a particular relationship (e.g., (rel. #6)). In some embodiments, the resistance values of various ones of the conductors (e.g., at least some or all of the plurality of conductors (e.g., 317)) are measured values. In some embodiments, the resistance values of various one of the conductors (e.g., at least some or all of the plurality of conductors (e.g., 317)) are estimated or predicted values. In some embodiments, the resistance values may be predetermined values stored in a memory device system (e.g., 130 or 330) of the data processing device system (e.g., 110 or 310).

The first electrical current signal set associated with the electrical current-based limit may in some embodiments, be the same as the second set electrical current signal set. In a similar manner, the first set of one or more conductors may be the same as the second set of one or more conductors.

Figure 6A:
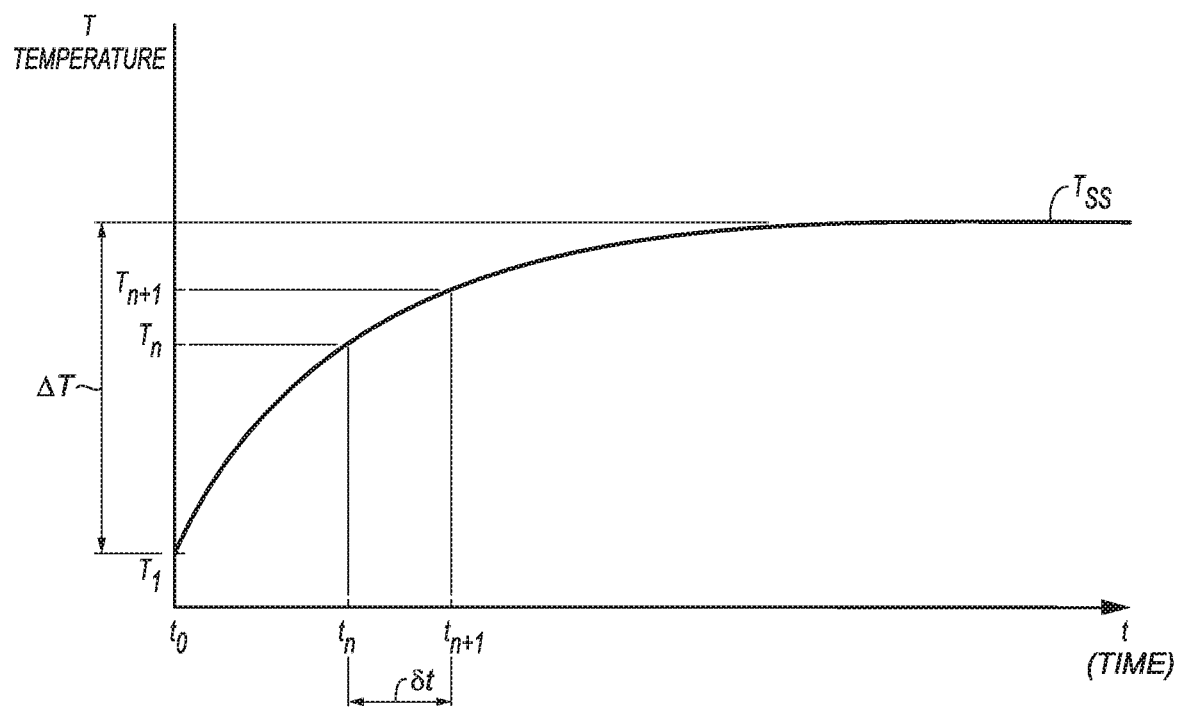
FIG. 6A shows a graph according to a first order model to predict temperature changes of a portion of a shaft member of a medical device system arising from the delivery of power via various conductors located within the shaft member, according to some embodiments.

As discussed above, in some embodiments, a controller (e.g., 324) may be configured to estimate the second temperature (e.g., $T_2$, $T_{2-1}$) based at least on a predictive model. For example, FIG. 6A is a graph according to a first order model (e.g., a first order thermal model) that may, in some embodiments, be included in a program stored in a memory device system (e.g., 130 or 330) that configures a data processing device system (e.g., 110 or 310) to predict temperature changes of a portion of the shaft member (e.g., 313 or 316) arising from the delivery of power or electrical current via various conductors (e.g., 317) located within the shaft member. The graph indicates a change in temperature $\Delta T$ of the portion of the shaft member (e.g., 313 or 316) from an initial or first temperature $T_1$ (which may or may not be the same as $T_1$ in FIG. 5B) to a steady-state temperature $T_{SS}$. A magnitude of the change in temperature $\Delta T$ may, according to some embodiments, be determined by the following relationship:

$$\Delta T = a * \Sigma_{n=1}^{N} IRMS_n^2 \qquad \text{(rel. \#7)}$$

where $IRMS_n^2$ is the mathematical square of an RMS value of an electrical current signal "n' in an electrical current signal set of "N" electrical current signals that are delivered through the shaft member, a is a coefficient that relates the electrical and thermal properties of the system, e.g., based on the amounts of various materials in the shaft member (e.g., 313 or 316) and other components of the system. The present inventors have determined that the sum of the squares of the electrical currents (e.g., in radio-frequency (RF) range) are linearly proportional to the change in the temperature $\Delta T$, according to some embodiments.

The following first order thermal relationship may be employed (e.g., in a program stored in a memory device system (e.g., 130 or 330) that configures a data processing device system (e.g., 110 or 310)) to determine various temperatures along the curve of the graph of FIG. 6:

$$T(t) = \left(1 - e^{-\frac{t}{\tau}}\right) * \Delta T + T_1 \qquad \text{(rel. \#8)}$$

where $T(t)$ is a temperature of the portion of the shaft member at a time "t" (i.e., as measured from a time "t=0" of the first temperature $T_1$; $\Delta T$ is the magnitude in the change in temperature from the first temperature $T_1$ to the steady-state temperature $T_{SS}$, and $\tau$ is a time constant for the first order thermal model. In some embodiments, the time constant $\tau$ is determined empirically. For example, known electrical currents may be delivered to a known number of transducers and the temperature of the portion of the shaft member may be measured starting from a time t=0, when the electrical currents are first applied. Rel. #8 may be curve fitted to plot of the measured temperatures and the value of $\tau$ may be determined from the curve fitted equation. In some embodiments, the values may be manually tuned to provide adequate margin based on experimentation.

Figure 6B:
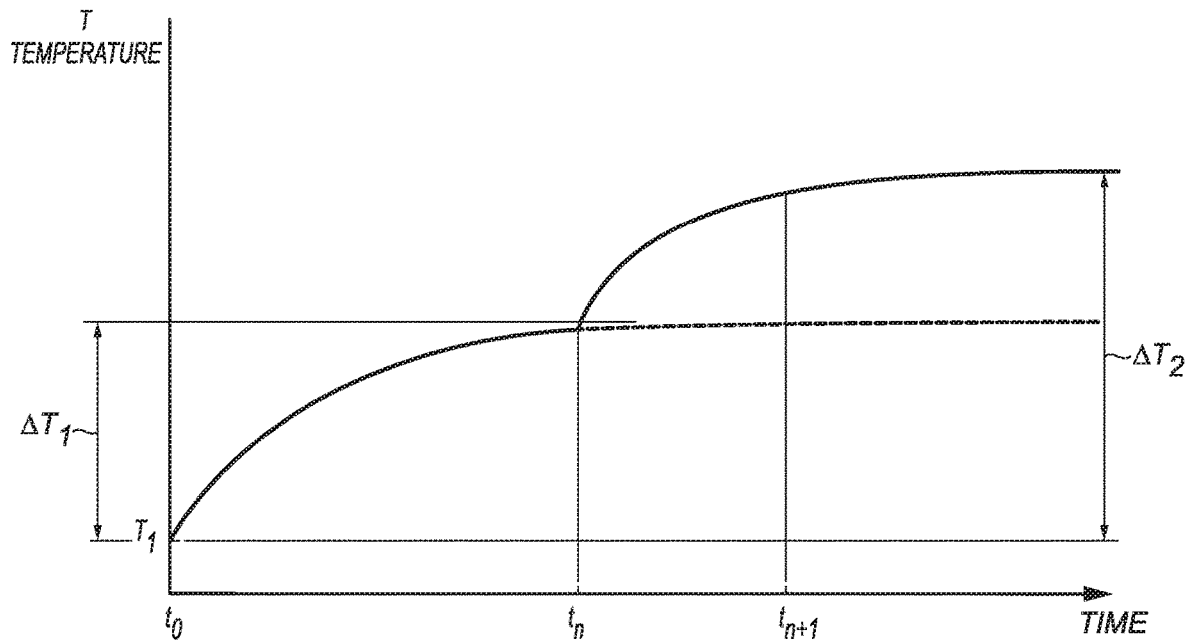
FIG. 6B shows an example of how the model, e.g., of FIG. 6A, would change when the sum of the squares of the delivered electrical currents increase at time $t_n$ (e.g., via an increase in a magnitude of the delivered currents) with an inflection point indicated at time $t_n$, according to some embodiments.
Figure 6C:
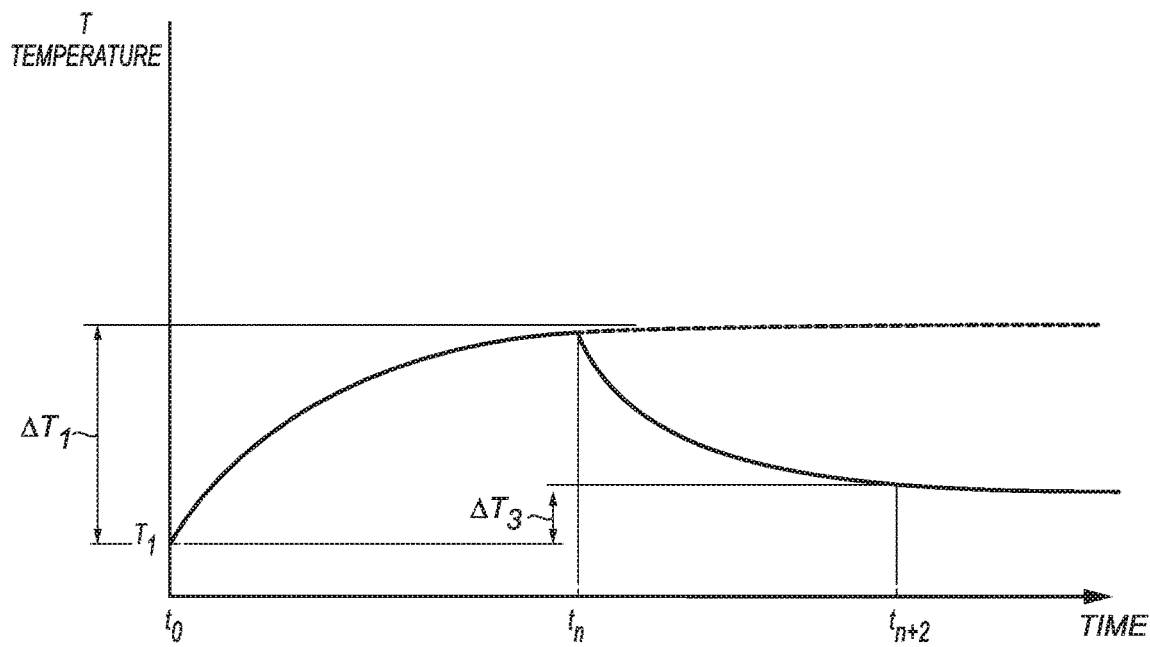
FIG. 6C shows an example of how the model, e.g., of FIG. 6A or 6B, would change when the sum of the squares of the delivered electrical currents decreases at time $t_n$ (e.g., via a decrease in a magnitude of the delivered currents), according to some embodiments.

It is noted that relationship (rel. #8) is dependent on $\Delta T$ which is itself dependent on the sum of the squares of the electrical currents (e.g., the sum of the squares of the RMS electrical current values). Accordingly, if the sum of the squares of the electrical currents varies during the delivery thereof, the value of the $\Delta T$ accordingly changes, and output of the model to determine the temperature of the portion of the shaft member (e.g., 313 or 316) at a particular time $t_n$ also changes. (Note that "n" as a subscript with time "t", e.g., $t_n$, $t_{n+1}$, etc., is intended to be a different variable as compared to "n" used in rel. #5, rel. #6, and rel. #7, discussed above, but is the same variable as "n" used in rel. #9 and rel. #10, discussed below.) For example, FIG. 6B shows an example of how the graphed model would change when the sum of the squares of the delivered electrical currents increase at time $t_n$ (e.g., via an increase in a magnitude of the delivered currents) with an inflection point in the graph indicated at time $t_n$. In this case, determining a temperature of the portion of the shaft member at a time $t_{n+1}$ would be based on the new change in temperature $\Delta T_2$ associated with the increase in the sum of the squares of the delivered electrical currents (i.e., as compared with the original change in temperature $\Delta T_1$). FIG. 6C shows an example of how the graphed model would change when the sum of the squares of the delivered electrical currents decreases at time $t_n$ (e.g., via a decrease in a magnitude of the delivered currents). In this case, determining a temperature of the portion of the shaft member at a time $t_{n+2}$ would be determined on the new change in temperature $\Delta T_3$ associated with the decrease in the sum of the squares of the delivered electrical currents (i.e., as compared with the original change in temperature $\Delta T_1$). It is noted in both these examples, that $\Delta T_2$ and $\Delta T_3$ are the changes in temperature of the portion of the shaft member from the first temperature $T_1$ to a respective steady state temperature. The following relationship accordingly may be used to determine the temperature of the portion of the shaft member (e.g., 313 or 316) at a particular time $t_{n+1}$ on the basis of a temperature $T_{[n]}$ of the portion of the shaft member at preceding time $t_n$:

$$T_{[n+1]} = \left[1 - e^{-\frac{\delta t}{\tau}}\right] * (\Delta T_{[n]} + T_0) + T_{[n]} * e^{-\frac{\delta t}{\tau}} \qquad \text{(rel. \#9)}$$

where $T_{[n+1]}$ is the temperature of the portion of the shaft member at time $t_{n+1}$ under the influence of the a particular sum of the squares of the delivered current; $T_0$ is a temperature that the portion of the shaft member would approach in absence of any delivery of any electrical power or current via a particular conductor set located in the shaft member; $\Delta T_{[n]}$ is the projected change in temperature of the portion of the shaft member from $T_0$ to the steady-state temperature $T_{SS}$ under the influence of the a particular sum of the squares of the delivered current; $T_{[n]}$ is the temperature associated with the portion of the shaft member measured, estimated, or predicted at a preceding time $t_n$; $\delta t$ is the time difference between $t_{n+1}$ and $t_n$; and $\tau$ is a time constant for the first order thermal model. It is noted that in some embodiments, $T_0$ is an ambient temperature that the portion of the shaft member would approach in absence of any delivery of any electrical power or current via the particular conductor set located in the shaft member. For example, if the shaft undergoes any heating (for example, by way of any power delivery through the shaft member via a conductor set other than the particular conductor set), then the portion of the shaft member would approach an ambient temperature in absence of any delivery of any delivery of any electrical power or current via the particular conductor set. In some embodiments, $T_O$ is a temperature slightly higher than ambient (e.g., 1 to 4 degrees Celsius) if relatively low levels of electrical current are delivered via a conductor set other than the particular conductor set in absence in absence of any delivery of any delivery of any electrical power or current via the particular conductor set. Such low levels of electrical current may be delivered, for various reasons including in the sensing of electrical voltages.

In various embodiments, multiple sets of the transducers (e.g., 306) are sequentially activated such that sequential deliveries of multiple electrical current signal sets are required to be delivered through the shaft member (e.g., 313 or 316). Typically, each electrical current signal set is delivered via a respective set of conductors (e.g., 317) located in the shaft member (e.g., 313 or 316). According to various embodiments, at least one of the respective sets of conductors (e.g., 317) includes a conductor that is not included in another of the respective sets of the conductors (e.g., 317). For example, different sets of transducers (e.g., 306) may require sequential activation, with each set of transducers (e.g. 306) connected to a different set of the conductors (e.g., 317). Accordingly, if a first delivery of electrical power or a first delivery of an electrical current signal set has been delivered via a first set of the conductors (e.g., 317), a resulting temperature of a portion of the shaft member (e.g., 313 or 316) may be sufficiently high at a desired start of a subsequent second delivery of electrical power (or a subsequent second delivery of an electrical current signal set) that is to be delivered via a second set of the conductors (e.g., 317), that the temperature of the portion of the shaft member (e.g., 313 or 316) would increase undesirably to level above a temperature limit (e.g., 500) at some point during the subsequent second delivery of electrical power or the subsequent second delivery of an electrical current signal set. Accordingly, in some embodiments in which recent deliveries of electrical power or electrical current (e.g., via various conductors (e.g., 317) located with the shaft member (e.g., 313 or 316)) have taken place in the recent past, the controller (e.g., 324 or other data processing device system 110) may be configured by a program stored in a memory device system (e.g., 130 or 330), the program configured according to, e.g., one or more predictive models discussed above, to determine a future temperature of the portion of the shaft member, based on a measurement, model, or prediction of the temperature of the portion of the shaft member at the desired start of the subsequent second delivery of electrical power or electrical current signal set. The controller (e.g., 324 or other data processing device system 110) may then be configured by the program to determine by how much the output-power limit or the electrical current-based limit should be adjusted based on a number of factors including by way of non-limiting example a measured or modeled shaft member temperature, a particular temperature limit, particular transducers (e.g., 306) targeted for activation, the number of particular transducers (e.g., 306) targeted for activation, a desired amount of electrical current that is to be delivered by a respective conductor (e.g., 317) to a particular transducer, an expected activation duration, and any cool down or required dwell times between successive activations.

Figure 7:
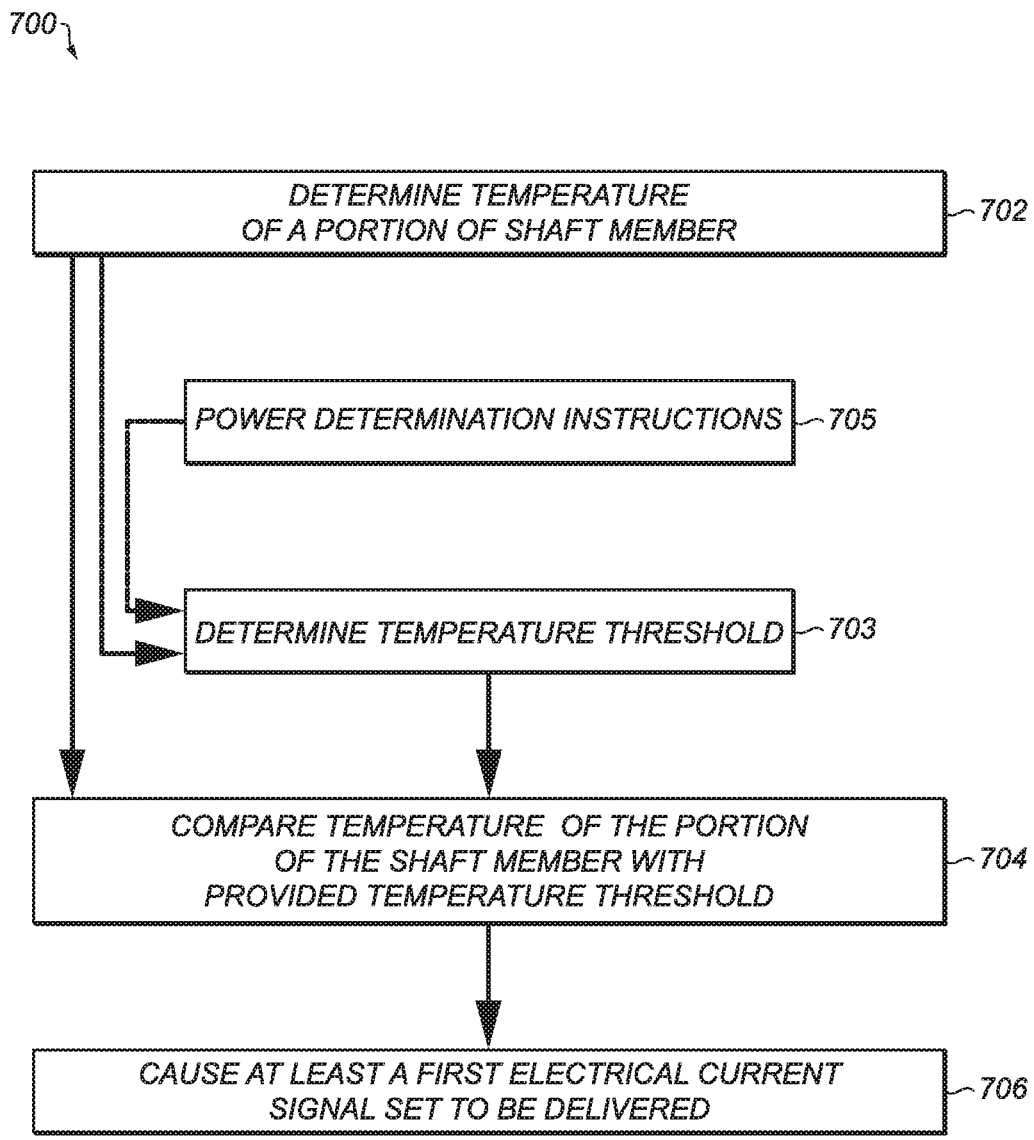
FIG. 7 is a block diagram of a method of controlling temperature of at least a portion of a shaft member of a medical device system by controlling delivery of electrical current within the medical device system, according to some embodiments.

FIG. 7 is a block diagram of a method 700 employed according to some example embodiments. In various example embodiments, a memory device system (e.g., 130 or 330) is communicatively connected to a data processing device system (e.g., 110 or 310) and stores a program executable by the data processing device system to cause the data processing device system to execute method 700 via interaction with at least, for example, a transducer-based device (e.g., transducer-based device associated with system 100 or 300). In these various embodiments, the program may include instructions configured to perform, or cause to be performed, various ones of the instructions associated with method 700. In some embodiments, method 700 may include a subset of the associated blocks or additional blocks than those shown in FIG. 7. In some embodiments, method 700 may include a different sequence between various ones of the associated blocks than those shown in FIG. 7.

In various embodiments, the data processing device system (e.g., 110, 310, or 324) is communicatively connected to a transducer set (e.g., a transducer set including one or more transducers (e.g., 306). In some embodiments, a conductor set (e.g., a conductor set including one or more conductors (e.g., 317)) is provided, with each conductor (e.g., 317) in the conductor set electrically coupled or connected to a respective transducer (e.g. 306) in the transducer set (although one-to-many connections may occur in other embodiments), and at least a portion of each conductor in the conductor set located within a shaft member (e.g., 313 or 316).

Block 702 may be associated with instructions (e.g., temperature determination instructions) configured to cause the data-processing device system (e.g., 110, 310, or 324) to determine, predict, or estimate a temperature of at least a portion of the shaft member (e.g., 313 or 316). For example, in some embodiments, the temperature determination instructions are configured to cause the data-processing device system (e.g., 110, 310, or 324) to determine the temperature of the portion of the shaft member (e.g., 313 or 316) on the basis of sensor data provided via the input-output device system (e.g., 120) from various sensors (e.g., 342*a* or 342*b*), which may be included in the input-output device system (e.g., 120). In some embodiments, the temperature determination instructions are configured to cause the data-processing device system (e.g., 110, 310, or 324) to determine the temperature of the portion of the shaft member (e.g., 313 or 316) on the basis of a predictive model (for example, as described in this disclosure). In some embodiments, the temperature determination instructions are configured to cause the data-processing device system (e.g., 110, 310, or 324) to determine the temperature of the portion of the shaft member (e.g., 313 or 316) on the basis of at least both sensor-provided data and a predictive model.

According to various embodiments, the temperature determination instructions (e.g., associated with block 702) are configured to cause the data-processing device system (e.g., 110, 310, or 324) to determine the temperature of at least the portion of the shaft member (e.g., 313 or 316) at various particular times. The particular time for which the temperature of the portion of the shaft member (e.g., 313 or 316) is determined (such as, but not limited to, predicted, measured, or estimated) may be based on the type of temperature threshold the determined, predicted or estimated temperature of the portion of the shaft member is compared against at block 704, discussed below, according to some embodiments. In some embodiments, the temperature determination instructions are configured to cause the data-processing device system (e.g., 110, 310, or 324) to determine the temperature of at least a portion of the shaft member (e.g., 313 or 316) at a particular time prior to an anticipated start of the first time period (e.g., the first time period here being when the subsequent delivery of the first electrical current signal set is to occur, according to some embodiments, in contrast to, e.g., the first time period $TP_1$ discussed above with respect to FIG. 5B). In some embodiments, the temperature determination instructions are configured to cause the data-processing device system (e.g., 110, 310, or 324) to determine the temperature of at least the portion of the shaft member (e.g., 313 or 316) at an anticipated start of the first time period. In some embodiments, the temperature determination instructions are configured to cause the data-processing device system (e.g., 110, 310, or 324) to determine the temperature of at least the portion of the shaft member (e.g., 313 or 316) at an anticipated time occurring during the first time period. In some embodiments, the temperature determination instructions are configured to cause the data-processing device system (e.g., 110, 310, or 324) to determine the temperature of at least a portion of the shaft member (e.g., 313 or 316) at an anticipated time occurring at the end of the first time period. Block 704 may be associated with instructions (e.g., temperature comparison instructions) configured to cause the data processing device system (e.g., 110, 310, or 324) to compare the determined temperature (e.g., per block 702) of the portion of the shaft member with a provided temperature threshold.

Block 706 may be associated with instructions (e.g., transducer activation instructions or electrical current signal set delivery instructions) configured to cause the data processing device system (e.g., 110, 310, or 324) to cause at least a first electrical current signal set to be delivered, via at least one conductor (e.g., 317) in the conductor set, to at least one transducer (e.g., 306) in the transducer set for at least a first time period. In various embodiments the delivered at least a first electrical current signal set is sufficient to cause tissue ablation via the at least one transducer. In various embodiments, the data-processing device system (e.g., 110, 310, or 324) is communicatively connected via the input-output device system (e.g., 120) to an energy source device system (e.g., 340) to cause the first electrical current signal set to be delivered from the energy source device system to the at least one transducer (e.g., 306) in the transducer set. According to various embodiments, the transducer activation instructions (or electrical current signal set delivery instructions) of block 706 may be associated with particular instructions configured to cause the data processing device system (e.g., 110, 310, or 324) to cause delay or restriction of the delivery of the at least the first electrical current signal set in a case where the comparison of the estimated temperature of the portion of the shaft member with the provided temperature threshold indicates that the estimated temperature of the portion of the shaft member exceeds the provided temperature threshold. For example, in some embodiments, the determined temperature is a particular temperature of the portion of the shaft member (e.g., 313 or 316) at an anticipated start of the first time period. Accordingly, the delivery of at least the first electrical current signal set may be delayed or restricted until the particular temperature of the portion of the shaft member (e.g., 313 or 316) at the anticipated start of the first time period has dropped below the temperature threshold. For instance, in some embodiments, a determined temperature of the portion of the shaft member (e.g., 313 or 316) above the provided temperature threshold results in a delay in the anticipated start of the first time period to allow time for the shaft member to cool in a case where electrical power delivery through one or more conductors within the shaft member is ceased or reduced during the delay or restriction period to permit such cooling. In some of these embodiments, the temperature threshold may be provided by a temperature limit that the portion of the shaft member (e.g., 313 or 316) should not exceed or be determined not to exceed. In this regard, in some embodiments, the temperature threshold may be, e.g., the temperature limit 500 in cases where the determined temperature of the portion of the shaft member (e.g., per block 702) is a future temperature of the portion of the shaft member (e.g., 313 or 316) that would exist should the subsequent delivery of the first electrical current signal set to be permitted to immediately occur. Or, in some embodiments, the temperature threshold may be some temperature below the temperature limit 500 in cases where the determined temperature of the portion of the shaft member (e.g., per block 702) is a present temperature of the portion of the shaft member (e.g., 313 or 316), where the difference between the temperature limit 500 and the temperature threshold reflects an expected amount of temperature increase in the portion of the shaft member (e.g., 313 or 316) due to the subsequent delivery of the first electrical current signal set, should such subsequent delivery be permitted to immediately occur. Other temperature thresholds may be implemented in other embodiments. The discussions associated with FIGS. 8A and 8B, below, provide some example temperature threshold determinations. In any event, a determined temperature of the portion of the shaft member (e.g., 313 or 316) that exceeds the respective temperature threshold (e.g., per the comparison associated with block 704) may result in a delay or restriction of delivery of the subsequent first electrical current signal set (e.g., per block 706) in order to allow at least the portion of the shaft member (e.g., 313 or 316) to sufficiently cool.

In some embodiments, the determined temperature (e.g., per block 702) is a particular temperature of the portion of the shaft member (e.g., 313 or 316) at a particular anticipated time during the first time period (e.g., the first time period being when the subsequent delivery of the first electrical current signal set is to occur, according to some embodiments). For example, in some embodiments, the temperature threshold may be provided by a particular temperature limit (e.g., temperature limit 500 described above), and the transducer activation instructions are configured to cause the data processing device system (e.g., 110, 310, or 324) to cause a delay or restriction of the delivery of the at least the first electrical current signal set in a case where the comparison (e.g., per block 704) of the determined temperature of the portion of the shaft member at the particular anticipated time during the first time period indicates that the temperature would exceed the temperature threshold/limit.

It is noted according to some embodiments, that the provided temperature threshold indicates a particular temperature of the portion of the shaft member (e.g., 313 or 316), the particular temperature insufficient to cause thermally-induced tissue cellular damage (e.g., at least via tissue contact with the portion of the shaft member (e.g., 313 or 316)), but exceeding the particular temperature would cause or be determined to cause thermally-induced tissue cellular damage (e.g., at least via tissue contact with the portion of the shaft member (e.g., 313 or 316)). It is noted that different embodiments are described herein, and accordingly, the described temperature thresholds may vary or correspond to different particular times at least among some of the different embodiments. The different particular times may vary depending on the context of the particular embodiment. The discussions associated with FIGS. 8A and 8B, below, provide some example temperature threshold determinations.

Block 703, which is optional according to some embodiments, may be associated with instructions (e.g., temperature threshold determination instructions) that, when executed, cause the data processing device system (e.g., 110, 310, or 324) to determine the temperature threshold as a particular temperature of the portion of the shaft member (e.g., 313 or 316) at some particular time during the first time period, if the first electrical current signal set were to be delivered, absent the delay or restriction discussed with respect to block 706, above, via the at least one conductor (e.g., 317) in the conductor set to the at least one transducer (e.g., 306) in the transducer set for the first time period, the particular temperature insufficient to cause thermally-induced tissue cellular damage (e.g., at least via tissue contact with the portion of the shaft), but if the particular temperature is exceeded, thermally-induced tissue cellular damage (e.g., at least via contact with the portion of the shaft member) would be caused or be determined to be caused. In some embodiments, the determined temperature threshold may be provided by a particular temperature limit (e.g., 500) as discussed above.

Figure 8A:
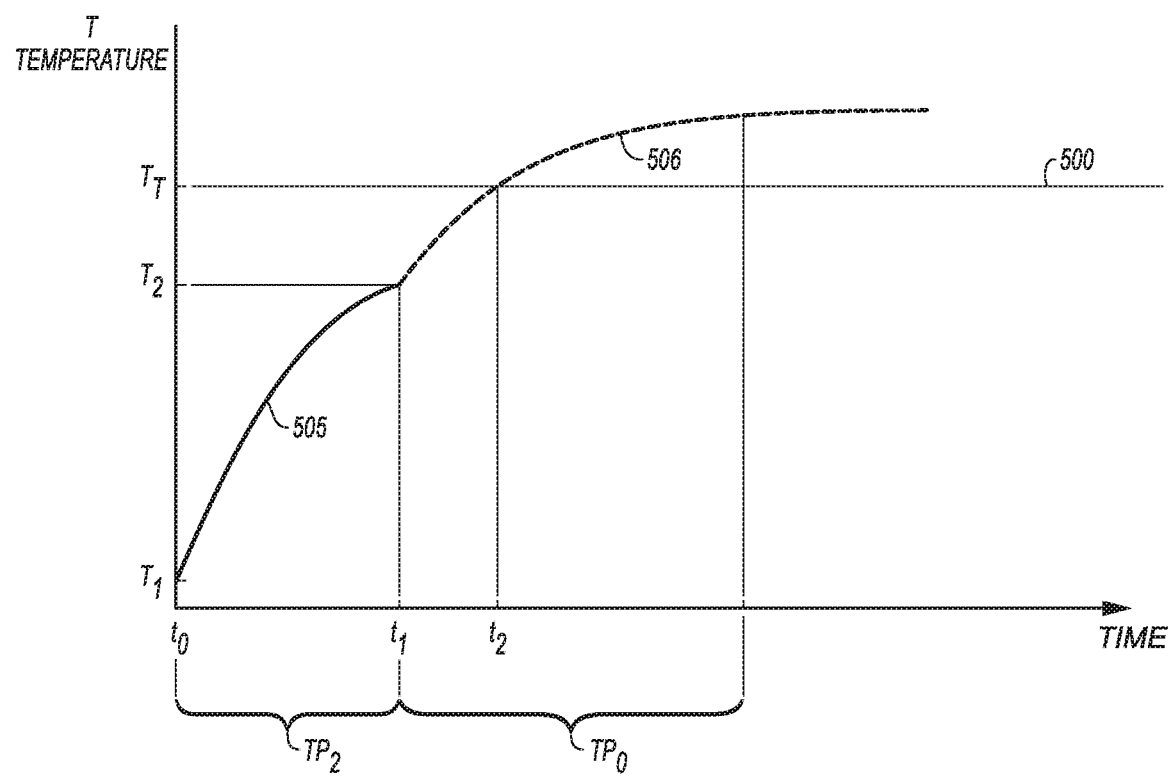
FIGS. 8A and 8B include graphs in which it is proposed to deliver a first electrical current signal set via at least one conductor in a medical device system for a first time period $TP_n$ after a previous delivery of at least a second electrical current signal set that has increased a temperature of a portion of a shaft member of the medical device system, according to some embodiments.

For example, FIG. 8A includes a graph in which it is proposed to deliver the first electrical current signal set via the at least one conductor (e.g., 317) for a first time period $TP_0$. According to some embodiments, the proposed delivery of the first electrical current signal set occurs after a previous delivery of at least a second electrical current signal set that has increased a temperature (e.g., represented by curve 505) of the portion of the shaft member (e.g., 313 or 316) from a temperature $T_1$ (e.g., which may be an ambient temperature in some embodiments) to temperature $T_2$ at time $t_1$. If the delivery of the first electrical current signal set was to start immediately upon completion of the previous delivery of the second electrical current signal set without delay at time $t_1$, then the temperature (e.g., represented by broken line curve 506) of the portion of the shaft member (e.g., 313 or 316) would undesirably increase above a temperature threshold $T_T$ at time after time $t_2$. In some embodiments, the temperature threshold $T_T$ corresponds to a temperature limit (e.g., temperature limit 500 described above, in some embodiments). In some embodiments, the temperature threshold $T_T$ is provided as a predetermined value stored in the memory device system (e.g., 130).

It is noted in FIG. 8A that curve 505 and broken line curve 506 meet at an inflection point according to some embodiments in which the power associated with the proposed delivery of the first electrical current signal set is different than the power associated with the previous delivery of the second electrical current signal set. In some embodiments in which the power associated with the proposed delivery of the first electrical current is the same as the power associated with the previous delivery of the second electrical current signal set, no inflection point will be present and curves 505 and 506 will at least generally form a smooth continuous curve, assuming there is no cessation of power delivery during the time period associated with curves 505 and 506.

Figure 8B:
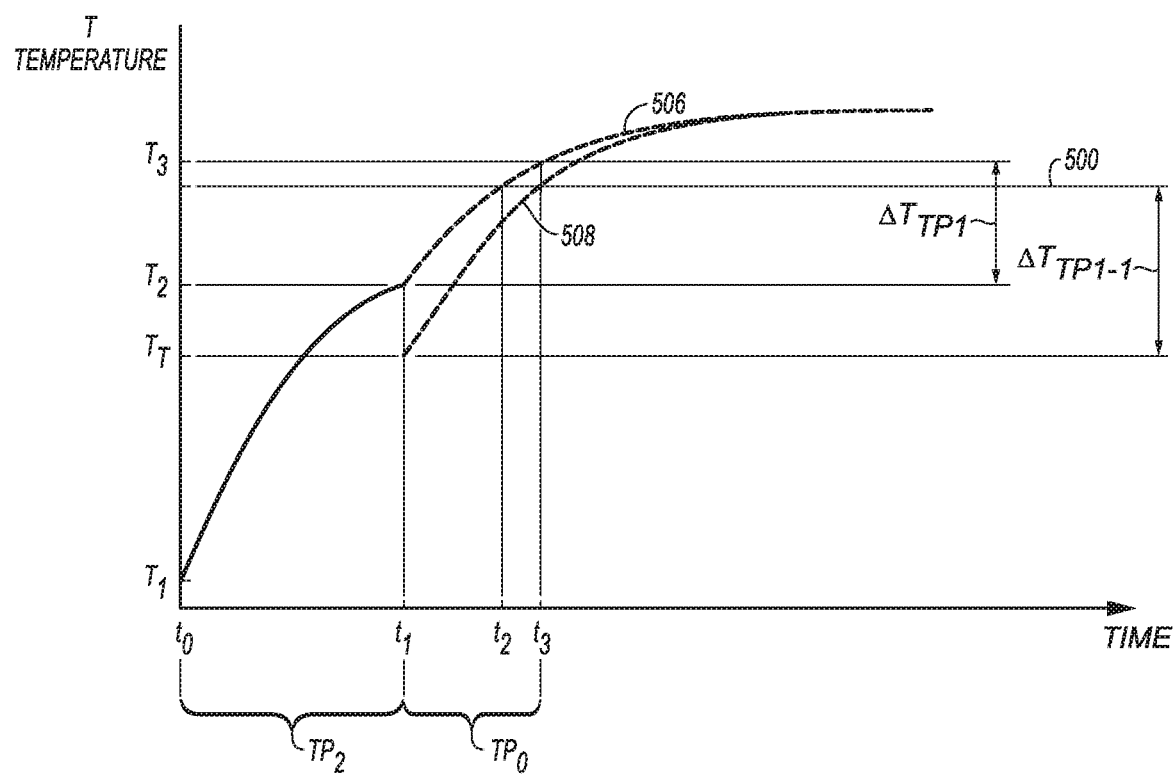

In some embodiments, the temperature threshold determination instructions associated with block 703 are configured to cause the data processing device system (e.g., 110, 310, or 324) to determine the temperature threshold as a particular temperature of the portion of the shaft member (e.g., 313 or 316) at the start of the first period, if the first electrical current signal set was to be delivered, absent the delay or restriction, via the at least one conductor in the conductor set to the at least one transducer in the transducer set for the first time period, the particular temperature insufficient to cause the portion of the shaft member (e.g., 313 or 316) to heat sufficiently to cause thermally-induced tissue cellular damage (e.g., at least via contact with the portion of the shaft member (e.g., 313 or 316)) throughout the first time period, but if the particular temperature is exceeded, the portion of the shaft member (e.g., 313 or 316) would heat sufficiently at some point in the first time period to cause or be determined to cause thermally-induced tissue cellular damage (e.g., at least via contact with the portion of the shaft member (e.g., 313 or 316)). For example, FIG. 8B includes a graph in which it is proposed to deliver the first electrical current signal set via the at least one conductor (e.g., 317) for a first time period $TP_0$. According to some embodiments, the proposed delivery of the first electrical current signal set occurs after a previous delivery of at least a second electrical current signal set that has increased a temperature of the portion of the shaft member (e.g., 313 or 316) from a temperature $T_1$ (e.g., which may be an ambient temperature in some embodiments) to temperature $T_2$ at time $t_1$. If the delivery of the first electrical current signal set was to start immediately upon completion of the previous delivery of the second electrical current signal set without delay at time $t_1$, then the temperature (e.g., as represented by broken line curve 506) of the shaft member (e.g., 313 or 316) would increase from temperature $T_2$ under the influence of the delivery of the first electrical current signal set to an undesirable level above the temperature limit 500 at and after time $t_2$. In FIG. 8B, an inflection point exists between the graph portions associated with the previous delivery of power and the proposed delivery of power indicating power differences between the previous delivery of power and the proposed delivery of power according to some embodiments, although such differences in power delivery need not occur as discussed above.

In FIG. 8B, the temperature threshold is indicated as temperature threshold $T_T$ that corresponds to a start temperature to avoid having the portion of the shaft member (e.g., 313 or 316) rise to a temperature greater than the temperature limit 500 under the influence of the delivery of the first electrical current signal set during first time period $TP_0$. In FIG. 8B, the temperature (as indicated by broken line curve 508) of the portion of the shaft member (e.g., 313 or 316) would increase under the influence of the delivery of the first electrical current signal set during the first time period $TP_0$ from a start temperature equal to the temperature threshold $T_T$ and reach a temperature that does not exceed the temperature limit 500 at the immediate conclusion of the first time period $TP_0$. According to some embodiments, the temperature (as indicated by broken line curve 508) of the portion of the shaft member (e.g., 313 or 316) need not reach a steady-state temperature at the end of the first time period $TP_0$, but rather, reach a temperature that does not exceed the temperature limit 500. In other words, the temperature threshold determination instructions (e.g., Block 703) are configured, in some embodiments, to determine the temperature threshold $T_T$ such that a temperature change of the portion of the shaft member (e.g., 313 or 316) resulting from the delivery of the first electrical current signal set for the first time period $TP_0$ would not result in a temperature of the portion of the shaft member at the end of the first time period $TP_0$ exceeding the temperature limit 500. In various embodiments, the temperature change of the portion of the shaft member (e.g., 313 or 316) is a projected temperature change determined according to a particular relationship. For example, relationship (rel. #9) may be employed to determine temperature change in some embodiments.

According to some embodiments, the temperature threshold determination instructions associated with block 703 may be configured to determine the temperature threshold based at least on the temperature determined according to the instructions associated with block 702. For example, in some embodiments, the determined temperature indicates a particular temperature of the portion of the shaft member at the start of the first time period $TP_0$, assuming no delay is caused between the first time period $TP_0$ and the second time period $TP_2$. For example, in FIG. 8B, the determined temperature may be indicated as temperature $T_2$ at the start of the first time period $TP_0$ (i.e., at time $t_1$), or as the final temperature $T_3$ of the portion of the shaft member (e.g., 313 or 316) at the end of the first time period $TP_0$ (i.e., at time $t_3$) under the influence of the delivery of the first electrical current signal set, if the start of the delivery of the first electrical current signal set was to occur immediately at time $t_1$. In some embodiments, the determined temperature may be indicated as temperature $T_2$ as a temperature of the portion of the shaft member (e.g., 313 or 316) at the end of a delivery of electrical current or electrical power through the shaft member that has occurred (e.g., at the end of time period $TP_2$ at time $t_1$) before the desired delivery of the first electrical current signal set. In some embodiments, the determined temperature may be indicated as temperature $T_2$ as a temperature of the portion of the shaft member (e.g., 313 or 316) at the end of a delivery of electrical current or electrical power through the shaft member that has occurred (e.g., at the end of time period $TP_2$ at time $t_1$) immediately before the desired delivery of the first electrical current signal set. The determined temperature may be a predicted future temperature of the portion of the shaft member (e.g., 313 or 316) at some particular time during the first period (e.g., $t_2$) if the first electrical current signal set was to be delivered, absent the delay, via the at least one conductor in the conductor set to the at least one transducer in the transducer set for the first time period. Determination of the temperature threshold based at least on the determined temperature is described in further detail below.

In some embodiments, the program configured to implement method 700 in FIG. 7 may include power determination instructions (e.g., instructions that may be associated with block 705) that are configured to determine particular data responsive to power dissipation associated with at least the delivery of at least a particular electrical current signal set (e.g., the first electrical current signal set) via the at least one conductor in the conductor set. For example, the particular data may be based on the sum of the squares of a parameter of the first electrical current signal set. In some embodiments, the particular data may be determined according to a particular relationship. For example, in some embodiments, the particular relationship may be provided by (rel. #7), above, which relates $\Delta T$ to the power dissipation associated with the delivery of the first electrical current signal (e.g., $IRMS_n^2$). In some embodiments, the temperature threshold determination instructions associated with block 703 are configured to determine the temperature threshold based at least on the particular data associated with the power dissipation as described below.

According to some embodiments, the final temperature $T_3$ (FIG. 8B) of the portion of the shaft member (e.g., 313 or 316) may be determined by relationship (rel. #9), above, which is herein indicated as relationship (rel. #10) to indicate the use of these particular input variables:

$$T_3 = \left[1 - e^{-\frac{\delta t}{\tau}}\right] * (\Delta T_1 + T_0) + T_2 * e^{-\frac{\delta t}{\tau}} \quad \text{(rel. #10)}$$

where $T_3$ is the temperature of the portion of the shaft member at time $t_3$ under the influence of a particular sum of the squares of the delivered first electrical current signal; $T_0$ is a temperature that the portion of the shaft member would approach in absence of any delivery of any electrical power or current via a conductor set located in the shaft member; $\Delta T_1$ is the projected change in temperature of the portion of the shaft member from the temperature $T_0$ to a steady-state temperature under the influence of a particular power or current-based value; $T_2$ is the temperature associated with the portion of the shaft member determined at a preceding time $t_1$; $\delta t$ is the time difference between time $t_3$ and time $t_1$ (i.e., a span of time equal to the first time period $TP_0$); and $\tau$ is a time constant for the first order thermal system.

If the final temperature $T_3$ is determined to be greater than the temperature limit 500, the temperature threshold determination instructions associated with block 703 may be configured to determine that the predicted final temperature $T_3$ would be unacceptable as thermally-induced tissue cellular damage may arise or may be determined to arise if the portion of the shaft member (e.g., 313 or 316) were to be allowed to reach the predicted value of final temperature $T_3$. In some embodiments, the temperature threshold determination instructions associated with block 703 may include instructions configured to determine a temperature change $\Delta T_{TP1}$ between the predicted final temperature $T_3$ and temperature $T_2$. Temperature change $\Delta T_{TP1}$ indicates the change in temperature that the portion of the shaft member (e.g., 313 or 316) would undergo under the influence of the delivery of the first electrical current signal set delivered for time period $\delta t$ (i.e., the duration of the first time period). In this regard, in some embodiments, the determined temperature (e.g., per block 702) is a present temperature of the portion of the shaft member (e.g., 313 or 316) at the start of the first time period (e.g. $TP_0$) if the first electrical current signal set was to be delivered, absent any delay or restriction, via the at least one conductor in the conductor set to the at least one transducer in the transducer set for the first time period, and, in at least this case, the provided temperature threshold would be a particular temperature of the portion of the shaft member that is at least $\Delta T_{TP1}$ degrees Celsius below a predetermined temperature limit (e.g., temperature limit 500) that, if exceeded, is predetermined to cause thermally-induced tissue cellular damage. In this regard, it may be stated that $\Delta T_{TP1}$ is a temperature increase that would occur if the first electrical current signal set was to be delivered, absent any delay or restriction, via the at least one conductor in the conductor set to the at least one transducer in the transducer set for the first time period.

According to various embodiments, the temperature threshold determination instructions associated with block 703 are configured to determine the temperature threshold $T_T$ based at least on various factors including at least some of those listed above with respect to relationship (rel. #10). These related factors may include, according to some embodiments, the temperature determined (e.g., $T_2$) according to the instructions of block 702. These related factors may include, according to some embodiments, particular data associated with power dissipation (e.g., $\Delta T_1$) that would be associated with the delivery of the first electrical current signal set. In some embodiments, the factors may include a duration of the first time period $TP_0$. For example, the duration of the first time period $TP_0$ may be used to determine temperature change $\Delta T_{TP1}$ which in turn may be employed to determine temperature threshold $T_T$ as described below in this disclosure. The duration of the first time period $TP_0$ may reflect various time durations including a required duration of an activation time of various transducers (e.g., 306).

In some embodiments, the temperature threshold determination instructions associated with block 703 are configured to determine the temperature threshold based at least on a provided temperature limit, the provided temperature limit indicating a particular temperature of the portion of the shaft member, the particular temperature insufficient to cause thermally-induced tissue cellular damage (e.g., at least via tissue contact with the portion of the shaft), but if the particular temperature is exceeded, thermally-induced tissue cellular damage (e.g., at least via contact with the portion of the shaft member) would be caused or would be determined to be caused. For example, once the temperature change $\Delta T_{TP1}$ is known, the temperature threshold determination instructions can include instructions that compare the predicted final temperature $T_3$ with the temperature limit 500 and determine the temperature threshold $T_T$ to have a value that is lower than the temperature limit 500 by an amount $\Delta T_{TP1-1}$ at least equal to the temperature change $\Delta T_{TP1}$ when the predicted final temperature $T_3$ is determined to exceed the temperature limit 500. An example is shown in FIG. 8B, where the temperature threshold $T_T$ is determined to be at least $\Delta T_{TP1}$ less than the temperature limit 500 as indicated by $\Delta T_{TP1-1}$. If the predicted final temperature $T_3$ is determined to not exceed the temperature limit 500, then the temperature determination instructions may not set a temperature threshold and may allow for immediate delivery of the first electrical current at time $t_1$, according to the transducer activation instructions associated with block 706.

According to some embodiments associated with FIG. 7, the temperature determination instructions associated with block 702 are configured to cause the data processing device system (e.g., 110, 310, or 324) to determine the temperature that the portion of the shaft member (e.g., 313 or 316) has or would have at a particular time. In some embodiments, the system (e.g., 100, 300, or 400) includes at least a first temperature sensor, e.g., as discussed above, configured to provide data responsive to the temperature of the portion of the shaft member, and the temperature determination instructions associated with block 702 are configured to determine the temperature of the portion of the shaft member (e.g., 313 or 316) based on the data. In some embodiments, the first temperature sensor is located on or in the shaft member. For example, the first temperature sensor may be provided by sensor 342a or 342b. In some embodiments, the first temperature sensor is provided at least in part by a first conductor, at least a portion thereof included in the shaft member, and wherein the temperature determination instructions are configured to estimate the temperature of the portion of the shaft member based at least on a resistance of at least part of the first conductor (e.g. as described above in this disclosure). In some embodiments, the temperature determination instructions associated with block 702 are configured to determine or estimate the temperature of the portion of the shaft member (e.g., 313 or 316) based at least on a predictive model. For example, a predictive model based on at least relationship (rel. #9) may be implemented in some embodiments.

Figure 8C:
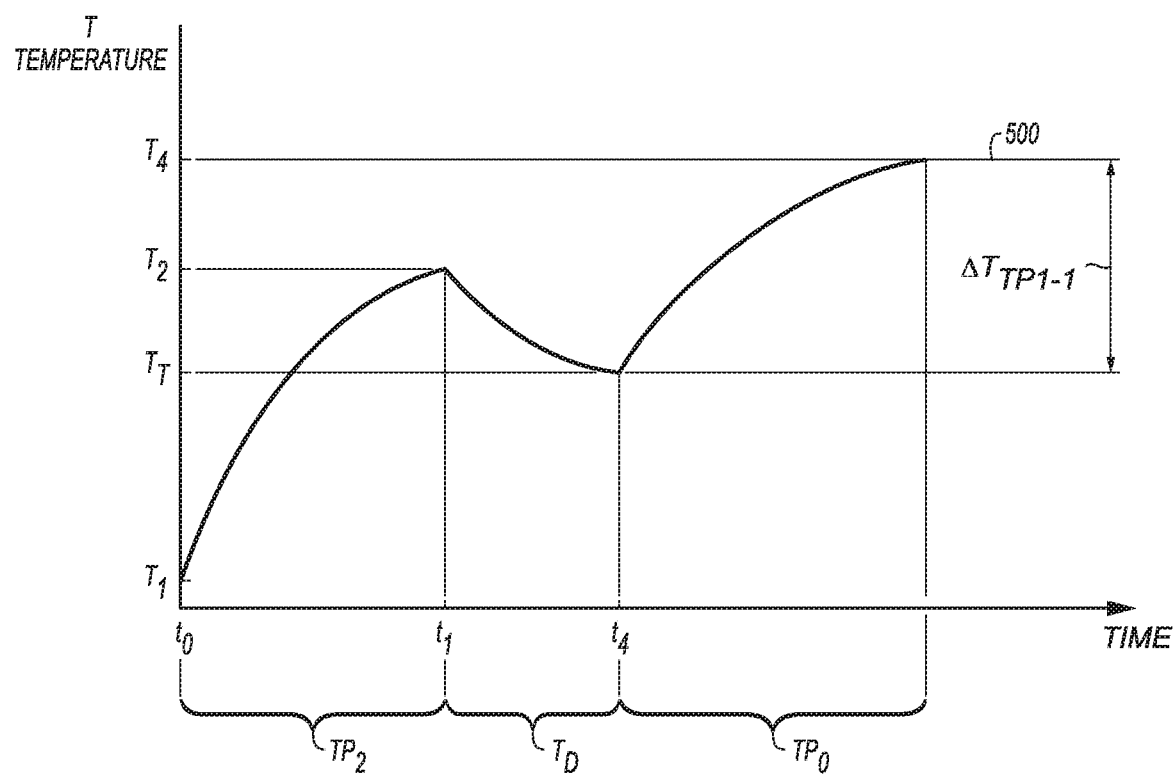
FIG. 8C corresponds to the graph of FIG. 8B, but shows the start of the delivery of the first electrical current signal set being delayed or restricted to the time $t_4$, the time $t_4$ being delayed by a delay period $T_D$, according to some embodiments.

According to some embodiments, the temperature comparison instructions associated with block 704 compare the determined temperature of the portion of the shaft member (e.g., 313 or 316) (e.g., provided in accordance with the temperature determination instructions of block 702 in some embodiments) with the temperature threshold $T_T$ (e.g., provided in accordance with the temperature threshold determination instructions of block 703 in some embodiments). If the comparison provides an indication that the determined temperature of the portion of the shaft member (e.g., 313 or 316) is greater than the provided temperature threshold $T_T$, then the transducer activation instructions associated with block 706 are configured to delay or restrict the delivery of at least the electrical current signal set in response to the indication according to some embodiments. For example, FIG. 8B provides an example in which the temperature $T_2$ is greater than the temperature threshold $T_T$ at time $t_1$. As it may be impractical to reduce the temperature $T_2$ instantaneously to the temperature threshold $T_T$ at time $t_1$, a delay or restriction in the delivery of the first electrical current signal set may be required. FIG. 8C corresponds to the graph of FIG. 8B, but shows the start of the delivery of the first electrical current signal set being delayed or restricted to the time $t_4$, the time $t_4$ being delayed by a delay period $T_D$ from the time $t_1$. It is noted, however, that the scaling between FIGS. 8B and 8C is not consistent, so the graphs in these figures should be viewed for purposes of illustration.

According to various embodiments, a duration of the delay period $T_D$ is sufficient to cause the temperature of the portion of the shaft member (e.g., 313 or 316) to drop from temperature $T_2$ to a temperature equal to or below the temperature threshold $T_T$. In some embodiments, the duration of the delay period $T_D$ is sufficient to cause the temperature of the portion of the shaft member (e.g., 313 or 316) to drop from temperature $T_2$ to a temperature equal to or below the temperature threshold $T_T$ during a state where no electrical current or electrical power is delivered by any conductor (e.g., 317) located in the shaft member (e.g., 313 or 316). In some embodiments, during the delay duration $T_D$ no electrical current or electrical power is delivered by any conductor (e.g., 317) to any particular transducer (e.g., 306) to cause the particular transducer to transmit energy sufficient to cause tissue ablation. Advantageously, when the start of the delivery of the first electrical current signal set is delayed or restricted to time $t_4$, the temperature of the portion of the shaft member (e.g., 313 or 316) starts at a temperature at or below temperature threshold $T_T$ and increases over the first time period $TP_0$ to a temperature $T_4$ that is at or below temperature limit 500 upon the immediate conclusion of the delivery of the first electrical current signal set (i.e., upon the immediate conclusion of the first time period $TP_0$). In contrast to, e.g., temperature $T_3$ shown in FIG. 8B, temperature $T_4$ in FIG. 8C, therefore, is a temperature that is insufficient or is determined to be insufficient to cause thermally-induced tissue cellular damage at least via contact between the portion of the shaft member (e.g., 313 or 316) and tissue, according to some embodiments. Temperature threshold $T_T$ is indicated as being below temperature limit 500 by an amount $\Delta T_{TP1-1}$ at least equal to the temperature change $\Delta T_{TP1}$ described earlier. The duration of the delay period $T_D$ may be determined in various manners. For example, in some embodiments, a lookup table may be provided in the memory device system (e.g., 130), the lookup table correlating various relating combinations of first or starting temperatures and various required temperature drops with the required delay periods $T_D$. In some embodiments, the duration of the delay period $T_D$ may be determined based at least on a predictive model. For example, in some embodiments, the cooling that occurs during delay period $T_D$ occurs during a particular state where no electrical current or electrical power is delivered by any conductor located in the shaft member (e.g., 313 or 316) to avoid additional resistive heating being generated within the shaft member. In such embodiments, a modified version of relationship (rel. #9) may be employed to determine the duration of the required delay period $T_D$ during the cooling, the modified version of relationship (rel. #9) being:

$$T_{[n+1]} = \left[1 - e^{-\frac{\delta t}{\tau}}\right] * (T_0) + T_{[n]} * e^{-\frac{\delta t}{\tau}} \quad \text{(rel. #11)}$$

where $T_{[n+1]}$ is the temperature of the portion of the shaft member at time $t_{n+1}$; $T_0$ is a temperature that the portion of the shaft member would approach in absence of any delivery of any electrical power or current via a conductor set located in the shaft member; $T_{[n]}$ is the temperature associated with the portion of the shaft member determined at a preceding time $t_n$; $\delta t$ is the time difference between $t_{n+1}$ and $t_n$; and $\tau$ is a time constant for the first order thermal system. It is noted that the variable $\Delta T_{[n]}$ that was present in relationship (rel. #9) is equal to zero since, according to some embodiments, no electrical current is flowing in the shaft member during the cooling to achieve the fastest cooling rate. In the example related to FIG. 8C, relationship (rel. #11) may be expressed as:

$$T_T = \left[1 - e^{-\frac{\delta t}{\tau}}\right] * (T_0) + T_2 * e^{-\frac{\delta t}{\tau}} \quad \text{(rel. #12)}$$

where $T_T$ is the temperature of the portion of the shaft member at time $t_4$; $T_0$ is a temperature that the portion of the shaft member would approach in absence of any delivery of any electrical power or current via a conductor set located in the shaft member; $T_2$ is the temperature associated with the portion of the shaft member determined at a preceding time $t_1$; $\delta t$ is the time difference between $t_4$ and $t_1$ (i.e., the duration of the delay period $T_D$, and $\tau$ is a time constant for the first order thermal system). It is noted that in some embodiments, $T_0$ is an ambient temperature that the portion of the shaft member would approach in absence of any delivery of any electrical power or current via the particular conductor set located in the shaft member. For example, if the shaft undergoes any heating (for example, by way of any power delivery through the shaft member via a conductor set other than the particular conductor set), then the portion of the shaft member would approach an ambient temperature in absence of any delivery of any delivery of any electrical power or current via the particular conductor set. In some embodiments, $T_0$ is a temperature slightly higher than ambient (e.g., 1 to 4 degrees Celsius) if relatively low levels of electrical current are delivered via a conductor set other than the particular conductor set in absence in absence of any delivery of any delivery of any electrical power or current via the particular conductor set. Such low levels of electrical current may be delivered, for various reasons including in the sensing of electrical voltages.

In addition to or in lieu of causing a delay or restriction of delivery of subsequent electrical power, (e.g., as discussed above with respect to FIGS. 7, 8A, 8B, and 8C) to allow the portion of the shaft member (e.g., 313 or 316) to cool from a prior delivery of electrical power, some embodiments reduce the number of transducers (e.g., 306) that will concurrently be activated to receive subsequent electrical power, e.g., to reduce the thermal load on the portion of the shaft member, resulting in two or more successive smaller sets of one or more transducers being activated. While such an approach may increase the overall duration of the delivery of the subsequent electrical power and may impact overall procedure time, such an approach may be preferable or advantageous in some circumstances. For example, assume that a group of ten transducers 306 are selected to receive tissue ablative energy as the delivery of the subsequent electrical power. However, also assume that if all ten transducers were to concurrently receive the tissue ablative energy without delay from completion of the prior delivery of electrical power, the portion of the shaft member (e.g., 313 or 316) would reach a temperature that exceeds a safe temperature limit (e.g., temperature limit 500), for instance, according to broken-line curve 506 in FIG. 8B. In such a circumstance, the above-discussed delay in delivering the subsequent tissue ablative energy may be introduced to allow the portion of the shaft member to cool (e.g., per the discussions associated with FIG. 8C above), according to some embodiments. In addition to or instead of introducing such a delay, the group of ten transducers 306 may be divided into two or more smaller groups of transducers, the smaller groups being sequentially activated so that each group receives its tissue ablative energy in turn, in order to reduce the thermal load on the portion of the shaft member due to the delivery of the subsequent tissue ablative energy. In this example, assume that the ten transducers 306 are divided into a first subgroup of five of the ten transducers and a second subgroup of the other five of the ten transducers. In some instances, for illustration purposes, the first subgroup may be experiencing improved tissue contact as compared to the second subgroup. Accordingly, it may be preferable to initiate the delivery of the tissue ablative energy to the first subgroup to allow additional time to improve the tissue contact of the second subgroup. In some instances, the delivery of the tissue ablative energy to the first subgroup may be delayed, instead of initiated immediately, for example, to allow for some cooling of the portion of the shaft member, but such a delay need not be for the maximum amount of delay that would be required if all ten transducers were concurrently activated to receive the tissue ablative energy. Accordingly, it can be seen that there may be instances where both a delay and reduction in the number of transducers to be concurrently activated are implemented.

Figure 9:
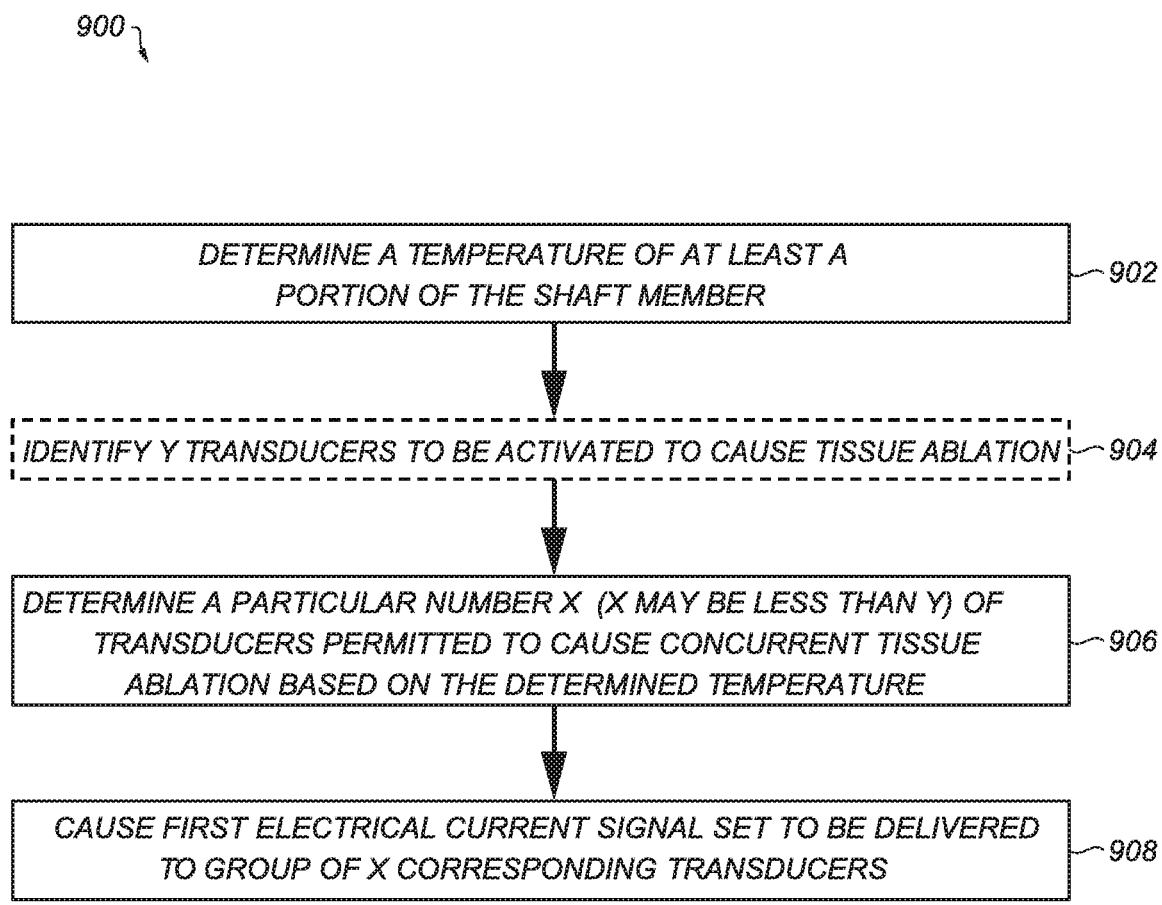
FIG. 9 is a block diagram of a method of controlling a number of transducers that receive electrical current signals based on a determined temperature of a portion of a shaft member of a medical device system, according to some embodiments.

With this context in mind, in some embodiments a method 900 shown in FIG. 9 is employed. In various example embodiments, a memory device system (e.g., 130 or 330) is communicatively connected to a data processing device system (e.g., 110, 310, or 324) and stores a program executable by the data processing device system to cause the data processing device system to execute method 900 via interaction with at least, for example, a transducer-based device (e.g., transducer-based device associated with system 100, 300, or 400). In these various embodiments, the program may include instructions configured to perform, or cause to be performed, various ones of the instructions associated with method 900. In some embodiments, method 900 may include a subset of the associated blocks or additional blocks than those shown in FIG. 9. In some embodiments, method 900 may include a different sequence between various ones of the associated blocks than those shown in FIG. 9.

In various embodiments, the data processing device system (e.g., 110, 310, or 324) is communicatively connected to a plurality of transducers (e.g., 306) via a plurality of conductors (e.g., 317). The transducers and conductors may be included in an input-output device system (e.g., 120) communicatively connected to the data processing device system (e.g., 110, 310, or 324). As discussed above, each conductor of the plurality of conductors may be coupled to a respective transducer (e.g., 306) (although one-to-many connections may occur in other embodiments), and at least a portion of each conductor may be located within the shaft member (e.g., 313 or 316).

Block 902 may be associated with instructions (e.g., temperature determination instructions) configured to cause the data-processing device system (e.g., 110, 310, or 324) to determine a temperature of at least a portion of the shaft member (e.g., 313 or 316). In this regard, the temperature determination instructions associated with block 902 may correspond to the temperature determination instructions associated with block 702, discussed above, according to some embodiments.

Block 904, which is optional according to some embodiments, may be associated with instructions (e.g., transducer selection instructions) configured to cause the data-processing device system (e.g., 110, 310, or 324) to select or identify Y transducers of the plurality of transducers (e.g., 306) to be activated to, e.g., cause tissue ablation. The selection or identification of the Y transducers may occur based on user-input, such as a user-selection of the Y transducers, based on machine input (e.g., based on sensing data provided by the transducers 306 to facilitate an automatic identification of a region of interest in a bodily cavity to be electrically isolated by tissue ablation and then an automatic selection of transducers that circumferentially surround the identified region of interest to cause the electrical isolation), or both based on user-input and machine input (e.g., a user selection of a region of interest in a bodily cavity to be electrically isolated by tissue ablation and then, based on sensing data provided by the transducers 306, an automatic machine selection of transducers that circumferentially surround the identified region of interest to cause the electrical isolation). U.S. Pat. No. 9,011,423, issued Apr. 21, 2015 describes various automatic selections of transducers around an identified region and such disclosures and related disclosures are hereby incorporated herein by reference.

Block 906 may be associated with instructions (e.g., transducer determination instructions) configured to cause the data-processing device system (e.g., 110, 310, or 324) to determine a particular number X of transducers permitted to cause concurrent tissue ablation based at least on the temperature determined according to block 902. For example, according to some embodiments, the above-discussed analyses associated with at least FIG. 8B may be repeatedly performed utilizing a measured or estimated temperature of the portion of the shaft member (e.g., at time $t_1$ in FIG. 8B) for X=1, X=2, X=3, etc., until a predicted temperature curve (e.g., like broken line curve 506 or 508) that is closest to, but does not exceed the safe temperature limit (e.g., limit 500) throughout the predicted duration of energy delivery (e.g., a respective duration $TP_0$ in FIG. 8B) to achieve required tissue ablation is achieved for a certain value of X.

For example, in some embodiments, a first predicted temperature curve for the portion of the shaft member (e.g., 313 or 316) may be determined according to the analyses discussed above with respect to at least FIG. 8B in the case where X=1, where only one transducer is activated to cause tissue ablation for a time period $TP_{X=1}$. If that first predicted temperature curve indicates a temperature less than a safe temperature limit (e.g., limit 500) throughout the time period $TP_{X=1}$, then a second predicted temperature curve is determined for X=2, where two transducers are concurrently activated to cause tissue ablation for a time period $TP_{X=2}$. If that second predicted temperature curve indicates a temperature less than the safe temperature limit (e.g., limit 500) throughout the time period $TP_{X=2}$, then a third predicted temperature curve is determined for X=3, where three transducers are concurrently activated to cause tissue ablation for a time period $TP_{X=3}$. If that third predicted temperature curve indicates a temperature greater than the safe temperature limit (e.g., limit 500) at some point throughout the time period $TP_{X=3}$, then X is selected to be X=2, since the second predicted temperature curve was the curve that was the closest to the safe temperature limit without exceeding it throughout its associated duration of transducer activation.

According to some embodiments, the transducer determination instructions 906 are configured to determine the particular number X of transducers permitted to cause concurrent tissue ablation to cause a temperature of a particular portion of the shaft member to remain at or below a determined temperature. In some embodiments, the transducer determination instructions are configured to determine the particular number X of transducers permitted to cause concurrent tissue ablation to cause a temperature of a particular portion of the shaft member to remain below a particular temperature sufficient to cause thermally-induced tissue cellular damage via the particular portion of the shaft member due to delivery of an electrical current signal set through one or more conductors (e.g., 317) within the shaft member. The particular number X of transducers may be less than a total number of the plurality of transducers, e.g., all transducers 306, according to some embodiments.

Block 908 may be associated with instructions (e.g., transducer activation instructions) configured to cause the data-processing device system (e.g., 110, 310, or 324) to cause a first electrical current signal set to be delivered (e.g., delivered concurrently) via a first set of conductors of the plurality of conductors, the first set of conductors corresponding to a group of X corresponding transducers of the plurality of transducers based on the determination of the number X of transducers (e.g., per block 906) permitted to cause concurrent tissue ablation, the delivered first electrical current signal set sufficient to cause tissue ablation via the group of X corresponding transducers of the plurality of transducers. In some embodiments, the transducer activation instructions associated with block 908 are configured to cause the first electrical current signal set to be delivered via the first set of conductors of the plurality of conductors to the group of X corresponding transducers of the plurality of transducers to cause concurrent tissue ablation.

In some instances, Y (e.g., determined according to block 904) is greater than X (e.g., determined according to block 906). In other words, for example, the total number of Y transducers selected to cause tissue ablation according to block 904, may exceed a number (e.g., a maximum number) X of transducers determined according to block 906 that may be concurrently activated while ensuring that the temperature of the portion of the shaft member (e.g., 313 or 316) remains at a safe level (e.g., a temperature insufficient to cause thermally-induced tissue cellular damage due to contact between the portion of the shaft member (e.g., 313 or 316) and tissue). In such a case, when Y is greater than X, and the transducer activation instructions (e.g., associated with block 908) are configured to cause the first electrical current signal set to be concurrently delivered to a smaller number of transducers (e.g., X) than the number of transducers (e.g., Y) identified according to the transducer selection instructions (e.g., associated with block 908). In such a case, the originally selected Y transducers may be divided into two or more subgroups, where all of the transducers in a subgroup are concurrently activated, but the two or more subgroups are sequentially activated as discussed above to control the temperature of the portion of the shaft member (e.g., 313 or 316), according to some embodiments. For example, the originally selected Y transducers may be divided into a first subgroup of X transducers, the first subgroup concurrently activated according to the instructions associated with block 908, according to some embodiments. Then, all or a portion of the method 900 may be repeated, replacing the original value of Y with (Y-X). When all transducers of the originally selected Y transducers have been activated through multiple iterations of all or a portion of method 900, the process of activating the originally selected Y transducers is complete according to some embodiments.

In this regard, according to some embodiments, the transducer activation instructions associated with block 908 are configured to cause a second electrical current signal set to be delivered via a second set of conductors of the plurality of the conductors (e.g., 317) to at least some of the Y transducers (e.g., at least some transducers in the set Y-X in some embodiments) after completion of the delivery of the first set electrical current signal set via a first set of conductors of the plurality of conductors to the group of X corresponding transducers of the plurality of transducers. In some embodiments, the delivered second electrical current signal set is sufficient to cause tissue ablation via the at least some of the Y transducers (e.g., at least some transducers in the set Y-X in some embodiments). According to some embodiments, the transducer activation instructions associated with block 908 are configured to cause the second electrical current signal set to be delivered via the second set of conductors of the plurality of conductors to the at least some of the Y transducers to cause concurrent tissue ablation. According to some embodiments, the at least some of the Y transducers includes at least one transducer not included in the group of X corresponding transducers of the plurality of transducers, and, according to some embodiments, the at least some of the Y transducers do not include any transducer included in the group of X corresponding transducers of the plurality of transducers.

As discussed above, the temperature of the portion of the shaft member (e.g., 313 or 316) determined according to the instructions associated with block 902 may be an ambient temperature of the portion of the shaft member, may be less than or equal to a temperature of a portion of the body that at least part of the shaft member is percutaneously deliverable through, or may be, among other things, a heated state of the portion of the shaft member due to prior delivery of electrical power through one or more conductors (e.g., 317) within the shaft member. For instance, the group of X corresponding transducers of the plurality of transducers may be a first transducer set, and the transducer activation instructions associated with block 908 may be configured to cause electrical power to be delivered to at least a second transducer set of the plurality of transducers, the electrical power delivered to at least the second transducer set delivered prior to the delivery of the first electrical current signal set to the first transducer set, such that, e.g., the temperature determination instructions associated with block 902 may be configured to determine the temperature of the portion of the shaft member at least after the electrical power has been delivered to at least the second transducer set. (Note that phrases like "second transducer set", "first transducer set", "first time period", "second time period", "first temperature", "second temperature", and the like may refer to the same respective sets in some embodiments, and may refer to different respective sets in other embodiments.) The electrical power delivered to at least the second transducer set may be sufficient to cause tissue ablation via the second transducer set. For another example, the temperature determination instructions associated with block 902 may be configured to determine the temperature of the portion of the shaft member (e.g., 313 or 316) in an unheated state. For instance, the temperature determination instructions associated with block 902 may be configured to determine the temperature of the portion of the shaft member (e.g., 313 or 316) at least prior to the data processing device system causing electrical power to be delivered to any transducer of the plurality of transducers (e.g., 306). Or, for instance, the temperature determination instructions associated with block 902 may be configured to determine the temperature of the portion of the shaft member (e.g., 313 or 316) at least prior to the data processing device system causing electrical power to be delivered to any particular transducer of the plurality of transducers (e.g., 306) to cause the particular transducer to emit energy sufficient for tissue ablation. According to some embodiments, the temperature determination instructions associated with block 902 may be configured to determine the temperature of the portion of the shaft member (e.g., 313 or 316) based at least on a predictive model (e.g., based on at least relationship (rel. #9) discussed above) or a particular characteristic sensed by, e.g., the above discussed first temperature sensor (e.g., 342a or 342b).

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above provide further embodiments.

These and other changes may be made to various embodiments in light of the above-detailed description. In general, in the following claims, the terms used should not be construed to limit the invention to the specific embodiments disclosed in the specification and the claims, but should be construed to include other electrode-based device systems including all medical treatment device systems and all medical diagnostic device systems in accordance with the claims. Further, it should be noted that, although several of the above-discussed embodiments are described within the context of an intra-cardiac medical device system, other embodiments apply to other medical and non-medical device systems. Accordingly, the invention is not limited by this disclosure, but instead its scope is to be determined entirely by the claims.

What is claimed is:

1. A medical device system comprising:
   a structure;
   a plurality of transducers located on the structure;
   a shaft member configured to percutaneously deliver the structure to a location within a patient, the shaft member comprising a distal end portion and a proximal end portion, at least part of the shaft member sized to be percutaneous deliverable toward the location within the patient distal end portion ahead of the proximal end portion;
   a plurality of conductors coupled to the plurality of transducers, at least a portion of each conductor of the plurality of conductors located within the shaft member; and
   a controller operatively coupled to the plurality of transducers and configured to cause delivery of electrical power to the plurality of transducers via the plurality of conductors, wherein the controller is configured to cause delivery, via a first set of the plurality of conductors, of first electrical power to a transducer set of the plurality of transducers, the first electrical power sufficient to cause, if delivered for a first time period, a portion of the shaft member to transition from a first temperature to a steady-state temperature immediately upon conclusion of the first time period, the steady-state temperature determined sufficient to cause thermally-induced tissue cellular damage, wherein the controller is configured to cause delivery of the first electrical power to the transducer set for a maximum of a second time period, the second time period shorter than the first time period, and the delivery of the first electrical power to the transducer set for the second time period (a) sufficient to cause tissue ablation via the transducer set, and (b) sufficient to cause the portion of the shaft member to transition from the first temperature to a second temperature immediately upon conclusion of the second time period, and wherein the controller is configured to determine the second temperature, which is less than the steady-state temperature and determined insufficient to cause thermally-induced tissue cellular damage.

2. The medical device system of claim 1, wherein delivery of the first electrical power to the transducer set, if delivered for a third time period longer than the second time period, is sufficient to cause the portion of the shaft member to transition from the first temperature to a third temperature, the third temperature determined sufficient to cause thermally-induced tissue cellular damage.

3. The medical device system of claim 2, wherein the third time period is shorter than the first time period.

4. The medical device system of claim 1, wherein the second temperature is a temperature within a range of 43 to 60 degrees Celsius, inclusive.

5. The medical device system of claim 1, wherein the second temperature is a temperature less than or equal to 48 degrees Celsius, and the second time period is shorter than 10 minutes.

6. The medical device system of claim 1, wherein the second temperature is a temperature less than or equal to 60 degrees Celsius, and the second time period is shorter than 1 minute.

7. The medical device system of claim 1, wherein the first temperature is an ambient temperature of the portion of the shaft member.

8. The medical device system of claim 1, wherein the first temperature is less than or equal to a temperature of a portion of the patient that the at least part of the shaft member is percutaneously deliverable through.

9. The medical device system of claim 1, wherein the transducer set is a first transducer set and the controller is configured to cause particular electrical power to be delivered to at least a second transducer set of the plurality of transducers, the particular electrical power delivered to at least the second transducer set prior to the delivery of the first electrical power to the first transducer set, and wherein the first temperature is a temperature of the portion of the shaft member after the particular electrical power is delivered to at least the second transducer set.

10. The medical device system of claim 9, wherein the particular electrical power delivered to at least the second transducer set is sufficient to cause tissue ablation via the second transducer set.

11. The medical device system of claim 1, wherein the first temperature is a temperature of the portion of the shaft member prior to the controller causing electrical power to be delivered to any transducer of the plurality of transducers.

12. The medical device system of claim 1, wherein the first temperature is a temperature of the portion of the shaft member prior to the controller causing electrical power to be delivered to any particular transducer of the plurality of transducers to cause the particular transducer to emit energy sufficient for tissue ablation.

13. The medical device system of claim 1, comprising at least a first temperature sensor configured to sense the first temperature, the second temperature, or both the first temperature and the second temperature.

14. The medical device system of claim 13, wherein the first temperature sensor is located on or in the shaft member.

15. The medical device system of claim 14, wherein the distal end portion of the shaft member comprises a distal end, and the proximal end portion of the shaft member comprises a proximal end, and wherein the first temperature sensor is located on or in the shaft member at a location closer to the distal end of the shaft member than to the proximal end of the shaft member.

16. The medical device system of claim 14, wherein the distal end portion of the shaft member comprises a distal end, and the proximal end portion of the shaft member comprises a proximal end, and wherein the first temperature sensor is located on or in the shaft member at a location closer to the proximal end of the shaft member than to the distal end of the shaft member.

17. The medical device system of claim 13, wherein the first temperature sensor is provided at least in part by a first conductor, at least a portion thereof located in the shaft member, and wherein the controller is configured to determine the first temperature, the second temperature, or both the first temperature and the second temperature based at least on a resistance of at least part of the first conductor.

18. The medical device system of claim 1, wherein the shaft member comprises at least a first lumen extending between the proximal end portion of the shaft member and the distal end portion of the shaft member, and wherein the plurality of conductors are located in the first lumen.

19. The medical device system of claim 1, wherein the shaft member comprises at least a first lumen extending between the proximal end portion of the shaft member and the distal end portion of the shaft member, and wherein the structure is configured to be delivered through the first lumen as the structure is percutaneously delivered toward the location within the patient.

20. The medical device system of claim 1, wherein at least part of each conductor of the plurality of conductors is located within the portion of the shaft member.

21. The medical device system of claim 1, wherein the structure is physically coupled to the distal end portion of the shaft member.

22. The medical device system of claim 1, wherein the shaft member comprises a length along the shaft member extending between the proximal end portion of the shaft member and the distal end portion of the shaft member, the length sufficient to position the proximal end portion of the shaft member at a location outside the patient during a state in which the structure is located at the location within the patient.

23. The medical device system of claim 1, wherein the structure is selectively moveable between a delivery configuration in which the structure is suitably sized to be percutaneously deliverable to the location within the patient, and a deployed configuration in which the structure is sized too large to be percutaneously deliverable to the location within the patient.

24. The medical device system of claim 1, wherein the controller is configured to determine the second temperature based at least on a predictive model and (a) information related to the first temperature, (b) information related to the first electrical power, (c) information related to the second time period, or a combination of two or all of (a), (b), and (c).

25. The medical device system of claim 1, wherein the steady-state temperature is determined sufficient to cause thermally-induced tissue cellular necrosis.

26. The medical device system of claim 2, wherein the third temperature is determined sufficient to cause thermally-induced tissue cellular necrosis.

27. The medical device system of claim 1, wherein each transducer of the plurality of transducers comprises a respective one of a plurality of electrodes.

28. The medical device system of claim 1, wherein the first temperature is a temperature of the portion of the shaft member at the start of the first time period.

29. The medical device system of claim 1, wherein the portion of the shaft member does not include any of the plurality of transducers.

30. The medical device system of claim 1, wherein the portion of the shaft member does not include any ablation transducer.

31. The medical device system of claim 1, wherein the portion of the shaft member does not include any therapeutic transducer.

* * * * *